United States Patent
Lee et al.

(10) Patent No.: US 9,434,779 B2
(45) Date of Patent: Sep. 6, 2016

(54) GROWTH DIFFERENTIATION FACTOR 11 (GDF-11) FOR TREATMENT OF DIASTOLIC HEART FAILURE

(71) Applicants: The Brigham and Women's Hospital, Inc., Boston, MA (US); President and Fellows of Harvard College, Cambridge, MA (US)

(72) Inventors: Richard T. Lee, Weston, MA (US); Francesco Loffredo, Boston, MA (US); James Pancoast, Cambridge, MA (US); Matthew Steinhauser, Newton, MA (US); Amy Wagers, Cambridge, MA (US)

(73) Assignees: The Brigham and Women's Hospital, Inc., Boston, MA (US); President and Fellows of Harvard College, Cambridge, MA (US)

(*) Notice: Subject to any disclaimer, the term of this patent is extended or adjusted under 35 U.S.C. 154(b) by 0 days.

(21) Appl. No.: 14/385,578

(22) PCT Filed: Mar. 11, 2013

(86) PCT No.: PCT/US2013/030140
§ 371 (c)(1),
(2) Date: Sep. 16, 2014

(87) PCT Pub. No.: WO2013/142114
PCT Pub. Date: Sep. 26, 2013

(65) Prior Publication Data
US 2015/0045297 A1  Feb. 12, 2015

Related U.S. Application Data

(60) Provisional application No. 61/612,550, filed on Mar. 19, 2012, provisional application No. 61/649,962, filed on May 22, 2012.

(51) Int. Cl.
| A61K 38/00 | (2006.01) |
| A61K 38/16 | (2006.01) |
| A61K 38/17 | (2006.01) |
| A61K 38/18 | (2006.01) |
| C07K 14/51 | (2006.01) |
| C07K 14/71 | (2006.01) |
| A61K 31/7088 | (2006.01) |

(52) U.S. Cl.
CPC ........... *C07K 14/51* (2013.01); *A61K 31/7088* (2013.01); *A61K 38/1875* (2013.01); *C07K 14/71* (2013.01)

(58) Field of Classification Search
None
See application file for complete search history.

(56) References Cited

U.S. PATENT DOCUMENTS

| 6,008,434 A * | 12/1999 | Lee et al. .................. 800/18 |
| 6,517,835 B2 | 2/2003 | Lee et al. |
| 2006/0078532 A1 | 4/2006 | Omoigui |
| 2008/0051328 A1 | 2/2008 | Sharma et al. |
| 2009/0298761 A1 | 12/2009 | Engelman |

FOREIGN PATENT DOCUMENTS

| WO | 9835019 A1 | 8/1998 |
| WO | 9854572 A1 | 12/1998 |
| WO | 2004073633 A2 | 9/2004 |
| WO | 2008109167 A2 | 9/2008 |

OTHER PUBLICATIONS

McNally (2016, Circulation Research 118:6-8).*
Loffredo et al. (2013, Cell 153:828-839).*
Smith et al. (2015, Circulation Research 117:926-932).*
Poggiolo et al. (2016, Circulation Research 118:29-37).*
Ahn et al. (2016, Can J Vet Res 80(1): 90-92).*
Wells (1990, Biochemistry 29:8509-8517).*
Ngo et al. (1994, The Protein Folding Problem and Tertiary Structure Prediction, Merz et al., eds., Birkhauser, Boston, pp. 492-495).*
Tokuriki et al. (2009, Curr. Opin. Struc. Biol. 19:596-604).*
Phillips (2001, J Pharm Pharmacology 53:1169-1174).*
Vidal et al. (2005, European Journal of Cancer 41:2812-2818).*
Breitbart et al., "Myostatin from the heart: local and systemic actions in cardiac failure and muscle wasting", Heart and Circulatory Physiology, 300(6):H1973-H1982 (2011).
Conboy et al., "Heterochronic parabiosis for the study of the effects of aging on stem cells and their niches", Cell Cycle, 11(12):2260-2267 (2012).
Dai et al., "Overexpression of Catalase Targeted to Mitochondria Attenuates Murine Cardiac Aging", Circulation, 119 (21):2789-2797 (2009).
Harmon et al., "GDF11 modulates NGN3+ islet progenitor cell number and promotes cell differentiation in pancreas development", Development, 131(24):6163-6174 (2004).
Li et al., "Transgenic overexpression of bone morphogenetic protein 11 propeptide in skeleton enhances bone formation", Biochemical and Biophysical Research Communications, 416(3):2011).
McPherron et al., BMC Dev Bioo., 9:9 (2009) (Redundancy of myostatin and growth/differentation factor 11 function.

(Continued)

*Primary Examiner* — Elizabeth C Kemmerer
(74) *Attorney, Agent, or Firm* — Nixon Peabody LLP

(57) ABSTRACT

The technology described herein relates to treatments for, e.g., diastolic heart failure, cardiac hypertrophy, and related conditions.

9 Claims, 17 Drawing Sheets

(56) References Cited

OTHER PUBLICATIONS

Zhou et al., Cell, 142:531-543 (2010). "Reversal of cancer cachexia and muscle wasting by ActRIIB antagonism leads to prolonged survival."
Souza, Mol Endocrinol, 22(12):2689-2702 (2008). "Proteomic identification and function validation fo activins and bone morphogenetic protwin 11 as candidate novel muscle mass regulators."
Lima, J. Exp, 91(1):54-62 (2010). "Myostatin and follistatin expression in skeletal muscles of rats with chronic heart failure."
Shyu, Eur. J. Clin. Invest, 36:713-719 (2006). "Myostatin expression in ventricular myocardium in a rat model of volume-overload heart failure."
Garner, Dev Bio., 229(2):407-420 (2001). "GDF1 is a negative regulator of chondrogenesis and myogenesis in the developing chick limb."
Morissette, Circ, Res, 99(1):15-24 (2006). "Myostatin regulates cardiomyocyte growth through modulation of AKT signaling."
Olson et al., "Association of growth differentiation factor 11/8, putative anti-ageing factor, with cardiovascular outcomes and overall mortality in humans: analysis of the Heart and Soul and HUNT3 cohorts" European Heart Journal European Heart Journal, 36(48):3426-3434 (2015).

* cited by examiner

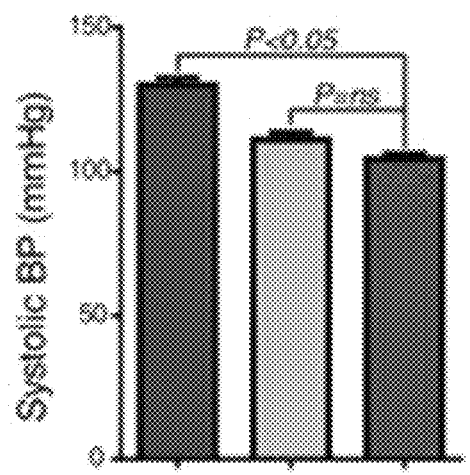
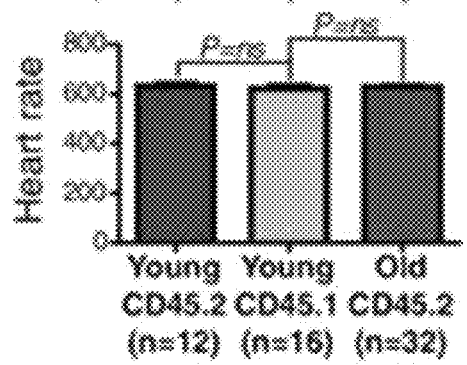
Fig. 3A
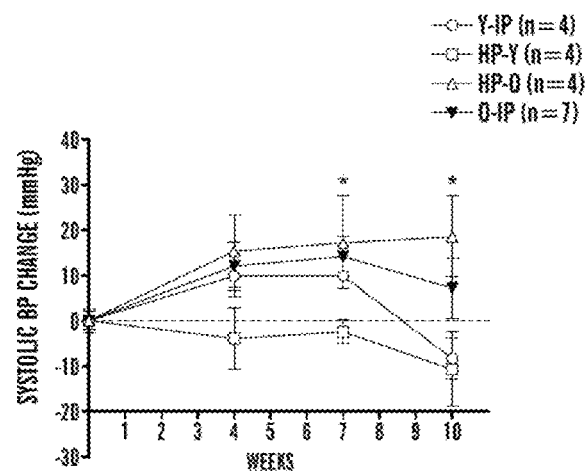
FIG. 3B
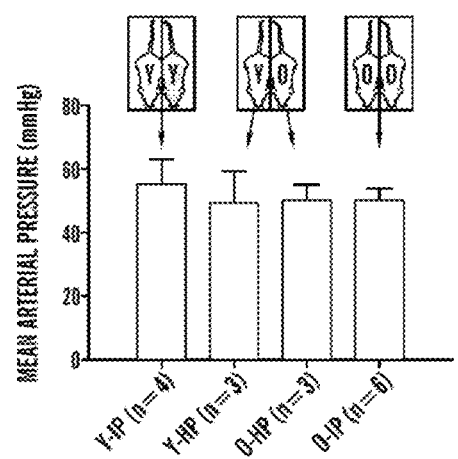
FIG. 3C

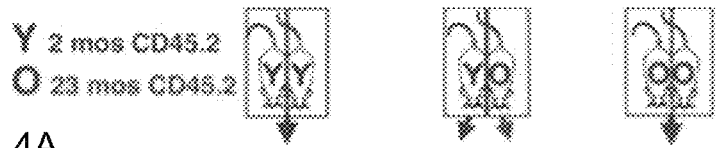
Fig. 4A
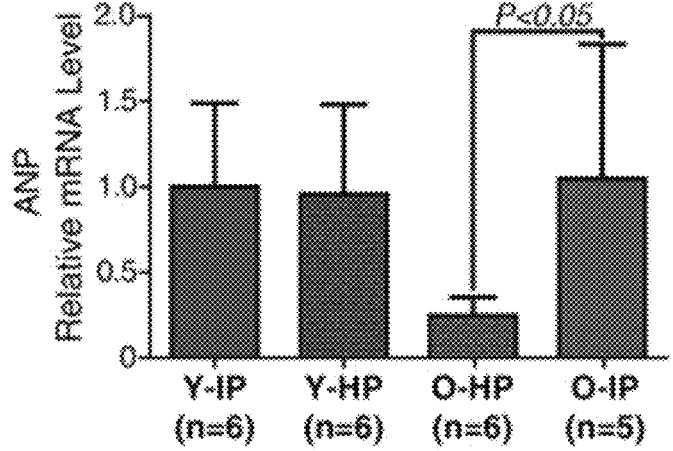
Fig. 4B
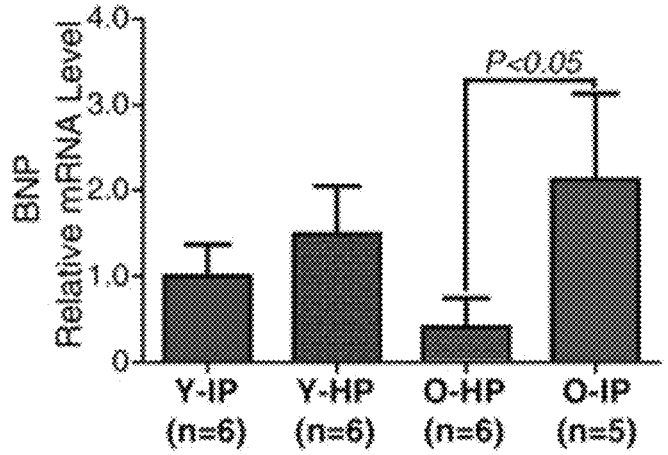
Fig. 4C
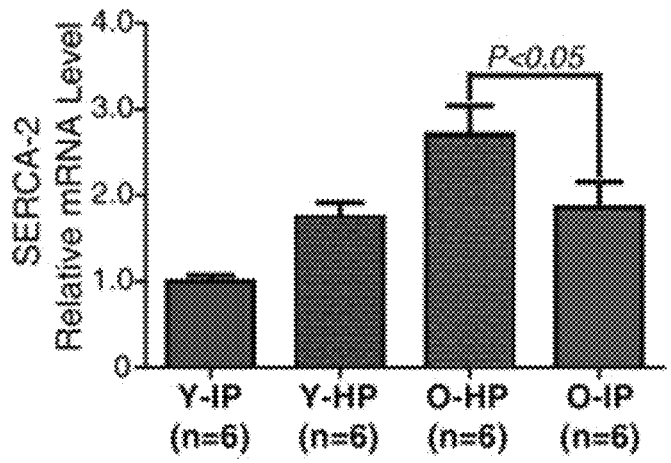

```
>lcl|8305 unnamed protein product
Length=375

Score =  492 bits (1266),  Expect = 3e-177, Method: Compositional matrix adjust.
 Identities = 227/347 (65%), Positives = 279/347 (80%), Gaps = 11/347 (3%)

Query  62   CPVCWRQHSRELRLESIKSQILSKLRLKEAPNISREVVKQLLPKAPPLQQILDLHDFQG   121
            C C WRQ+++  R+E+IK QILSKLRL+ APNIS++V++QLLPKAPPL++++D +D Q
Sbjct  39   CNACTWRQNTKSSRIEAIKIQILSKLRLETAPNISKDVIRQLLPKAPPLRELIDQYDVQR   98

Query  122  DALQPEDFLEEDEYHATTETVISMAQETDPAVQTDGSPLCCHFHFSPKVMFTKVLKAQLW   181
            D   + LE+D+YHATTET+I+M  E+D  +Q DG P CC F FS K+ + KV+KAQLW
Sbjct  99   DD-SSDGSLEDDDYHATTETIITMPTESDFLMQVDGKPKCCFFKFSSKIQYNKVVKAQLW   157

Query  182  VYLRPVPRPATVYLQILRL-KPLTGEGTAGGGGGGRRHIRIRSLKIELHSRSGHWQSIDF   240
            +YLRPV P TV++QILRL KP+           G R+  IRSLK++++  +G WQSID
Sbjct  158  IYLRPVETPTTVFVQILRLIKPMKD---------GTRYTGIRSLKLDMNPGTGIWQSIDV   208

Query  241  KQVLHSWFRQPQSNWGIEINAFDPSGTDLAVTSLGPGAEGLHPFMELRVLENTKRSRRNL   300
            K VL +W +QP+SN GIEI A D +G DLAVT GPG +GL+PF+E++V +  KRSPR+
Sbjct  209  KTVLQNWLKQPESNLGIEIKALDENGHDLAVTFPGPGEDGLNPFLEVKVTDTPKRSRRDF   268

Query  301  GLDCDEHSSESRCCRYPLTVDFEAFGWDWIIAPKRYKANYCSGQCEYMFMQKYPHTHLVQ   360
            GLDCDEHS+ESRCCRYPLTVDFEAFGWDWIIAPKRYKANYCSG+CE++F+QKYPHTHLV
Sbjct  269  GLDCDEHSTESRCCRYPLTVDFEAFGWDWIIAPKRYKANYCSGECEFVFLQKYPHTHLVH   328

Query  361  QANPRGSAGPCCTPTKMSPINMLYFNDKQQIIYGKIPGMVVDRCGCS  407
            QANPRGSAGPCCTPTKMSPINMLYFN K+QIIYGKIP MVVDRCGCS
Sbjct  329  QANPRGSAGPCCTPTKMSPINMLYFNGKEQIIYGKIPAMVVDRCGCS  375
```

Fig. 8

```
>lcl|1497 unnamed protein product
Length=405

Score =  727 bits (1876),  Expect = 0.0, Method: Compositional matrix adjust.
 Identities = 359/361 (99%), Positives = 359/361 (99%), Gaps = 0/361 (0%)

Query  47   RSSPPAPSVAPEPDGCPVCVWRQHSPELRLESIKSQILSKLRLKEAPNISREVVKQLLPK  106
            RSSRPAPS  PEPDGCPVCVWRQHSRELRLESIKSQILSKLRLKEAPNISREVVKQLLPK
Sbjct  45   RSSRPAPSAPPEPDGCPVCVWRQHSPELRLESIKSQILSKLRLKEAPNISREVVKQLLPK  104

Query  107  APPLQQILDLHDFQGDALQPEDFLEEDEYHATTETVISMAQETDPAVQTDGSPLCCHFHF  166
            APPLQQILDLHDFQGDALQPEDFLEEDEYHATTETVISMAQETDPAVQTDGSPLCCHFHF
Sbjct  105  APPLQQILDLHDFQGDALQPEDFLEEDEYHATTETVISMAQETDPAVQTDGSPLCCHFHF  164

Query  167  SPKVMFTKVLKAQLWVYLRPVPRPATVYLQILRLKPLTGEGTAGGGGGRPHIRIRSLKI  226
            SPKVMFTKVLKAQLWVYLRPVPRPATVYLQILRLKPLTGEGTAGGGGGRPHIRIRSLKI
Sbjct  165  SPKVMFTKVLKAQLWVYLRPVPRPATVYLQILRLKPLTGEGTAGGGGGRPHIRIRSLKI  224

Query  227  ELHSRSGHWQSIDFKQVLHSWFRQPQSNWGIEINAFDPSGTDLAVTSLGPGAEGLHPFME  286
            ELHSRSGHWQSIDFKQVLHSWFRQPQSNWGIEINAFDPSGTDLAVTSLGPGAEGLHPFME
Sbjct  225  ELHSRSGHWQSIDFKQVLHSWFRQPQSNWGIEINAFDPSGTDLAVTSLGPGAEGLHPFME  284

Query  287  LRVLENTKRSRRNLGLDCDEHSSESRCCRYPLTVDFEAFGWDWIIAPKRYKANYCSGQCE  346
            LRVLENTKRSRRNLGLDCDEHSSESRCCRYPLTVDFEAFGWDWIIAPKRYKANYCSGQCE
Sbjct  285  LRVLENTKRSRRNLGLDCDEHSSESRCCRYPLTVDFEAFGWDWIIAPKRYKANYCSGQCE  344

Query  347  YMFMQKYPHTHLVQQANPRGSAGPCCTPTKMSPINMLYFNDKQQIIYGKIPGMVVDRCGC  406
            YMFMQKYPHTHLVQQANPRGSAGPCCTPTKMSPINMLYFNDKQQIIYGKIPGMVVDRCGC
Sbjct  345  YMFMQKYPHTHLVQQANPRGSAGPCCTPTKMSPINMLYFNDKQQIIYGKIPGMVVDRCGC  404

Query  407  S  407
            S
Sbjct  405  S  405
```

Fig. 9

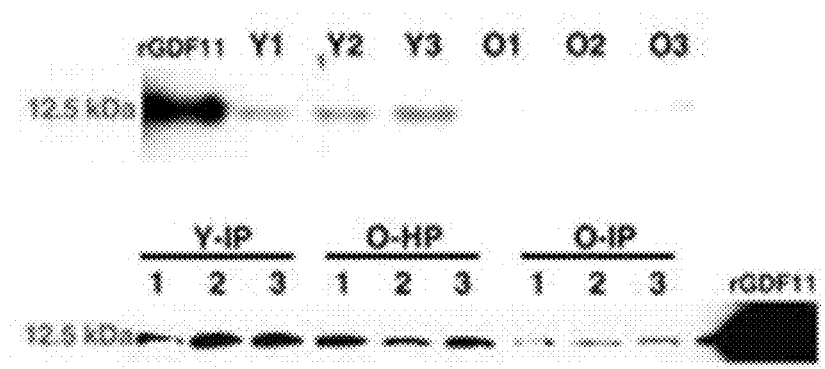
Fig. 12A
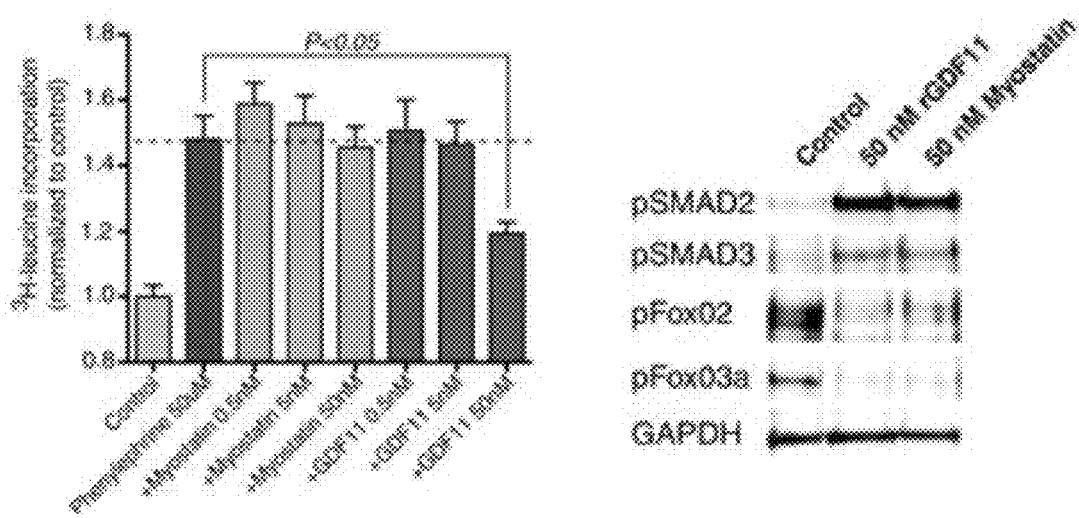
Fig. 12B
Fig. 12C

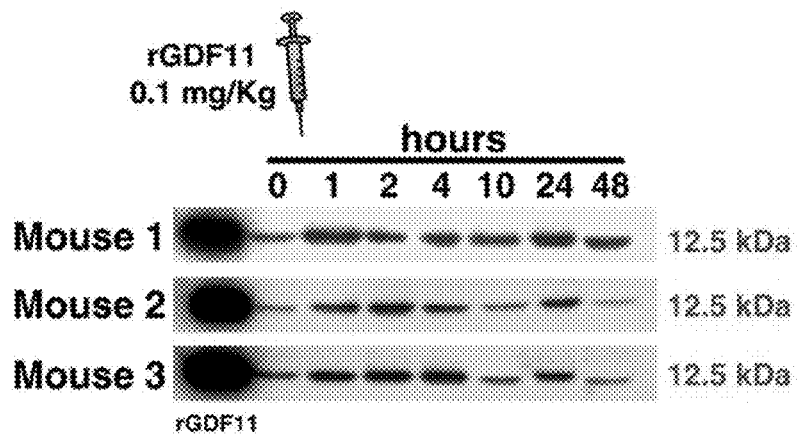
Fig. 14
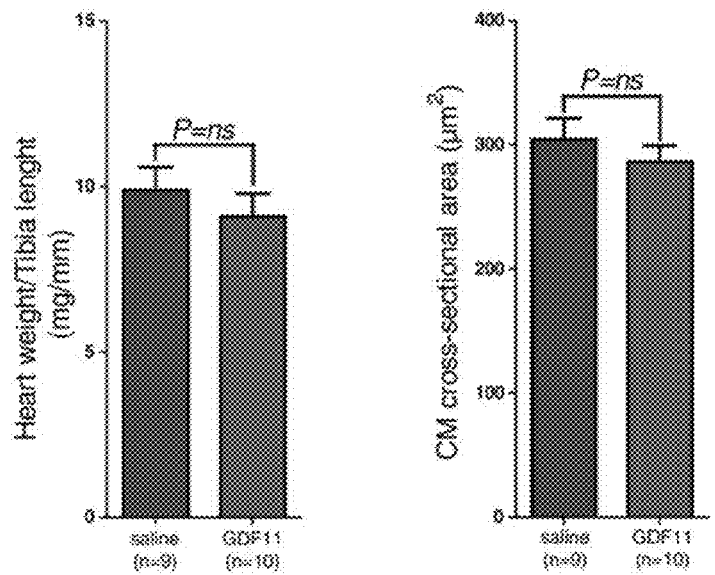
Fig. 15A    Fig. 15B
Fig. 15C

GROWTH DIFFERENTIATION FACTOR 11 (GDF-11) FOR TREATMENT OF DIASTOLIC HEART FAILURE

CROSS-REFERENCE TO RELATED APPLICATIONS

This application is a 35 U.S.C. 371 National Phase Entry Application of International Application No. PCT/US2013/030140 filed Mar. 11, 2013, which designates the U.S., and which claims benefit under 35 U.S.C. §119(e) of U.S. Provisional Application Nos. 61/612,550, filed Mar. 19, 2012, and 61/649,962, filed May 22, 2012, the contents of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Mar. 7, 2013, is named 043214-073892-PCT_SL.txt and is 58,885 bytes in size.

TECHNOLOGICAL FIELD

Embodiments of the technology described herein relate to treatments for diastolic heart failure, cardiac hypertrophy, and related conditions.

BACKGROUND

Aging of multicellular organisms can lead to the loss of normal cardiac function, ultimately resulting in heart failure. Heart failure affects approximately 1% of individuals over 50 but over 5% of individuals over 75, and with the ongoing steep rise in the proportion of elderly individuals within our population, age-related heart failure is certain to become an increasingly prevalent health condition. Most age-related heart failure is in the setting of normal systolic function, and this is a condition often associated with cardiac hypertrophy (i.e. enlargement of heart tissue) and called "diastolic heart failure" (G, P. Aurigemma, N Engl J Med 355, 308 (Jul. 20, 2006)). Diastolic heart failure accounts for 40-60% of heart failure cases (G, P. Aurigemma, N Engl J Med 2006 355: 308; S. A. Hunt et al., Circulation 2009 119:e391; D. W. Kitzman, K. R. Daniel, Clin Geriatr Itled 2007 23:83; J. C. Finerty, Physiol Rev 1952 32:277). The prognosis of diastolic heart failure may be as poor as systolic heart failure (G, P. Aurigemma, N Engl J Med 2006 355:308), with a 5-year risk of death after an initial heart failure hospitalization approaching that of common malignancies (D. E. Wright, et al. Science 2001 294:1933). Although much progress has been made in the treatment of systolic heart failure, with substantial improvements in outcome over the past two decades, progress in treatment of diastolic heart failure has been much more elusive (S. A. Hunt et al., Circulation 119, e391 (Apr. 14, 2009)). Indeed, one can argue that there are no specific therapies for patients who experience the ventricular "stiffening" associated with the diastolic dysfunction that accompanies aging (D. W. Kitzman, K. R. Daniel, Clin Geriatr Itled 23, 83 (February, 2007)). It is this clinical reality that may explain the observation that mortality is declining for systolic heart failure but not diastolic heart failure (J. C. Finerty, Physiol Rev 1952 32:277), and underscores the enormous clinical demand for new therapeutic strategies targeting diastolic failure.

Diastolic heart failure is a clinical syndrome that occurs in a variety of pathophysiologic settings, including long-standing hypertension, valvular disease such as aortic stenosis, genetic hypertrophic cardiomyopathy, and as a result of aging. These disparate etiologies converge with some common pathophysiologic threads, most obviously with cellular hypertrophy or increased diameter of cardiomyocytes; which translates into increased thickness of the heart wall without significantly reducing squeezing capacity (systolic function). Myocardial hypertrophy is an important contributor to the impairment in relaxation or increased stiffness that causes diastolic heart failure (A. J. Wagers, et al., Science 2002 297:2256).

SUMMARY

Embodiments of the technology described herein are based on the discovery that the level of GDF11 in the blood of an animal decreases with age and this decrease in GDF11 level is associated with cardiac hypertrophy in the aging animal. The inventors have further discovered the therapeutic potential of increasing the GDF11 level in an animal, particularly as it relates to cardiac conditions, including those associated with aging.

Accordingly, in one aspect, provided herein is a method of treating a cardiovascular condition, the method comprising administering to a subject a composition which increases the level of GDF11 polypeptide in the subject.

In some embodiments, the level of GDF11 polypeptide is the level of GDF11 in the circulation of the subject. In some embodiments, the level of GDF11 polypeptide is the level of GDF11 in the cardiac tissue of the subject.

In some embodiments, the subject has or has been diagnosed with a condition selected from the group consisting of: diastolic heart failure; cardiac hypertrophy; age-related cardiac hypertrophy; hypertension; valvular disease; aortic stenosis; genetic hypertrophic cardiomyopathy; or stiffness of the heart due to aging.

In some embodiments, the composition comprises a GDF11 polypeptide. In some embodiments, the composition comprises a GDF11 polypeptide comprising the amino acid sequence of SEQ ID NO 14. In some embodiments, the composition comprises a GDF11 polypeptide comprising the amino acid sequence of SEQ ID NO 15. In some embodiments, the composition comprises a GDF11 polypeptide comprising the amino acid sequence of SEQ ID NO 2. In some embodiments, the composition comprises a GDF11 polypeptide comprising the amino acid sequence of SEQ ID NO: 1.

In some embodiments, the composition comprises homodimers of GDF11 polypeptides comprising the amino acid sequence of any of SEQ ID NO 1, 2, 14, and/or 15. In some embodiments, the composition comprises complexes of GDF11 polypeptides comprising the amino acid sequence of any of SEQ ID NO 1, 2, 14, and/or 15.

In some embodiments, the composition comprises a nucleic acid encoding a GDF11 polypeptide.

In some embodiments, the composition is administered via a route selected from the group consisting of: intravenously; subcutaneously; intra-arterial; and intra-coronary arterial. In some embodiments, the level of GDF11 is increased by at least 100%. In some embodiments, the level of GDF11 is increased to at least 75% of a healthy reference level.

In one aspect, the technology described herein relates to a pharmaceutical composition comprising an isolated GDF11 polypeptide and a pharmaceutically acceptable carrier.

In one aspect, the technology described herein relates to the use of a GDF11 polypeptide for the treatment of a condition selected from the group consisting of: diastolic heart failure; cardiac hypertrophy; hypertension; valvular disease; aortic stenosis; genetic hypertrophic cardiomyopathy; or stiffness of the heart due to aging.

BRIEF DESCRIPTION OF THE DRAWINGS

FIG. 1A depicts a schematic of the experiment. Six pairs of young isochronic, heterochronic and old isochronic parabiotic mice were generated. Four weeks after surgery mice were sacrificed and tissues harvested for analysis. FIG. 1B demonstrates a dramatic reduction in heart size in old mice exposed to a young circulation for 4 weeks. In heterochronic parabionts, the hypertrophy of the older heart appears to regress, while the younger parabiont heart does not develop hypertrophy. FIG. 1C depicts a graph representing the heart weight:tibia length ratio after 4 weeks of parabiosis, Data shown as mean±s.e.m.

FIG. 2A depicts myocyte cross-sectional area in LV based on PAS staining in females. For each animal, myocyte size was determined from cross-sectional area measurements of 100-200 myocytes in 5 independent myocardial sections. Results are based on the average from 4 to 12 animals per group. FIG. 2B depicts the results when the experiment was performed using male mice. Data shown as mean±s.e.m.

FIGS. 3A-3C demonstrate that the reversal of cardiac hypertrophy in old mice exposed to a young circulation is not explained by a reduction in blood pressure in old heterochronic parabiotic mice. FIG. 3A depicts measurements of blood pressure and pulse. Systolic blood pressure was measured on unoperated young and old mice at baseline using a computerized tail-cuff system. Pulse rate was measured using the same system. Young (2 months) mice show a significantly higher systolic blood pressure when compared to old (21 months) mice with no difference in pulse rate. FIG. 2B depicts the results when using a tail-cuff system modified to hold parabiotic pairs to measure blood pressure simultaneously at 4, 7 and 10 weeks after mice were conjoined. Old heterochronic mice showed a significant increase in systolic blood pressure at 7 and 10 weeks; old isochronic mice had a significant increase in blood pressure at 7 weeks when compared to baseline values, *: P<0.05. FIG. 3C depicts the values obtained for mean arterial pressure when determined by performing terminal intra-arterial catheterizations obtained simultaneously on paired mice after they had been conjoined for 10 wks. No significant differences were observed between the different groups. Data shown as mean±s.e.m.

FIGS. 4A-4C depict molecular evidence for cardiac remodeling of aged myocardium by a young systemic circulation. RNA was extracted from hearts and analyzed by real-time PCR. ANP (FIG. 4A) and BNP (FIG. 4B) levels were significantly reduced in old mice exposed to a young circulation when compared to the old isochronic mice. FIG. 4C depicts a graph demonstrating that SERCA-2 transcript levels were significantly higher in old mice exposed to a young circulation when compared to old isochronic mice. Transcript levels measured with real-time PCR and normalized to the Y-IP group. Data shown as mean±s.e.m.

FIG. 6A presents a schematic of the experiment, wherein young isochronic, heterochronic, and old isochronic parabiotic mice were generated. Ten weeks after surgery mice were sacrificed and tissues harvested for analysis. FIG. 6B depicts a graph representing the heart weight:tibia length ratio after 10 weeks of parabiosis, Data shown as mean±SEM FIGS. 7A-7B demonstrate that young mice have a higher level of GDF11 than older mice. FIG. 7A depicts the results of an ELISA assay while

FIG. 8 depicts an alignment of human GDF11 precursor polypeptide (query sequence; residues 62-407 of SEQ ID NO: 1) and human GDF8 precursor polypeptide (subject sequence; SEQ ID NO: 18).

FIG. 9 depicts an alignment of human GDF11 precursor peptide (query sequence; residues 47-407 of SEQ ID NO:1) and murine GDF11 precursor peptide (subject sequence; SEQ ID NO: 19).

FIG. 10A depicts a graph representing the heart weight/tibia length ratio after 4 weeks of parabiosis, using only CD45.2 mice. FIG. 10B depicts a graph of left ventricular myocyte cross-sectional area based on PAS staining in CD45.2 mice. Exposure of an old mouse to the circulation of a young CD45.2 mouse reverses cardiac hypertrophy. FIG. 10C depicts a graph demonstrating that old mice conjoined to young CD45.1 or CD45.2 mice show no difference in blood pressure measured by the tail-cuff system after 4 weeks. FIG. 10D depicts a graph demonstrating that no significant intergroup differences in blood pressure were detected with terminal intra-arterial catheter-based measurements. Data shown as mean±s.e.m.

FIG. 11A depicts flow cytometry plots depicting CD45.1 (y-axis) or CD45.2 expression (x-axis) by splenocytes isolated from young or old mice joined by sham heterochronic parabiosis. Sham parabiotic pairs showed no cross-circulation of partner-derived blood cells as is observed in experimental parabiosis. FIG. 11B depicts a graph representing the heart weight/tibia length ratio after 4 weeks of sham parabiosis. FIG. 11C depicts a graph of left ventricular myocyte cross-sectional area based on PAS staining after 4 weeks of sham parabiosis. Data shown as mean±s.e.m.

FIGS. 12A-12F demonstrate that circulating levels of GDF11 are reduced in aged mice and restoring GDF11 to "youthful" levels promotes reversal of cardiac hypertrophy and molecular remodeling. FIG. 12A depicts the results of Western Blot analysis demonstrating reduced levels of GDF11 in the plasma of old mice compared to young mice (n=3 per group). Similarly GDF11 is reduced in the plasma of old isochronic (O-IP) compared to young isochronic (Y-IP) mice and is restored to "youthful" levels in old mice after exposure to a young circulation (O-HP) (n=3 per group). FIG. 12B depicts a graph of phenylephrine-induced cardiac hypertrophy measured by $^3$H-leucine incorporation in cardiac myocytes exposed to rGDF11 or myostatin. rGDF11 (50 nM) prevented phenylephrine-induced $^3$H-leucine incorporation. FIG. 12C demonstrates that GDF11 signals through a TGFβ pathway and suppresses Forkhead transcription factor phosphorylation in human cardiomyocytes. Western blots of human induced pluripotent stem cell-derived cardiomyocytes stimulated for 15 min with serum free media (Control) or with the same media containing the indicated proteins. FIG. 12D depicts a graph of randomized, vehicle controlled study of rGDF11 therapy in aged (23 mos) mice. rGDF11 (0.1 mg/kg) or saline (vehicle control) administered by daily intraperitoneal injection for 30 d. Graph representing heart weight/tibia length ratio. FIG. 12E depicts a graph of left ventricular myocyte cross-sectional area measured after PAS staining. rGDF11 therapy leads to a reduction in myocyte cross sectional area. FIG. 12F depicts graphs of expression of ANP, BNP or SERCA-2 in hearts harvested from old mice treated with rGDF11 or saline. Real-time PCR transcript measurements are normalized to levels in the saline group. Data shown as mean±s.e.m.

FIG. 13A depicts a graph of expression of GDF11 in tissues harvested from young (3 months old) mice. Real-time PCR transcript measurements are normalized to levels in the liver. The gene expression in the spleen was significantly higher (* P<0.05) when compared with all the other tissues. FIG. 13B depicts a graph of expression of GDF11 in the spleen harvested from young (3 months old) and old (24 months old) mice. Real-time PCR transcript measurements are normalized to levels in young mice. FIG. 13C depicts a graph of Western blot analysis of GDF11 in the spleen from young and old mice. Densitometry (arbitrary units, mean±s.e.m) of GDF11 normalized to α-tubulin. Data shown as mean±s.e.m.

FIG. 14 demonstrates that GDF11 levels can be persistently increased for 24 hours in plasma after a single intraperitoneal bolus. GDF11 levels in plasma were evaluated by Western analysis at the indicated times after a single intraperitoneal injection of 0.1 mg/kg of recombinant GDF11 (n=3).

FIGS. 15A-15C demonstrate that supplementation of rGDF11 did not prevent development of cardiac hypertrophy after pressure overload by transverse aortic constriction in young mice. FIG. 15A depicts a graph representing the heart weight/tibia length ratio after 30 days of treatment with rGDF11 or vehicle. The ratio in mice that were injected with rGDF11 (n=10) was not significantly different than the ratio measured in mice that were injected with vehicle (n=9) (9.08+/−0.71 vs. 9.89+/−0.69 mm/mg, P=ns). FIG. 15B depicts a graph of left ventricular myocyte cross-sectional area measured after PAS staining after 30 days of treatment with rGDF11 or vehicle. Cardiomyocyte cross sectional area was not significantly different in the two groups ((286.4±12.89 µm2 in rGDF11 treated, 304.2±17.3 µm2 in vehicle treated, P=ns). FIG. 15C depicts a table with echocardiographic data after 30 days of treatment with rGDF11 or vehicle. No significant differences were noted in echocardiographic parameters of ventricular remodeling or function. AWT=anterior wall thickness; PWT=posterior wall thickness; EDD=end diastolic dimension; ESD=end systolic dimension; FS=fractional shortening. Data shown as mean±s.e.m.

DETAILED DESCRIPTION

Figure 1A:
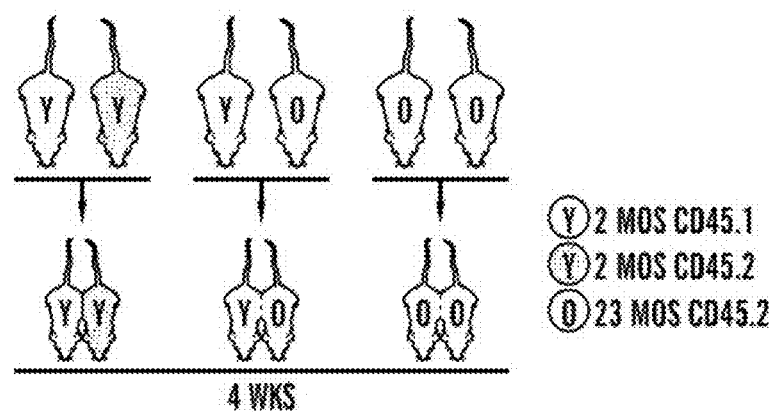
FIGS. 1A-1C demonstrate that heterochronic parabiosis reverses age-related cardiac hypertrophy.

Embodiments of the technology described herein are based on the discovery that as animals age, their level of GDF11 polypeptide decreases and results in cardiac hypertrophy. Described herein are methods and compositions for the treatment of cardiac conditions including, but not limited to diastolic heart failure; cardiac hypertrophy; age-related cardiac hypertrophy; hypertension; valvular disease; aortic stenosis; genetic hypertrophic cardiomyopathy; and/or stiffness of the heart due to aging. These methods and compositions relate generally to increasing the level of GDF11 polypeptide in a subject in order to treat, prevent, or reverse the cardiac conditions described herein.

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

As used herein, the term "cardiovascular condition" refers to a condition mediated or characterized by a reduction in circulating GDF11 polypeptide. Non-limiting examples of cardiovascular conditions include diastolic heart failure; cardiac hypertrophy; hypertension; valvular disease; aortic stenosis; genetic hypertrophic cardiomyopathy; or stiffness of the heart due to aging.

The terms "decrease," "reduce," "reduced", "reduction", "decrease," and "inhibit" are all used herein generally to mean a decrease by a statistically significant amount relative to a reference. However, for avoidance of doubt, "reduce," "reduction" or "decrease" or "inhibit" typically means a decrease by at least 10% as compared to a reference level and can include, for example, a decrease by at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, up to and including, for example, the complete absence of the given entity or parameter as compared to the reference level, or any decrease between 10-99% as compared to the absence of a given treatment.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90%, or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or more as compared to a reference level.

The term "isolated" or "partially purified" as used herein refers, in the case of a nucleic acid or polypeptide, to a nucleic acid or polypeptide separated from at least one other component (e.g., nucleic acid or polypeptide) that is present with the nucleic acid or polypeptide as found in its natural source and/or that would be present with the nucleic acid or polypeptide when expressed by a cell, or secreted in the case of secreted polypeptides. A chemically synthesized nucleic acid or polypeptide or one synthesized using in vitro transcription/translation is considered "isolated."

The term "biological sample" as used herein denotes a sample taken or isolated from a biological organism, e.g., cardiac biopsy sample, blood sample, cell lysate, a homogenate of a tissue sample from a subject, or a fluid sample from a subject. Exemplary biological samples include, but are not limited to, cardiac tissue biopsies or blood and/or serum samples. In some embodiments, the sample is from a resection, biopsy, or core needle biopsy. In addition, fine needle aspirate samples can be used. Samples can include paraffin-embedded and frozen tissue. The term "biological sample" also includes untreated or pretreated (or pre-processed) biological samples. In some embodiments, the biological sample is an untreated biological sample. The sample can be obtained by removing a sample of cells from a subject, but can also be accomplished by using previously isolated cells (e.g. isolated at a prior timepoint and isolated by the same or another person.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "patient", "individual" and "subject" are used interchangeably herein.

Preferably, the subject is a mammal. The mammal can be a human, non-human primate, mouse, rat, dog, cat, horse, or cow, but are not limited to these examples. Mammals other than humans can be advantageously used, for example, as subjects that represent animal models of, for example, cardiac hypertrophy. In addition, the methods described herein can be used to treat domesticated animals and/or pets. A subject can be male or female.

A subject can be one who has been previously diagnosed with or identified as suffering from or having a condition in need of treatment (e.g. cardiac hypertrophy) or one or more complications related to such a condition, and optionally, but need not have already undergone treatment for a condition or the one or more complications related to the condition. Alternatively, a subject can also be one who has not been previously diagnosed as having a condition in need of treatment or one or more complications related to such a condition. Rather, a subject can include one who exhibits one or more risk factors for a condition or one or more complications related to a condition. A "subject in need" of treatment for a particular condition can be a subject having that condition, diagnosed as having that condition, or at increased risk of developing that condition relative to a given reference population.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Other than in the operating examples, or where otherwise indicated, all numbers expressing quantities of ingredients or reaction conditions used herein should be understood as modified in all instances by the term "about." The term "about" when used in connection with percentages can mean±1%.

The term "statistically significant" or "significantly" refers to statistical significance and generally means a two standard deviation (2SD) difference, above or below a reference value. Additional definitions are provided in the text of individual sections below.

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); The ELISA guidebook (Methods in molecular biology 149) by Crowther J. R. (2000); Immunology by Werner Luttmann, published by Elsevier, 2006. Definitions of common terms in molecular biology can also be found in Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001) and Davis et al., Basic Methods in Molecular Biology, Elsevier Science Publishing, Inc., New York, USA (1995) which are both incorporated by reference herein in their entireties.

Described herein are methods comprising administering to a subject a composition which increases the level of GDF11 polypeptide in the subject. In some embodiments, the subject is one who has, or has been diagnosed as having an age-related condition. As used herein, the term "age-related condition" refers to any disease, disorder, or undesirable state whose incidence in a population or severity in an individual correlates with the progression of age. In some embodiments, the age-related condition is a cardiovascular condition; aging of the heart; aging of skeletal muscle; or aging of the brain. Aging of any given organ can include, but is not limited to, reduced cellularity, reduced stem cell genomic integrity, reduced cellular function (e.g. reduced muscle contraction in muscle tissue), reduced regenerative capacity, atrophy (e.g. aging of the skin can include atrophy of the epidermis and/or sebaceous follicles). An age-related condition can be one that reduces the function of a given organ or one that is aesthetically undesirable (e.g. aging of the skin or muscle can be aesthetically undesirable). Additional age-related conditions can include, but are not limited to: sarcopenia, skin atrophy, muscle wasting, brain atrophy, atherosclerosis, arteriosclerosis, pulmonary emphysema, osteoporosis, osteoarthritis, immunologic incompetence, high blood pressure, dementia, Huntington's disease, Alzheimer's disease, cataracts, age-related macular degeneration, prostate cancer, stroke, diminished life expectancy, memory loss, wrinkles, impaired kidney function, and age-related hearing loss. "Metabolic disorder", as used herein, shall mean any disease or disorder that damages or interferes with normal function in a cell, tissue, or organ by affecting the production of energy in cells or the accumulation of toxins in a cell, tissue, organ, or individual. Metabolic disorders relevant to the present invention include, but are not limited to, Type II Diabetes, Metabolic Syndrome, hyperglycemia, and obesity.

In some embodiments, the composition which increases the level of GDF11 polypeptide is administered to a subject who has or has been diagnosed with diastolic heart failure, cardiac hypertrophy, age-related cardiac hypertrophy, hypertension, valvular disease, aortic stenosis, genetic hypertrophic cardiomyopathy, and/or stiffness of the heart due to aging.

In some embodiments, the level of GDF11 polypeptide is the level of GDF11 in the circulation of a subject. In some embodiments, the level of GDF11 polypeptide is the level of GDF11 in the cardiac tissue of a subject. In some embodiments, the level of GDF11 polypeptide is determined by measuring the level of an mRNA encoding a GDF11 polypeptide. The level of GDF11 in a subject can be determined by obtaining a biological sample from the subject and determining the level of GDF11 in the biological sample. Methods for determining the level of a polypeptide in a subject or a sample obtained from a subject are well known in the art and include, but are not limited to, ELISA, radioimmunoassay, immunohistochemistry, methods involving a labeled antibody specific, for GDF11, dot blot analysis, Northern blot, in-situ hybridization, and RT-PCR, among others. Antibodies specific for GDF11 are commercially available, e.g. Cat. No. ab71347 from Abeam; Cambridge, Mass. In some embodiments, the level of GDF11 can be measured as described in Souza et al., Molecular Endocrinology 2008 22:2689-2702; which is incorporated by reference herein in its entirety.

As animals age, cardiac tissues often experience a decrease in diastolic function related to a thickening and/or stiffening of the tissue or cardiac hypertrophy. As used herein, the term "cardiac hypertrophy" refers to an enlargement of the heart due in part to an increase in the sire of the myocytes. In some embodiments, the myocytes respond to stress through hypertrophic growth. Cardiac hypertrophy is often associated with increased risk of morbidity and mortality. In some embodiments, the cardiac hypertrophy is left ventricle cardiac hypertrophy. The term "left ventricle cardiac hypertrophy" refers to a disorder in which the myocardial tissue of the left ventricle of the heart thickens. Without wishing to be bound by theory, causes of left ventricle cardiac hypertrophy include, for example, hypertension (e.g., high blood pressure), stenosis of the aortic valve (e.g., the inability of the heart valve to fully open), and hypertrophic cardiomyopathy (e.g., a disorder in which the myocardial tissue thickens for no obvious cause). In other embodiments, the cardiac hypertrophy is right ventricle cardiac hypertrophy. The term "right ventricle cardiac hypertrophy" refers to a disorder in which the myocardial tissue of the right ventricle thickens. Without wishing to be bound by theory, causes of right ventricle hypertrophy include, for example, diseases that damage the lungs, such as emphysema and cystic fibrosis; conditions that decrease oxygen levels in the body, such as chronic bronchitis and sleep apnea; stenosis of the pulmonic heart valve, chronic pulmonary embolism, primary pulmonary hypertension, asymmetric septal hypertrophy, and idiopathic hypertrophic subaortic stenosis.

Symptoms of cardiac hypertrophy and methods of measuring them are well known in the art and include but are not limited to, an increase in left ventricular mass; a change in body weight ratio; changes in cardiomyocyte size, mass, and organization; changes in cardiac gene expression; changes in cardiac function (e.g. diastolic heart function); fibroid deposition; changes in dP/dT, i.e., the rate of change of the ventricular pressure with respect to time; calcium ion flux; stroke length; and ventricular output. Diagnostic procedures useful in detecting cardiovascular conditions and/or efficacy of treatment of cardiovascular conditions include echocardiography (e.g. 2 and 3 dimensional), MRI (e.g. spin-echo MRI or cine magnetic resonance angiography), chest radiography, thallium-201 myocardial imaging. PET, ECG-gated CT, cardiac catheterization, angiography, electrophysiological studies, and magnetic resonance spectroscopy. For example, echocardiography can detect the size of the heart, the pattern of hypertrophy, the contractile function of the heart, and the severity of the outflow gradient while MRI can evaluate ventricular anatomy, wall thickness, ventricular function, ventricular end-diastolic and end-systolic volumes, valvular dysfunction, and outflow tract obstruction.

The methods and compositions described herein relate to increasing the level of GDF11 polypeptide in a subject. As used herein, "GDF11" refers to "Growth and Differentiation Factor 11" (NCBI Gene ID No: 10220), a member of the Transforming Growth Factor-beta superfamily of growth factors. GDF11 is known to bind TGFβ superfamily type I receptors including ALK4, ALK5, and ALK7. For signaling in mammalian development, GDF11 predominantly uses ALK4 and ALK5. In some embodiments, GDF11 signaling can also occur via the ACVR2B receptor. GDF11 is also closely related to GDF8 (also known as myostatin). GDF11 can also be referred to as bone morphogenic protein 11, i.e. BMP11. As used herein, "GDF11" can include the human precursor polypeptide (SEQ ID NO: 1, NCBI Ref Seq: NP_005802); the human pro-peptide (SEQ ID NO: 2); the human N-terminal polypeptide (SEQ ID NO: 15), and the human mature (SEQ ID NO:14) forms of GDF11 as well as homologs from other species, including but not limited to bovine, dog, cat chicken, murine, rat, porcine, ovine, turkey, horse, fish, baboon and other primates. The terms also refer to fragments or variants of GDF11 that maintain at least 50% of the cardiac hypertrophy-reducing (or prevention) effect of the full length GDF11 of SEQ ID NO: 2, SEQ ID NO: 1, or SEQ ID NO: 14, e.g. as measured in an appropriate animal model. Conservative substitution variants that maintain cardiac hypertrophy-reducing or preventing activity of wild-type GDF11 will include a conservative substitution as defined herein. The identification of amino acids most likely to be tolerant of conservative substitution while maintaining at least 50% of the activity of the wildtype is guided by, for example, sequence alignment with GDF11 homologs or paralogs from other species. Amino acids that are identical between GDF11 homologs are less likely to tolerate change, while those showing conservative differences are obviously much more likely to tolerate conservative change in the context of an artificial variant. Similarly, positions with non-conservative differences are less likely to be critical to function and more likely to tolerate conservative substitution in an artificial variant. Variants can be tested for activity, for example, by administering the variant to an appropriate animal model with cardiac hypertrophy and imaging as described herein to follow any reversion of the hypertrophy.

For human GDF11, the pro-peptide plus signal sequence (e.g. the precursor polypeptide) is 407 amino acids long. Cleavage of the 24 amino acid signal peptide generates a pro-peptide of 383 amino acids and cleavage of the pro-peptide results in a mature GDF11 polypeptide of 109 amino acids that corresponds to the C-terminal 109 amino acids of the pro-peptide. The mature polypeptide forms a disulfide-linked homodimer. Cleavage of the pro-peptide also generates the N-terminal polypeptide (e.g. SEQ ID NO: 15) comprising amino adds 25-298 of SEQ ID NO: 1. The N-terminal GDF11 polypeptide can antagonize the activity of, e.g. the polypeptides of SEQ ID NOs: 2 and 14, at least in vitro by forming a complex with the other forms of GDF11 polypeptides and can thus be used to modulate the activity of GDF11 compositions as described herein. Thus, to the extent that GDF11 polypeptides as described herein reduce or prevent cardiac conditions, e.g., cardiac hypertrophy or stiffening among others, and to the extent the N-terminal GDF11 polypeptide of, e.g., SEQ ID NO: 15, can antagonize such reduction or prevention, the polypeptide of SEQ ID NO: 15 can be excluded from the meaning of "GDF11 polypeptide" as that term is used herein.

As used herein, the terms "proteins" and "polypeptides" are used interchangeably to designate a series of amino acid residues connected to the other by peptide bonds between the alpha-amino and carboxy groups of adjacent residues. The terms "protein", and "polypeptide" refer to a polymer of protein amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing. As used herein, "pro-peptide" used in reference to GDF11 refers to a GDF11 polypeptide in which the signal domain (e.g. amino acids 1-24 of SEQ ID NO:1) which has been cleaved off during formation of the mature and/or active forms of GDF11. As used herein, "precursor peptide" used in reference to GDF11 refers to a GDF11 polypeptide comprising the signal domain, e.g. a polypeptide comprising the amino acid sequence of SEQ ID NO: 1.

In some embodiments, the level of GDF11 in a subject is increased by administering a composition comprising a GDF11 polypeptide and/or a nucleic acid encoding a GDF11 polypeptide. A GDF11 polypeptide administered to a subject according to the methods described herein can comprise a GDF11 polypeptide as described herein above, e.g. a pro-peptide or mature form. In some embodiments, the GDF11 polypeptide comprises the amino acid sequence of SEQ ID NO: 1. In some embodiments, the GDF11 polypeptide comprises the amino acid sequence of SEQ ID NO: 2. In some embodiments, the GDF11 polypeptide comprises the amino acid sequence of SEQ ID NO: 14. In some embodiments, the GDF11 polypeptide comprises the amino acid sequence of SEQ ID NO: 15. In some embodiments, the composition administered to the subject can comprise GDF11 polypeptide homodimers comprising polypeptides of the amino acid sequence of SEQ ID NO: 14. In some embodiments, the composition administered to the subject can comprise GDF11 polypeptide homodimers comprising polypeptides of the amino acid sequence of SEQ ID NO: 15. In some embodiments, the composition administered to the subject can comprise GDF11 polypeptide homodimers comprising polypeptides of the amino acid sequence of SEQ ID NO: 2. In some embodiments, the composition administered to the subject can comprise GDF11 polypeptide homodimers comprising polypeptides of the amino acid sequence of SEQ ID NO: 1. In some embodiments, the composition administered to the subject can comprise GDF11 polypeptide heterodimers comprising polypeptides of any of the amino acid sequence of SEQ ID NO: 15, SEQ ID NO: 14, SEQ ID NO: 2, and/or SEQ ID NO: 1. In some embodiments, a variant or fragment of a GDF11 polypeptide can be administered to a subject. In some embodiments, the variant of GDF11 is a conservatively modified variant.

In some embodiments of any of the aspects described herein, the subject can be administered a variant or fragment (e.g. a conservatively modified variant or a functional fragment or a nucleic acid encoding such a polypeptide) of a polypeptide selected from Collectin kidney 1 (e.g. NCBI Gene ID No: 78989) (SEQ ID NO: 4), Cathespin D (e.g. NCBI Gene ID No: 1509) (SEQ ID NO: 5), Dickkopf-related protein 4 (e.g. NCBI Gene ID No: 27121) (SEQ ID NO: 6), Erythrocyte membrane protein 4.1 (e.g. NCBI Gene ID No: 2035) (SEQ ID NO: 7), esterase D (e.g. NCBI Gene ID No: 2098) (SEQ ID NO: 8), hemoglobin (e.g. NCBI Gene ID No: 3043 or 3047) (SEQ ID NOS 9 and 20, respectively), interleukin-1 receptor accessory protein (e.g. NCBI Gene ID No: 3556) (SEQ ID NO: 21), natural killer group 2 member D (e.g. NCBI Gene ID No: 22914) (SEQ ID NO: 22), Ras-related C3 botulinum toxin substrate 1 (e.g. NCBI Gene ID No: 5879) (SEQ ID NO: 23), GTP-binding nuclear protein Ran (e.g. NCBI Gene ID No: 5901) (SEQ ID NO: 24), tissue inhibitor of metalloproteases 3 (e.g. NCBI Gene ID No: 7078) (SEQ ID NO: 25), and thymidylate synthase (e.g. NCBI Gene ID No: 7298) (SEQ ID NO: 26).

In some embodiments, the GDF11 polypeptide can be a variant of a sequence described herein, e.g. a variant of a GDF11 polypeptide comprising the amino acid sequence of SEQ ID NO: 15, SEQ ID NO: 14, SEQ ID NO: 1, or SEQ ID NO: 2. In some embodiments, the variant is a conservative substitution variant. Variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Polypeptide-encoding DNA sequences encompass sequences that comprise one or more additions, deletions, or substitutions of nucleotides when compared to a native or reference DNA sequence, but that encode a variant protein or fragment thereof that retains the relevant biological activity relative to the reference protein, i.e., can slow or reverse cardiac hypertrophy at least 50% as well as wildtype GDF11. As to amino acid sequences, one of skill will recognize that individual substitutions, deletions or additions to a nucleic acid, peptide, polypeptide, or protein sequence which alters a single amino acid or a small percentage, (i.e. 5% or fewer, e.g. 4% or fewer, or 3% or fewer, or 1% or fewer) of amino acids in the encoded sequence is a "conservatively modified variant" where the alteration results in the substitution of an amino acid with a chemically similar amino acid. It is contemplated that some changes can potentially improve the relevant activity, such that a variant, whether conservative or note, has more than 100% of the activity of wildtype GDF11, e.g. 110%, 125%, 150%, 175%, 200%, 500%, 1000% or more.

One method of identifying amino acid residues which can be substituted is to align, for example, human GDF11 to a GDF11 homolog from one or more non-human species. Alignment can provide guidance regarding not only residues likely to be necessary for function but also, conversely, those residues likely to tolerate change. Where, for example, an alignment shows two identical or similar amino acids at corresponding positions, it is more likely that that site is important functionally. Where, conversely, alignment shows residues in corresponding positions to differ significantly in size, charge, hydrophobicity, etc., it is more likely that that site can tolerate variation in a functional polypeptide. Similarly, alignment with a related polypeptide from the same species, e.g. GDF8, which does not show the same activity, can also provide guidance with respect to regions or structures required for GDF11 activity. FIG. 8 depicts an example of an alignment between human GDF11 precursor peptide (query sequence; residues 62-407 of SEQ ID NO:1) and human GDF8 precursor peptide created using the default settings of the alignment tool of the BLASTP program, freely available on the world wide web at http://blast.ncbi.nlm.nih.gov/. FIG. 9 depicts an example of an alignment between human GDF11 precursor peptide (query sequence; residues 47-407 of SEQ ID NO:1) and murine GDF11 precursor peptide created using the default settings of the alignment tool of the BLASTP program, freely available on the world wide web at http://blast.ncbi.nlm.nih.gov/. The variant amino acid or DNA sequence can be at least 90%, at least 95%, at least 96%, at least 97%, at least 98%, at least 99%, or more, identical to a native or reference sequence, e.g. SEQ ID NO: 15, SEQ ID NO: 14, SEQ ID NO:1, or SEQ ID NO: 2 or a nucleic acid encoding one of those amino acid sequences. The degree of homology (percent identity) between a native and a mutant sequence can be determined, for example, by comparing the two sequences using freely available computer programs commonly employed for this purpose on the world wide web. The variant amino acid or DNA sequence can be at least 90%, at least 91%, at least 92%, at least 93%, at least 94%, at least 95%, at least 96%, at least 97%, at least 98%, at least 99%, or more, similar to the sequence from which it is derived (referred to herein as an "original" sequence). The degree of similarity (percent similarity) between an original and a mutant sequence can be determined, for example, by using a similarity matrix. Similarity matrices are well known in the art and a number of tools for comparing two sequences using similarity matrices are freely available online, e.g. BLASTp (available on the world wide web at http://blast.ncbi.nlm.nih.gov), with default parameters set.

It is noted that the mature GDF11 polypeptide includes likely intrachain disulfide bonds between, e.g. amino acid 313 and 372; 341 and 404; and 345 and 406 (numbered relative to the full length polypeptide, including the signal sequence) and that amino acid 371 likely participates in interchain disulfide bonding.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired apoptotic activity of a native or reference polypeptide is retained. Conservative substitution tables providing functionally similar amino acids are well known in the art. Such conservatively modified variants are in addition to and do not exclude polymorphic variants, interspecies homologs, and alleles consistent with the disclosure. Typically conservative substitutions for one another include: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

In some embodiments, the GDF11 polypeptide administered to a subject can comprise one or more amino acid substitutions or modifications. In some embodiments, the substitutions and/or modifications can prevent or reduce proteolytic degradation and/or prolong half-life of the polypeptide in the subject. In some embodiments, a GDF11 polypeptide can be modified by conjugating or fusing it to other polypeptide or polypeptide domains such as, by way of non-limiting example, transferrin (WO06096515A2), albumin (Yeh et al., 1992), growth hormone (US2003104578AA); cellulose (Levy and Shoseyov, 2002); and/or Fc fragments (Ashkenazi and Chamow, 1997). The references in the foregoing paragraph are incorporated by reference herein in their entireties.

In some embodiments, a GDF11 polypeptide as described herein can comprise at least one peptide bond replacement. A single peptide bond or multiple peptide bonds, e.g. 2 bonds, 3 bonds, 4 bonds, 5 bonds, or 6 or more bonds, or all the peptide bonds can be replaced. An isolated peptide as described herein can comprise one type of peptide bond replacement or multiple types of peptide bond replacements, e.g. 2 types, 3 types, 4 types, 5 types, or more types of peptide bond replacements. Non-limiting examples of peptide bond replacements include urea, thiourea, carbamate, sulfonyl urea, trifluoroethylamine, ortho-(aminoalkyl)-phenylacetic acid, para-(aminoalkyl)-phenylacetic acid, meta-(aminoalkyl)-phenylacetic acid, thioamide, tetrazole, boronic ester, olefinic group, and derivatives thereof.

In some embodiments, a GDF11 polypeptide as described herein can comprise naturally occurring amino acids commonly found in polypeptides and/or proteins produced by living organisms, e.g. Ala (A), Val (V), Leu (L), Ile (I), Pro (P), Phe (F), Trp (W), Met (M), Gly (G), Ser (S), Thr (T), Cys (C), Tyr (Y), Asn (N), Gln (O), Asp (D), Glu (E), Lys (K), Arg (R), and His (H). In some embodiments, a GDF11 polypeptide as described herein can comprise alternative amino acids. Non-limiting examples of alternative amino acids include, D-amino acids; beta-amino acids; homocysteine, phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine (3-mercapto-D-valine), ornithine, citruline, alpha-methyl-alanine, para-benzoylphenylalanine, para-amino phenylalanine, p-fluorophenylalanine, phenylglycine, propargylglycine, sarcosine, and tert-butylglycine), diaminobutyric acid, 7-hydroxy-tetrahydroisoquinoline carboxylic acid, naphthylalanine, biphenylalanine, cyclohexylalanine, amino-isobutyric acid, norvaline, norleucine, tert-leucine, tetrahydroisoquinoline carboxylic acid, pipecolic acid, phenylglycine, homophenylalanine, cyclohexylglycine, dehydroleucine, 2,2-diethylglycine, 1-amino-1-cyclopentanecarboxylic acid, 1-amino-1-cyclohexanecarboxylic acid, amino-benzoic acid, amino-naphthoic acid, gamma-aminobutyric acid, difluorophenylalanine, nipecotic acid, alpha-amino butyric acid, thienyl-alanine, t-butylglycine, trifluorovaline; hexafluoroleucine; fluorinated analogs; azide-modified amino acids; alkyne-modified amino acids; cyano-modified amino acids; and derivatives thereof.

In some embodiments, a GDF11 polypeptide can be modified, e.g. by addition of a moiety to one or more of the amino acids comprising the peptide. In some embodiments, a GDF11 polypeptide as described herein can comprise one or more moiety molecules, e.g. 1 or more moiety molecules per peptide, 2 or more moiety molecules per peptide, 5 or more moiety molecules per peptide, 10 or more moiety molecules per peptide or more moiety molecules per peptide. In some embodiments, a GDF11 polypeptide as described herein can comprise one more types of modifications and/or moieties, e.g. 1 type of modification, 2 types of modifications, 3 types of modifications or more types of modifications. Non-limiting examples of modifications and/or moieties include PEGylation; glycosylation; HESylation; ELPylation; lipidation; acetylation; amidation; end-capping modifications; cyano groups; phosphorylation; albumin, and cyclization. In some embodiments, an end-capping modification can comprise acetylation at the N-terminus, N-terminal acylation, and N-terminal formylation. In some embodiments, an end-capping modification can comprise amidation at the C-terminus, introduction of C-terminal alcohol, aldehyde, ester, and thioester moieties. The half-life of a GDF11 polypeptide can be increased by the addition of moieties, e.g. PEG or albumin.

In some embodiments, the GDF11 polypeptide administered to the subject can be a functional fragment of one of the GDF11 amino acid sequences described herein. As used herein, a "functional fragment" is a fragment or segment of a peptide which can slow or reverse cardiac hypertrophy in a subject according to the assays described below herein. A functional fragment can comprise conservative substitutions of the sequences disclosed herein. In some embodiments, a functional fragment can comprise the 12.5 kDa C-terminus of GDF11. In some embodiments, the 12.5 kDa C-terminus of GDF11 can function as a monomer. In some embodiments, the 12.5 kDa C-terminus of GDF11 can function as a homodimer. In some embodiments, the 12.5 kDa C-terminus of GDF11 can function as a heterodimer with the GDF11 pro-peptide.

Alterations of the original amino acid sequence can be accomplished by any of a number of techniques known to one of skill in the art. Mutations can be introduced, for example, at particular loci by synthesizing oligonucleotides containing a mutant sequence, flanked by restriction sites permitting ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations include those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are herein incorporated by reference in their entireties. In some embodiments, a GDF11 polypeptide as described herein can be chemically synthesized and mutations can be incorporated as part of the chemical synthesis process.

In some embodiments, a GDF11 polypeptide as described herein can be formulated as a pharmaceutically acceptable prodrug. As used herein, a "prodrug" refers to compounds that can be converted via some chemical or physiological process (e.g., enzymatic processes and metabolic hydrolysis) to a therapeutic agent. Thus, the term "prodrug" also refers to a precursor of a biologically active compound that is pharmaceutically acceptable. A prodrug may be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. See Harper, "Drug Latentiation" in Jucker, ed. *Progress in Drug Research* 4:221-294 (1962); Morozowich et al, "Application of Physical Organic Principles to Prodrug Design" in E. B. Roche ed. *Design of Biopharmaceutical Properties through Prodrugs and Analogs*, APHA Acad. Pharm. Sci. 40 (1977); *Bioreversible Carriers in Drug in Drug Design, Theory and Application*, E. B. Roche, ed., APHA Acad. Pharm. Sci. (1987); *Design of Prodrugs*, H. Bundgaard, Elsevier (1985); Wang et al. "Prodrug approaches to the improved delivery of peptide drug" in *Curr. Pharm. Design.* 5(4):265-287 (1999); Pauletti et al. (1997) Improvement in peptide bioavailability: Peptidomimetics and Prodrug Strategies, *Adv. Drug. Delivery Rev.* 27:235-256; Mizen et al. (1998) "The Use of Esters as Prodrugs for Oral Delivery of (3-Lactam antibiotics," *Pharm. Biotech.* 11:345-365; Gaignault et al. (1996) "Designing Prodrugs and Bioprecursors I. Carrier Prodrugs," *Pract. Med. Chem.* 671-696; Asgharnejad, "Improving Oral Drug Transport", in *Transport Processes in Pharmaceutical Systems*, G. L. Amidon, P. I. Lee and E. M. Topp, Eds., Marcell Dekker, p. 185-218 (2000); Balant et al., "Prodrugs for the improvement of drug absorption via different routes of administration", *Eur. J. Drug Metab. Pharmacokinet.*, 15(2): 143-53 (1990); Balimane and Sinko, "Involvement of multiple transporters in the oral absorption of nucleoside analogues", *Adv. Drug Delivery Rev.*, 39(1-3): 183-209 (1999); Browne, "Fosphenyloin (Cerebyx)", *Clin. Neuropharmacol.* 20(1): 1-12 (1997); Bundgaard, "Bioreversible derivatization of drugs—principle and applicability to improve the therapeutic effects of drugs", *Arch. Pharm. Chemi* 86(1): 1-39 (1979); Bundgaard H. "Improved drug delivery by the prodrug approach", *Controlled Drug Delivery* 17: 179-96 (1987); Bundgaard H. "Prodrugs as a means to improve the delivery of peptide drugs", Arfv. *Drug Delivery Rev.* 8(1): 1-38 (1992); Fleisher et al. "Improved oral drug delivery: solubility limitations overcome by the use of prodrugs", Arfv. *Drug Delivery Rev.* 19(2): 115-130 (1996); Fleisher et al. "Design of prodrugs for improved gastrointestinal absorption by intestinal enzyme targeting", *Methods Enzymol.* 112 (Drug Enzyme Targeting, Pt. A): 360-81, (1985); Farquhar D, et al., "Biologically Reversible Phosphate-Protective Groups", *Pharm. Sci.*, 72(3): 324-325 (1983); Freeman S, et al., "Bioreversible Protection for the Phospho Group: Chemical Stability and Bioactivation of Di(4-acetoxy-benzyl) Methylphosphonate with Carboxyesterase," *Chem. Soc., Chem. Commun.*, 875-877 (1991); Friis and Bundgaard, "Prodrugs of phosphates and phosphonates: Novel lipophilic alphaacyloxyalkyl ester derivatives of phosphate- or phosphonate containing drugs masking the negative charges of these groups", *Eur. J. Pharm. Sci.* 4: 49-59 (1996); Gangwar et al., "Pro-drug, molecular structure and percutaneous delivery", *Des. Biopharm. Prop. Prodrugs Analogs, [Symp.]* Meeting Date 1976, 409-21. (1977); Nathwani and Wood, "Penicillins: a current review of their clinical pharmacology and therapeutic use", *Drugs* 45(6): 866-94 (1993); Sinhababu and Thakker, "Prodrugs of anticancer agents", *Adv. Drug Delivery Rev.* 19(2): 241-273 (1996); Stella et al., "Prodrugs. Do they have advantages in clinical practice?", *Drugs* 29(5): 455-73 (1985); Tan et al. "Development and optimization of anti-HIV nucleoside analogs and prodrugs: A review of their cellular pharmacology, structure-activity relationships and pharmacokinetics", *Adv. Drug Delivery Rev.* 39(1-3): 117-151 (1999); Taylor, "Improved passive oral drug delivery via prodrugs", *Adv. Drug Delivery Rev.,* 19(2): 131-148 (1996); Valentino and Borchardt, "Prodrug strategies to enhance the intestinal absorption of peptides", *Drug Discovery Today* 2(4): 148-155 (1997); Wiebe and Knaus, "Concepts for the design of anti-HIV nucleoside prodrugs for treating cephalic HIV infection", *Adv. Drug Delivery Rev.:* 39(1-3):63-80 (1999); Waller et al., "Prodrugs", *Br. J. Clin. Pharmac.* 28: 497-507 (1989), which are incorporated by reference herein in their entireties.

In some embodiments, a GDF11 polypeptide as described herein can be a pharmaceutically acceptable solvate. The term "solvate" refers to a peptide as described herein in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions.

The peptides of the present invention can be synthesized by using well known methods including recombinant methods and chemical synthesis. Recombinant methods of producing a peptide through the introduction of a vector including nucleic acid encoding the peptide into a suitable host cell is well known in the art, such as is described in Sambrook et al., Molecular Cloning: A Laboratory Manual, 2d Ed, Vols 1 to 8, Cold Spring Harbor, N.Y. (1989); M. W. Pennington and B. M. Dunn, Methods in Molecular Biology Peptide Synthesis Protocols, Vol 35, Humana Press, Totawa, N.J. (1994), contents of both of which are herein incorporated by reference. Peptides can also be chemically synthesized using methods well known in the art. See for example, Merrifield et al., J. Am. Chem. Soc. 85:2149 (1964); Bodanszky, M., Principles of Peptide Synthesis, Springer-Verlag, New York, N.Y. (1984); Kimmerlin, T. and Seebach, D. J. Pept. Res. 65:229-260 (2005); Nilsson et al., Annu. Rev. Biophys. Biomol. Struct. (2005) 34:91-118; W. C. Chan and P. D. White (Eds.) Fmoc Solid Phase Peptide Synthesis: A Practical Approach, Oxford University Press, Cary, N.C. (2000); N. L. Benoiton, Chemistry of Peptide Synthesis, CRC Press, Boca Raton, Fla. (2005); J. Jones, Amino Acid and Peptide Synthesis, $2^{nd}$ Ed, Oxford University Press, Cary, N.C. (2002); and P. Lloyd-Williams, F. Albericio, and E. Giralt, Chemical Approaches to the synthesis of peptides and proteins, CRC Press, Boca Raton, Fla. (1997), contents of all of which are herein incorporated by reference. Peptide derivatives can also be prepared as described in U.S. Pat. Nos. 4,612,302; 4,853,371; and 4,684,620, and U.S. Pat. App. Pub. No. 2009/0263843, contents of all which are herein incorporated by reference.

In some embodiments, the technology described herein relates to a nucleic acid encoding a GDF11 polypeptide as described herein. As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one strand nucleic acid of a denatured double-stranded DNA. Alternatively, it can be a single-stranded nucleic acid not derived from any double-stranded DNA. In one aspect, the template nucleic acid is DNA. In another aspect, the template is RNA. Suitable nucleic acid molecules are DNA, including genomic DNA or cDNA. Other suitable nucleic acid molecules are RNA, including mRNA. The nucleic acid molecule can be naturally occurring, as in genomic DNA, or it may be synthetic, i.e., prepared based up human action, or may be a combination of the two. The nucleic acid molecule can also have certain modification such as 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA), cholesterol addition, and phosphorothioate backbone as described in US Patent Application 20070213292; and certain ribonucleoside that are is linked between the 2'-oxygen and the 4'-carbon atoms with a methylene unit as described in U.S. Pat. No. 6,268,490, wherein both patent and patent application are incorporated hereby reference in their entirety.

In some embodiments, a nucleic acid encoding a GDF11 polypeptide can comprise the nucleotide sequence of SEQ ID NO: 3.

In some embodiments, a nucleic acid encoding a GDF11 polypeptide as described herein is comprised by a vector. In some of the aspects described herein, a nucleic acid sequence encoding a GDF11 polypeptide as described herein, or any module thereof, is operably linked to a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

As used herein, the term "viral vector" refers to a nucleic acid vector construct that includes at least one element of viral origin and has the capacity to be packaged into a viral vector particle. The viral vector can contain the nucleic acid encoding a GDF11 polypeptide as described herein in place of non-essential viral genes. The vector and/or particle may be utilized for the purpose of transferring any nucleic acids into cells either in vitro or in vivo. Numerous forms of viral vectors are known in the art.

By "recombinant vector" is meant a vector that includes a heterologous nucleic acid sequence, or "transgene" that is capable of expression in vivo. It should be understood that the vectors described herein can, in some embodiments, be combined with other suitable compositions and therapies. In some embodiments, the vector is episomal. The use of a suitable episomal vector provides a means of maintaining the nucleotide of interest in the subject in high copy number extra chromosomal DNA thereby eliminating potential effects of chromosomal integration.

In some embodiments the level of GDF11 in the subject is increased by at least 20% over the level of GDF11 in the subject prior to treatment, e.g. 20% or more, 30% or more, 40% or more, 50% or more, 100% or more, 150% or more, 200% or more, 250% or more, 300% or more, or 350% or more. In some embodiments the level of GDF11 in the subject is increased by at least 100% over the level of GDF11 in the subject prior to treatment. In some embodiments the level of GDF11 in the subject is increased by at least 200% over the level of GDF11 in the subject prior to treatment. In some embodiments the level of GDF11 in the subject is increased by about 250% over the level of GDF11 in the subject prior to treatment. In some embodiments, the level of GDF11 in the subject is increased to at least 50% of a healthy reference level, e.g. 50% or more, 60% or more, 70% or more, 80% or more, 90% or more, or 100% or more of a healthy reference level. In some embodiments, the level of GDF11 in the subject is increased to at least 60% of a healthy reference level. In some embodiments, the level of GDF11 in the subject is increased to at least 75% of a healthy reference level. In some embodiments, the level of GDF11 in the subject is increased to at least 90% of a healthy reference level. A healthy reference level can be the average level of GDF11 in a population of human subjects not exhibiting any signs or symptoms of cardiac hypertrophy, diastolic heart failure, or related conditions.

In some embodiments, a healthy reference level can be the average level of GDF11 in a population of human subjects not exhibiting any signs or symptoms of cardiac hypertrophy, diastolic heart failure, or related conditions and who are under the age of 70. In some embodiments, a healthy reference level can be the average level of GDF11 in a population of human subjects not exhibiting any signs or symptoms of cardiac hypertrophy, diastolic heart failure, or related conditions and who are under the age of 65. In some embodiments, a healthy reference level can be a level equivalent to at least 8,500 units as measured by the aptamer technology described in the Examples herein, e.g. 8,500 or greater, 9,000 or greater, or 10,000 or greater.

In some embodiments, the methods described herein can comprise selecting a subject with a level of GDF11 which is lower than a healthy reference level and administering a treatment as described herein.

In some embodiments, the level of GDF11 in a subject is increased in order to treat a cardiac condition, e.g. cardiac hypertrophy or stiffening as described herein. In some embodiments, the level of GDF11 in a subject is increased in order to prevent a cardiac condition, e.g. cardiac hypertrophy or stiffening as described herein. Cardiac conditions related to low or decreased GDF11 polypeptide tend to develop with the decrease in GDF11 levels that occur with increasing age. Thus, it is expected that such conditions can be prevented or, at a minimum, delayed, by maintaining GDF11 polypeptide levels at or near the level found in normal, healthy young adults, e.g. by administering a GDF11 polypeptide or a nucleic acid encoding a GDF11 polypeptide with advancing age, but prior to the onset of a cardiac disorder.

Aspects of the technology described herein relate to compositions comprising a GDF11 polypeptide as described herein or a nucleic acid encoding a GDF11 polypeptide as described herein. In some embodiments, the composition is a pharmaceutical composition. As used herein, the term "pharmaceutical composition" refers to the active agent in combination with a pharmaceutically acceptable carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The preparation of a pharmacological composition that contains active ingredients dissolved or dispersed therein is well understood in the art and generally need not be limited based on formulation. Typically such compositions are prepared as injectable either as liquid solutions or suspensions, however, solid forms suitable for solution, or suspension, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents, and the like which enhance the effectiveness of the active ingredient. The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic, and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine, and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the invention that will be effective in the treatment of a particular disorder or condition will depend on the nature of the disorder or condition, and can be determined by standard clinical techniques.

In some embodiments, a GDF11 polypeptide or nucleic acid encoding a GDF11 polypeptide as described herein can be administered by controlled- or delayed-release means. Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Chemg-ju, Controlled-release Dosage Form Design, 2 (Technomic Publishing, Lancaster, Pa.: 2000).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug.

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

In some embodiments, the technology described herein relates to a syringe comprising a therapeutically effective amount of a composition e.g. a pharmaceutical preparation comprising a GDF11 polypeptide as described herein.

As used herein, the phrase "therapeutically effective amount", "effective amount" or "effective dose" refers to an amount that provides a therapeutic or aesthetic benefit in the treatment, prevention, or management of, for example, cardiac hypertrophy, e.g. an amount that provides a statistically significant decrease in at least one symptom, sign, or marker of cardiac hypertrophy. Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents.

In one aspect, the technology described herein relates to a method comprising administering a GDF11 polypeptide or a nucleic acid encoding a GDF11 polypeptide to a subject. In some embodiments, the subject is in need of treatment for cardiac hypertrophy, diastolic heart failure or a related condition as described above herein. In some embodiments, the method is a method of treating a subject. In some embodiments, the method is a method of treating cardiac hypertrophy and/or diastolic heart failure or a related condition in a subject. Such conditions, as well as methods of diagnosing them are described above herein.

As used herein, the terms "treat," "treatment," "treating," or "amelioration" when used in reference to a disease, disorder or medical condition, refer to therapeutic treatments for a condition, wherein the object is to reverse, alleviate, ameliorate, inhibit, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a condition is reduced or halted. That is, "treatment" includes not just the improvement of symptoms or markers, but also a cessation or at least slowing of progress or worsening of symptoms that would be expected in the absence of treatment. Beneficial or desired clinical results include, but are not limited to, alleviation of one or more symptom(s), diminishment of extent of the deficit, stabilized (i.e., not worsening) state of, for example, cardiac hypertrophy, delay or slowing of cardiac hypertrophy, and an increased lifespan as compared to that expected in the absence of treatment. As used herein, the term "administering," refers to the placement of the composition comprising a GDF11 polypeptide or a nucleic acid encoding a GDF11 polypeptide as disclosed herein into a subject by a method or route which results in delivery to a site of action. The pharmaceutical composition comprising a GDF11 polypeptide or a nucleic acid encoding a GDF11 polypeptide can be administered by any appropriate route which results in an effective treatment in the subject.

Data described herein indicate that systemic administration via the vascular system can be effective. Thus administration via the intravenous route is specifically contemplated. However, with appropriate formulation, other routes are contemplated, including, for example, intranasally, intra-arterially; intra-coronary arterially; orally, by inhalation, intraperitoneally, intramuscularly, subcutaneously, intracavity, or by other means known by those skilled in the art. The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired.

Therapeutic compositions containing at least one agent can be conventionally administered in a unit dose, for example. The term "unit dose" when used in reference to a therapeutic composition refers to physically discrete units suitable as unitary dosage for the subject, each unit containing a predetermined quantity of active material calculated to produce the desired therapeutic effect in association with the required physiologically acceptable diluent, i.e., carrier, or vehicle.

The dosage ranges for the agent depends upon the potency, and are amounts large enough to produce the desired effect e.g., a decrease of the rate of cardiac hypertrophy or a reversal of cardiac hypertrophy. The dosage should not be so large as to cause unacceptable adverse side effects. Generally, the dosage will vary with the age, condition, and sex of the patient and can be determined by one of skill in the art. The dosage can also be adjusted by the individual physician in the event of any complication. Typically, the dosage can range from 0.001 mg/kg body weight to 0.5 mg/kg body weight. In one embodiment, the dose range is from 5 µg/kg body weight to 30 µg/kg body weight.

Administration of the doses recited above can be repeated. In some embodiments, the doses are given once a day, or multiple times a day, for example, but not limited to, three times a day. In some embodiments, the doses recited above are administered daily for weeks or months. The duration of treatment depends upon the subject's clinical progress and responsiveness to therapy. Where the GDF11 polypeptide apparently diminishes with age in affected individuals, it is expected that long-term therapy would be required to establish and maintain the benefit of GDF11-based treatment, e.g. for cardiac hypertrophy.

Precise amounts of active ingredient required to be administered depend on the judgment of the practitioner and are particular to each individual. However, suitable dosage ranges for systemic application are disclosed herein and depend on the route of administration. Suitable regimes for administration are also variable, but are typified by an initial administration followed by repeated doses at one or more intervals by a subsequent administration. Alternatively, continuous intravenous infusion sufficient to maintain concentrations in the blood in the ranges specified for in vivo therapies are contemplated. In some embodiments, the dosage range is sufficient to maintain concentrations in the blood in the range found in the blood of a population of normal, healthy human subjects (e.g. those with no signs, symptoms, or makers of cardiac hypertrophy) under the age of 50. In some embodiments, the dosage range is sufficient to maintain concentrations in the blood in the range found in normal, healthy human subjects under the age of 40. In some embodiments, the dosage range is sufficient to maintain concentrations in the blood in the range found in normal, healthy human subjects under the age of 30.

A therapeutically effective amount is an amount of an agent that is sufficient to produce a statistically significant, measurable change in, for example, cardiac hypertrophy. Such effective amounts can be gauged in clinical trials as well as animal studies. Efficacy of an agent can be determined by assessing physical indicators of, for example cardiac hypertrophy as described above herein. In experimental systems, assays for efficacy include measurement of heart mass as well as, determination of myocyte size as determined by histological microscopy, and/or a reduction in expression of aged myocardium marker genes such as ANP and BNP. Such assays are well known in the art and described in detail in the Examples herein. Clinically acceptable methods for detecting or monitoring cardiac hypertrophy are described herein below. In addition, efficacy of an agent can be measured by an increase in GDF11 polypeptides or fragments thereof in a subject being treated with an agent comprising a GDF11 polypeptide or a nucleic acid encoding GDF11 polypeptide.

The efficacy of a given treatment for cardiac hypertrophy can be determined by the skilled clinician. However, a treatment is considered "effective treatment," as the term is used herein, if any one or all of the signs or symptoms of e.g., cardiac hypertrophy are altered in a beneficial manner, other clinically accepted symptoms are improved or ameliorated, e.g., by at least 10% following treatment with an agent as described herein. Efficacy can also be measured by a failure of an individual to worsen as assessed by hospitalization or need for medical interventions (i.e., progression of the disease is halted). Methods of measuring these indicators are known to those of skill in the art and/or described herein. The extent and severity of cardiac hypertrophy and/or the efficacy of a treatment for cardiac hypertrophy can be determined by imaging of the heart to gauge hypertrophy, e.g. using MRI or 2-dimensional echocardiography. Imaging of cardiac hypertrophy is described in more detail in Agarwal and Hartnell "Imaging in Hypertrophic Cardiomyopathy" Medscape Reference, May 27, 2011 (available online at http://emedicine.medscape.com/article/348503-overview); which is incorporated by reference herein in its entirety.

In some embodiments, the methods further comprise administering the pharmaceutical composition described herein along with one or more additional agents, biologics, drugs, or treatments beneficial to a subject suffering from cardiac hypertrophy or diastolic heart failure as part of a combinatorial therapy. In some such embodiments, the agent, biologic, drug, or treatment can be selected from the group consisting of: treatments for high blood pressure (e.g. thiazide diuretics; ACE inhibitors such as enalapril, lisinopril, and captropril; ARBs such as losartan or valsartan; beta blockers such as atenolol, carvedilol, metoprolol and bisoprolol; calcium channel blockers such as amlodipine, diltiazem, nifedipine, and verapamil); aortic valve repair; treatments to relax the muscle or slow the rate of muscle contraction (e.g. beta blockers, calcium channel blockers, or anti-arrhythmic treatments such as disopyramide or amiodarone); septal myectomy; septal ablation; pacemaker implantation; and/or cardioverter-defibrillator implantation.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. These and other changes can be made to the disclosure in light of the detailed description.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

This invention is further illustrated by the following examples which should not be construed as limiting.

Some embodiments of the technology described herein can be defined according to any of the following numbered paragraphs:

1. A method of treating an age-related condition, the method comprising administering to a subject a composition which increases the level of GDF11 polypeptide in the subject.
2. The method of paragraph 1, wherein the age-related condition is selected from the group consisting of:
   a cardiovascular condition; aging of the heart; aging of skeletal muscle; and aging of the brain.
3. The method of any of paragraphs 1-2, wherein the subject has or has been diagnosed with a condition selected from the group consisting of:
   diastolic heart failure; cardiac hypertrophy; age-related cardiac hypertrophy; hypertension; valvular disease; aortic stenosis; genetic hypertrophic cardiomyopathy; or stiffness of the heart due to aging.
4. The method of any of paragraphs 1-3, wherein the level of GDF11 polypeptide is the level of GDF11 in the circulation of the subject.
5. The method of any of paragraphs 1-3, wherein the level of GDF11 polypeptide is the level of GDF11 in the cardiac tissue of the subject.
6. The method of any of paragraphs 1-5, wherein the composition comprises a GDF11 polypeptide.
7. The method of any of paragraphs 1-6, wherein the composition comprises a GDF11 polypeptide comprising the amino acid sequence of SEQ ID NO 14.
8. The method of any of paragraphs 1-6, wherein the composition comprises a GDF11 polypeptide comprising the amino acid sequence of SEQ ID NO 2.
9. The method of any of paragraphs 1-6, wherein the composition comprises a GDF11 polypeptide comprising the amino acid sequence of SEQ ID NO: 1.
10. The method of any of paragraphs 1-6, wherein the composition comprises a GDF11 polypeptide comprising the amino acid sequence of SEQ ID NO: 15.
11. The method of any of paragraphs 1-10, wherein the composition comprises homodimers of GDF11 polypeptides comprising the amino acid sequence of any of SEQ ID NOs: 1, 2, 14, or 15.
12. The method of any of paragraphs 1-11, wherein the composition comprises complexes of GDF11 polypeptides comprising the amino acid sequence of SEQ ID NO 1, 2, 14, or 15.
13. The method of any of paragraphs 1-12, wherein the composition comprises a nucleic acid encoding a GDF11 polypeptide.

14. The method of any of paragraphs 1-13, wherein the composition is administered via a route selected from the group consisting of:

intravenously; subcutaneously; intra-arterial; and intra-coronary arterial.

15. The method of any of paragraphs 1-14, wherein the level of GDF11 is increased by at least 100%.

16. The method of any of paragraphs 1-15, wherein the level of GDF11 is increased to at least 75% of a healthy reference level.

17. A pharmaceutical composition comprising an isolated GDF11 polypeptide and a pharmaceutically acceptable carrier.

18. The use of a GDF11 polypeptide for the treatment of a condition selected from the group consisting of:

a cardiovascular condition; aging of the heart; aging of skeletal muscle; aging of the brain; diastolic heart failure; cardiac hypertrophy; age-related cardiac hypertrophy; hypertension; valvular disease; aortic stenosis; genetic hypertrophic cardiomyopathy; or stiffness of the heart due to aging.

19. The method of paragraph 18, wherein the level of GDF11 polypeptide is the level of GDF11 in the circulation of the subject.

20. The method of any of paragraphs 18-19, wherein the level of GDF11 polypeptide is the level of GDF11 in the cardiac tissue of the subject.

21. The method of any of paragraphs 18-20, wherein the composition comprises a GDF11 polypeptide.

22. The method of any of paragraphs 18-21, wherein the composition comprises a GDF11 polypeptide comprising the amino acid sequence of SEQ ID NO 14.

23. The method of any of paragraphs 18-22, wherein the composition comprises a GDF11 polypeptide comprising the amino acid sequence of SEQ ID NO 2.

24. The method of any of paragraphs 18-22, wherein the composition comprises a GDF11 polypeptide comprising the amino acid sequence of SEQ ID NO: 1.

25. The method of any of paragraphs 18-22, wherein the composition comprises a GDF11 polypeptide comprising the amino acid sequence of SEQ ID NO: 15.

26. The method of any of paragraphs 18-25, wherein the composition comprises homodimers of GDF11 polypeptides comprising the amino acid sequence of any of SEQ ID NOs: 1, 2, 14, or 15.

27. The method of any of paragraphs 18-26, wherein the composition comprises complexes of GDF11 polypeptides comprising the amino acid sequence of SEQ ID NO 1, 2, 14, or 15.

28. The method of any of paragraphs 18-27, wherein the composition comprises a nucleic acid encoding a GDF11 polypeptide.

29. The method of any of paragraphs 18-28, wherein the composition is administered via a route selected from the group consisting of:

intravenously; subcutaneously; intra-arterial; and intra-coronary arterial.

30. The method of any of paragraphs 18-29, wherein the level of GDF11 is increased by at least 100%.

31. The method of any of paragraphs 18-30, wherein the level of GDF11 is increased to at least 75% of a healthy reference level.

EXAMPLES

Example 1

Identification of Growth Differentiation Factor 11 as a Circulating Factor that Reverses Age-Related Cardiac Hypertrophy The most common form of heart failure occurs with normal systolic function, has no specific treatment and often involves cardiac hypertrophy in the elderly. To clarify the biological mechanisms that drive cardiac hypertrophy in aging, the influence of circulating factors was tested using heterochronic parabiosis, a surgical technique in which joining of animals of different ages leads to a shared circulation. After 4 weeks of exposure to the circulation of young mice, cardiac hypertrophy in old mice dramatically regressed, accompanied by reduced cardiomyocyte size and molecular remodeling. Reversal of age-related hypertrophy was not attributable to hemodynamic or behavioral effects of parabiosis, implicating a blood-borne factor. Using modified aptamer-based proteomics, the TGFβ superfamily member GDF11 was identified as a circulating factor in young mice that declines with age. Treatment of old mice to restore GDF11 to youthful levels recapitulated the effects of parabiosis and reversed age-related hypertrophy, providing a new therapeutic opportunity for cardiac aging.

Among the diseases and disorders associated with advancing age, one of the most debilitating is the loss of normal cardiac function leading to heart failure. Heart failure affects approximately 1% of individuals over 50 and over 5% of individuals over 75. With the ongoing steep rise in the proportion of elderly individuals within our population (Schocken et al., 2008), age-related heart failure is becoming increasingly prevalent.

Most age-related heart failure occurs in the setting of normal systolic function. This condition is often associated with cardiac hypertrophy and called "diastolic heart failure", in contrast to "systolic heart failure" (Aurigemma, 2006). Although progress has been made in the treatment of systolic heart failure, with substantial improvements in outcome over the past two decades, progress in treating diastolic heart failure has been much more elusive (Hunt et al., 2009). Indeed, one can argue that there are no specific therapies for patients who experience the ventricular "stiffening" associated with the diastolic dysfunction that accompanies aging (Kitzman and Daniel, 2007).

Emerging evidence indicates that systemic factors profoundly influence tissue aging. Some of these data have emerged from the experimental model of parabiosis, which was first developed in the 19$^{th}$ century (Finerty, 1952). In parabiosis, two mice are surgically joined, such that they develop a shared blood circulation with rapid and continuous exchange of cells and soluble factors at physiological levels through their common circulatory system (Wright et al., 2001). The pair of animals may be the same age (isochronic parabionts) or different ages (heterochronic parabionts). Because parabiotic mice are connected solely through their common circulation, parabiosis is a powerful model to determine whether circulating factors can alter tissue function (Balsam et al., 2004; Brack et al., 2007; Conboy et al., 2005; Eggan et al., 2006; Ruckh et al., 2012; Sherwood et al., 2004; Villeda et al., 2011; Wagers et al., 2002; Wright et al., 2001). Heterochronic parabiosis experiments suggest that blood-borne signals from a young circulation can significantly impact the function of aging tissues, as indicated by the restoration of appropriate activation and function of endogenous, "old" skeletal muscle satellite cells and successful muscle repair after injury following exposure to a "youthful" systemic milieu (Conboy et al., 2005). Conversely, exposing a young mouse to an old systemic environment can inhibit myogenesis (Brack et al., 2008) and neurogenesis (Villeda et al., 2011) in the young mouse.

Here, using a parabiosis model, it is demonstrated that age-related cardiac hypertrophy can be reversed by exposure to a young circulatory environment. These experiments reveal that the cardiac hypertrophy of aging is at least in part mediated by circulating factors, and led to the discovery that systemic GDF11, a TGFβ family member, can reverse age-related cardiac hypertrophy. These data indicate that at least some component of age-related heart failure is hormonal in nature and reversible.

Results

Heterochronic Parabiosis Reverses Age-Related Cardiac Hypertrophy.

Figure 5:
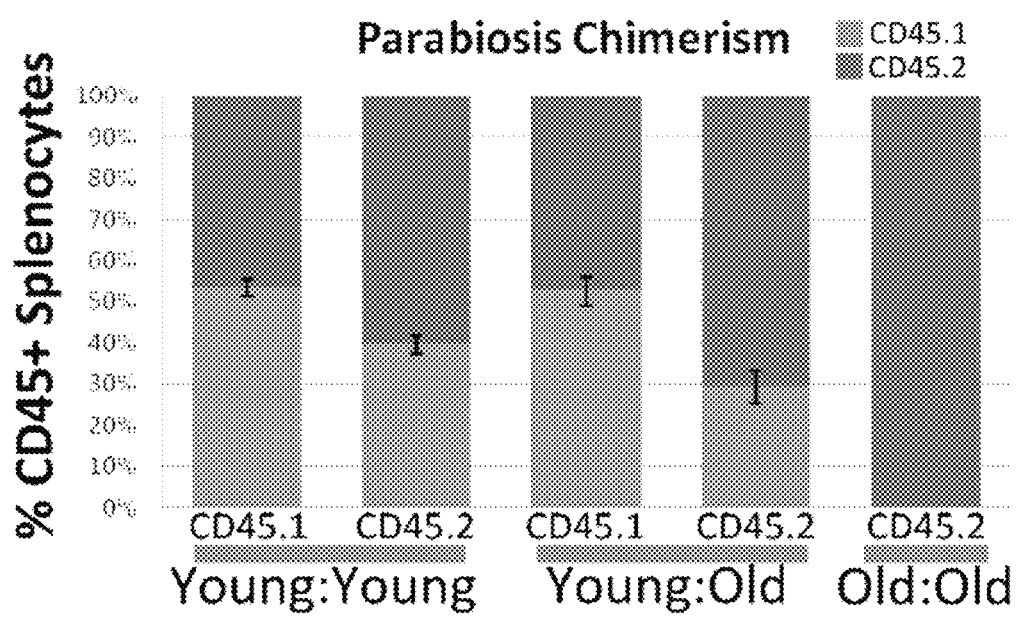
FIG. 5 depicts confirmation of chimerism. Blood chimerism was confirmed in parabiotic pairs by measuring the frequency of donor-derived blood cells from one partner (CD45.1+) in the spleen of the other partner (CD45.2+). Partner-derived cells typically represented 40-50% of splenocytes, consistent with establishment of parabiotic cross-circulation. Because old CD45.1+ mice are not commercially available it was not possible to verify the establishment of chimerism in old parabiotic pairs; however, the inventors' extensive experience with this model, and unpublished data from GFP$^{young}$/WT$^{old}$ pairs strongly support the conclusion that cross-circulation is established equally effectively in these fully isogenic pairs.

The inventors hypothesized that circulating factors specific to a young mouse might reverse cardiac aging. To test this hypothesis, heterochronic parabiotic (HP) pairs were generated, in which young female C57BL/6 mice (Y-HP, 2 months) were surgically joined to old partners (O-HP, 23 months), and compared these to isochronic parabiotic (IP) pairs (young-young, Y-IP, or old-old, O-IP, joined at identical ages, and to age- and sex-matched unpaired mice as controls (young Y and old O) (FIG. 1A). Cardiac aging in C57Bl/6 mice recapitulates human cardiac aging, including development of age-related cardiac hypertrophy (Dai et al., 2009) in a gender independent fashion. Parabiotic pairs were maintained for 4 weeks before analysis, and congenic markers were used to distinguish blood cells from aged (CD45.2+) versus young (CD45.1+) partners (Wright et al., 2001). This strategy allowed blood chimerism in the pairs to be monitored; however, because old CD45.1+ mice are not commercially available, only CD45.2+ mice were used to generate isochronic old pairs. Mice were euthanized 4 weeks after joining, and cross-circulation was confirmed in most of the pairs (>90%) by measuring the frequency of donor-derived blood cells from one partner (CD45.1+) in the blood or spleen of the other partner (CD45.2+) (FIG. 5).

Figure 1B:
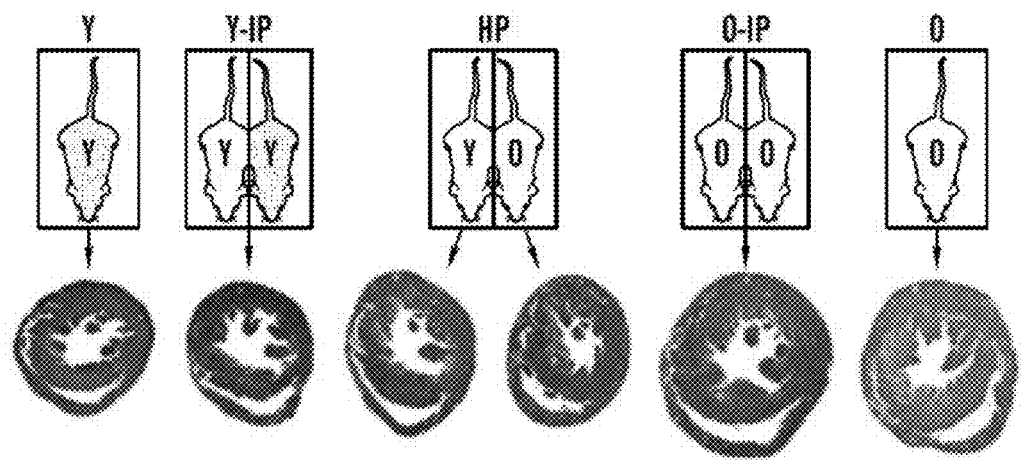
Figure 1C:
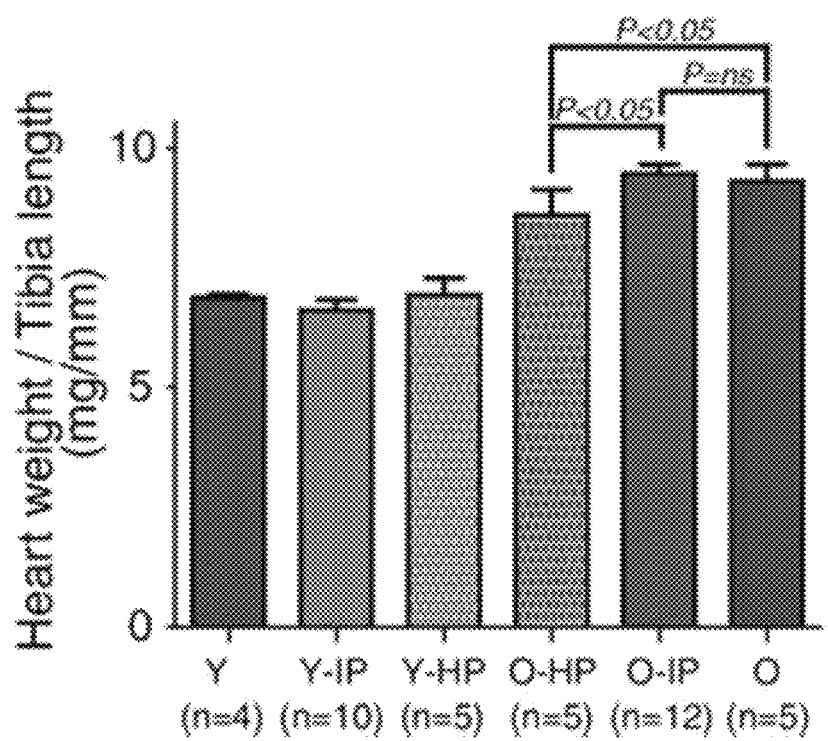

The striking effect of a young circulation on old hearts was immediately apparent on visual inspection. Hearts from old mice exposed to a young circulation (O-HP) for 4 wks were noticeably smaller than hearts from O-IP mice. This observation was confirmed by a blinded comparison of short-axis histological sections taken from the midventricle (FIG. 1B). The hearts were weighed at the time of sacrifice and cardiac mass normalized to tibia length, a standard method that corrects for differences in body frame size (Yoshioka et al., 2007) and that is more appropriate than normalization to body weight when using older mice (Jackson et al., 2012; Yin et al., 1982). The heart weight to tibia length ratio was significantly lower in old mice exposed to a young circulation (O-HP) compared to old mice exposed to an old circulation (O-IP), after 4 weeks of parabiosis (7.93+/−0.19 vs. 9.61+/−0.21 mm/mg, P<0.05, FIG. 1C).

Figure 2A:
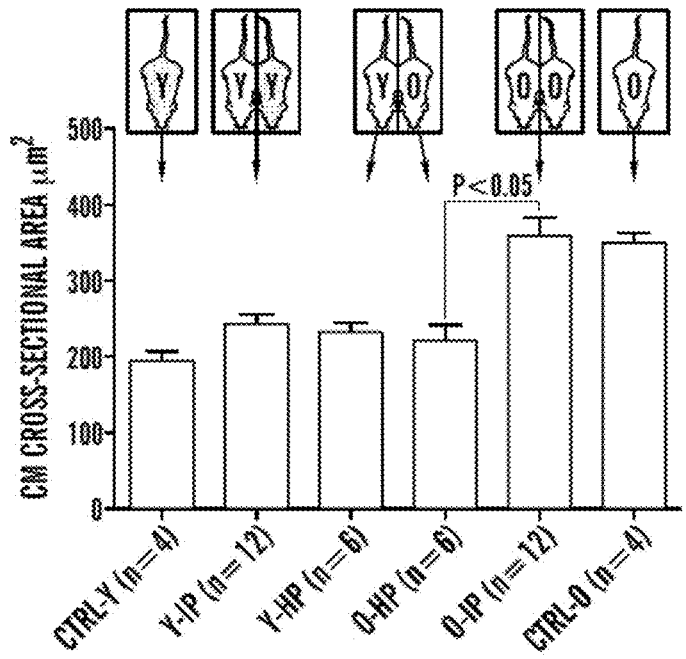
FIGS. 2A-2B demonstrate reversal of age-related cardiomyocyte hypertrophy by exposure to a young circulation.

It was next tested if the gross regression of cardiac hypertrophy was due to changes in cellular hypertrophy by performing blinded morphometric analysis of cardiac histologic sections (data not shown). No significant difference in LV cardiac myocyte cross sectional area in young mice from any of the three experimental conditions was found (186.7±4.9 $\mu m^2$ in Y, 243.1±12.1 $\mu m^2$ in Y-IP, 232.2±16.4 $\mu m^2$ in Y-HP). As expected from published data (Dai et al., 2009), the average cardiac myocyte cross-sectional area was significantly greater in the hearts of the old isochronic (357.8±25.8 $\mu m^2$) and old non-parabiotic controls (348.3±12.6 $\mu m^2$) FIG. 2A). However, aging hearts from mice exposed to a young circulation for 4 wks (O-HP) showed a significant reduction in myocyte size when compared to O-IP hearts (220.4±21.9 vs. 357.8±25.8 $\mu m^2$, P<0.05). Thus, exposure to a young circulation reverses the hypertrophic cellular phenotype of aged hearts to the morphologic phenotype typical of a young adult mouse.

Figure 2B:
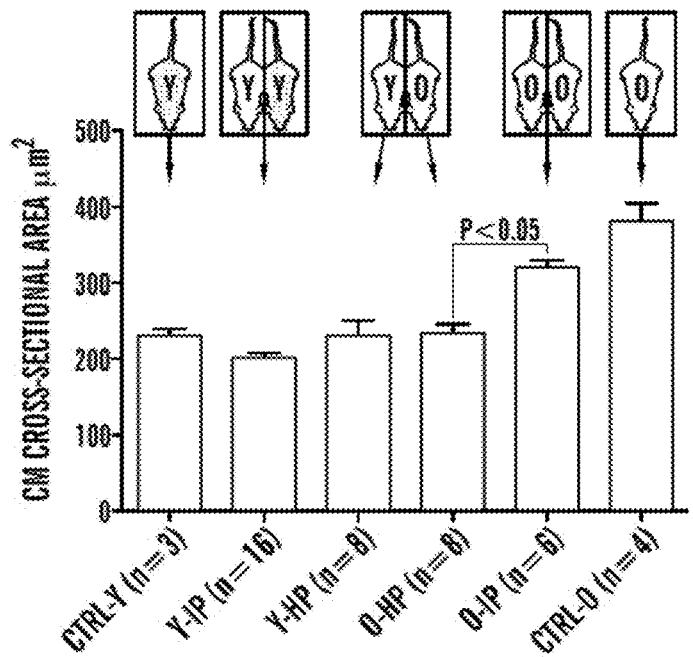

To evaluate possible sex-specific effects, these experiments were repeated using male mice, and a similar regression in age-related hypertrophy after exposure to a young circulation was observed (FIG. 2B). These data indicate that gender is not a factor in the reversal of age-related hypertrophy by a young circulation. Thus, age-dependent cardiac hypertrophy may be reversed in both males and females through the activity of systemic factors, and the striking impact of such youthful factors on this age-related pathology is apparent with only 4 weeks of parabiosis.

The Reversal of Cardiac Hypertrophy in Old Mice Exposed to a Young Circulation is not Explained by a Reduction in Blood Pressure.

Figure 6A:
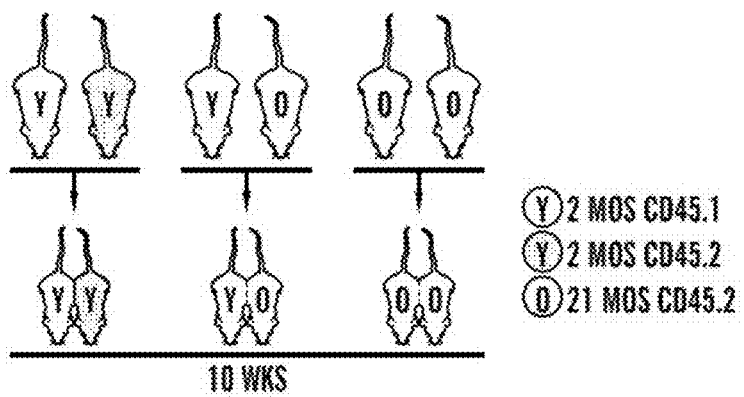
FIGS. 6A-6B depict the design of the experiment and assessment of cardiac mass.

A crucial question raised by these data is whether a hemodynamic effect may mediate the reduced cardiac hypertrophy seen in aged mice following heterochronic parabiosis. To explore the hemodynamic issue in the setting of parabiosis, female heterochronic parabiotic pairs (young, 2 months and old, 21 months) were generated and compared with equal numbers of young and old isochronic parabiotic pairs and with sex and age-matched non-parabiotic controls, using congenic markers to confirm development of cross-circulation (FIG. 6A).

Mice were joined for 10 weeks, and during this period noninvasive blood pressure measurements were performed using a computerized tail-cuff system (BP-2000, Visitech Systems, Apex, N.C.) (Krege et al., 1995) that was modified to hold parabiotic mice. In non-parabiosed controls (FIG. 3A), a significantly lower systolic blood pressure was observed in aged female mice (23 months old and 21 months old, n=32) compared to young (8 wk-old) CD45.2 females (n=12) (98.3±1.8 vs. 129.9±2.0 mmHg, P<0.05), but we saw no difference when comparing aged CD45.2 to young CD45.1 female mice (n=16) (98.3±1.8 vs. 104.1±1.9 mmHg, P=ns). There were no differences in heart rate between the groups (FIG. 3A). These data suggest that differences in blood pressure or heart rate at the time of study entry are unlikely to explain the ensuing changes in myocyte size and global ventricular mass seen in O-HP mice.

Figure 6B:
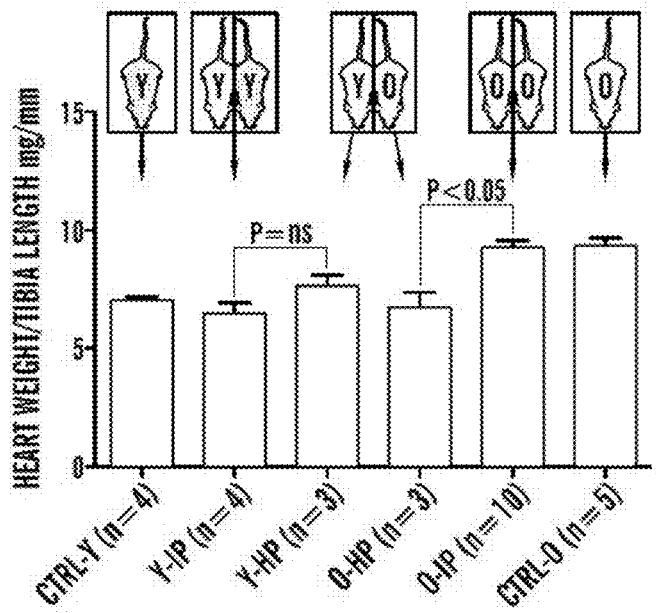

To further address the possible impact of hemodynamic changes in the parabiotic mice, noninvasive blood pressure measurements were performed at serial time points on heterochronic pairs and compared them to isochronic young and old pairs over 10 wks. No change was detected over time in the blood pressure of young mice from any of the groups (FIG. 3B). In contrast, aged mice exposed to a young circulation (O-HP) showed a significant increase in systolic blood pressure at 7 and 10 weeks, and aged members of isochronic pairs exhibited significantly increased blood pressure at 7 weeks, relative to baseline measurements. Finally, terminal intra-arterial hemodynamic tracings were obtained using simultaneous micromanometer catheterizations, performed after mice had been joined for 10 weeks. In these studies, mean arterial pressure did not differ significantly among any of the groups (FIG. 3C). Cross-circulation was confirmed after euthanasia by measuring the frequency of donor-derived blood cells from one partner (CD45.1+) in the spleen of the other partner (CD45.2+) (data not shown), and evaluation of cardiac mass confirmed that O-HP mice in this 10 week experiment also showed significant reduction in the heart weight-tibia length index when compared to the old controls (FIG. 6B). In addition, cardiac size was unaltered in young mice joined for 10 weeks to an old partner, indicating that prolonged exposure to an aged circulation did not induce hypertrophy in young mice, as might be predicted if young mice were serving as a sink for a hypertrophic factor produced by the old mice (FIG. 6B). Finally, consistent with these direct measurements of blood pressure in parabiotic mice, circulating levels of angiotensin II and aldosterone were not different in animals involved in heterochronic parabiosis as compared to their age-matched counterparts joined in isochronic parabiosis (data not shown). Thus, it is unlikely that changes in the renin-angiotensin-aldosterone (RAA) axis, well known for its ability to regulate blood pressure and volume, contribute to remodeling of the myocardium in aged heterochronic parabionts.

Taken together, these data clearly demonstrate that the observed reversal of cardiac hypertrophy in old mice exposed to a young circulation cannot be explained by a simple reduction in blood pressure or modulation of known effectors of blood pressure in the older mice. These data further implicate an anti-hypertrophic factor produced by young mice (rather than dilution of a pro-hypertrophy factor produced by old mice) in the cardiac remodeling induced by heterochronic parabiosis.

Differences in Blood Pressure Between Young CD45.1 and CD45.2 Mice do not Explain the Reversal of Cardiac Hypertrophy.

Because young CD45.1 mice have a significantly lower blood pressure at baseline when compared to young CD45.2 mice, the parabiosis experiments were repeated using exclusively CD45.2 mice to generate heterochronic pairs in which young CD45.2 female mice (Y—HP, 2 months) were joined to aged CD45.2 partners (O-HP, 23 months). These heterochronic mice were compared to isochronic pairs (Y-IP, 2 months, or O-IP, 23 months), after 4 weeks of parabiosis. As the mice in this experiment were genetically identical, flow cytometry could not be used to verify the establishment of chimerism in these pairs; however, extensive experience with this model strongly supports the conclusion that cross-circulation is effectively established in fully isogenic pairs (Pietramaggiori et al., 2009).

Figure 10A:
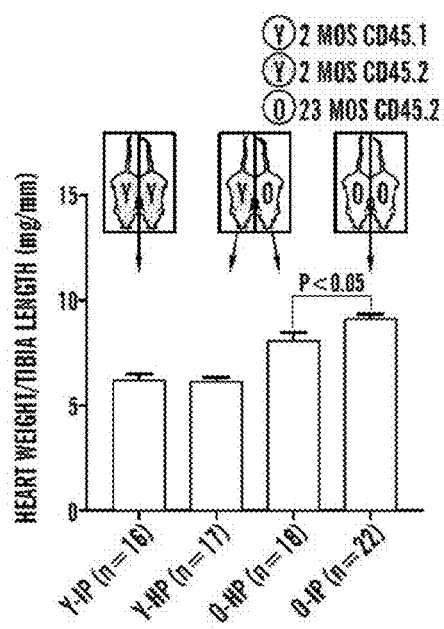
FIGS. 10A-10D demonstrate that differences in blood pressure between young CD45.1 and CD45.2 mice do not explain the reversal of cardiac hypertrophy.
Figure 10C:
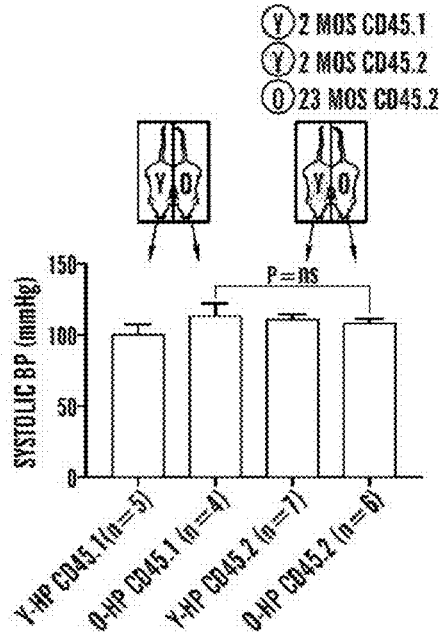
Figure 10B:
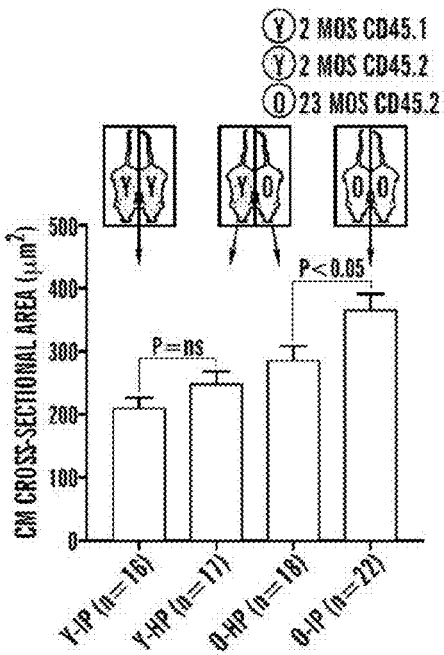
Figure 10D:
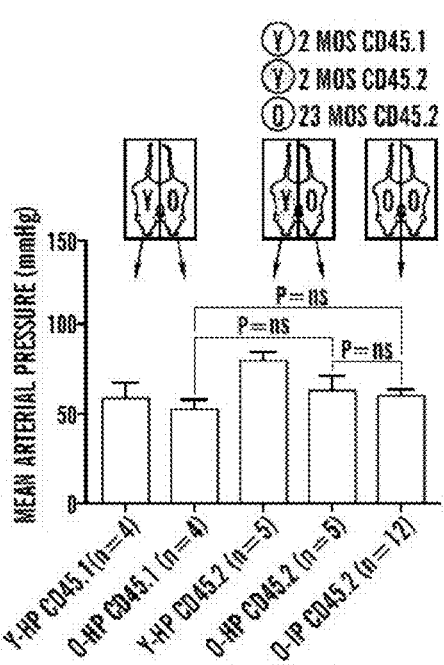

As in prior studies, exposure to the circulation of young CD45.2 mice via parabiosis led to a reduction of heart weight to tibia length ratio in O-HP CD45.2 mice (n=18) when compared to O-IP animals (n=22) (8.03+/−0.38 vs. 9.07+−0.24 mm/mg, P<0.05, FIG. 10A). Cardiomyocyte cross-sectional area was also significantly reduced in O-HP mice when compared to O-IP (286.3±22.7 vs. 366.4±25.4 µm², P<0.05, FIG. 10B). Aged partners of heterochronic pairings using only CD45.2 mice also showed a blood pressure profile after 4 weeks that was comparable to O-HP mice that had been joined to young CD45.1 partners (FIG. 10C-10D). Also, similar to results obtained using CD45.1 young partners, heterochronic parabiosis induced no changes in heart weight/tibia ratio (FIG. 10A), cardiomyocyte size (FIG. 10B), or blood pressure in young CD45.2 mice joined to aged partners (FIG. 10C-10D). These data demonstrate that the regression of cardiac hypertrophy observed in old mice exposed to a young circulation cannot be explained by the blood pressure differences observed in young CD45.1 and CD45.2 C57Bl/6 mice.

Heterochronic Parabiosis is Associated with Molecular Remodeling.

Cardiac hypertrophy is associated with altered expression of a number of cardiac markers. To evaluate the reversal of hypertrophy in O-HP mice on a molecular level, the cardiac transcriptional expression of atrial natriuretic peptide (ANP) and brain natriuretic peptide (BNP), molecular markers of myocyte hypertrophy were quantified (FIGS. 4A-4B). A significant reduction in ANP and BNP transcript levels was detected in the hearts of old mice exposed to a young circulation, as compared to the isochronic age-matched controls. Transcript levels of sarcoplasmic reticulum calcium ATPase (SERCA-2), expression of which may vary with age (Dai et al., 2009) and is functionally important for normal diastolic relaxation was also quantified. SERCA-2 expression was significantly increased in hearts of aged mice exposed to a young circulation (O-HP) when compared to O-IP controls (FIG. 4C). These data provide additional evidence that young circulating factors modify discrete molecular pathways associated with cardiac myocyte hypertrophy and diastolic function.

Behavioral Changes Associated with Parabiosis do not Explain Reversal of Cardiac Hypertrophy in Heterochronic Mice.

Figure 11A:
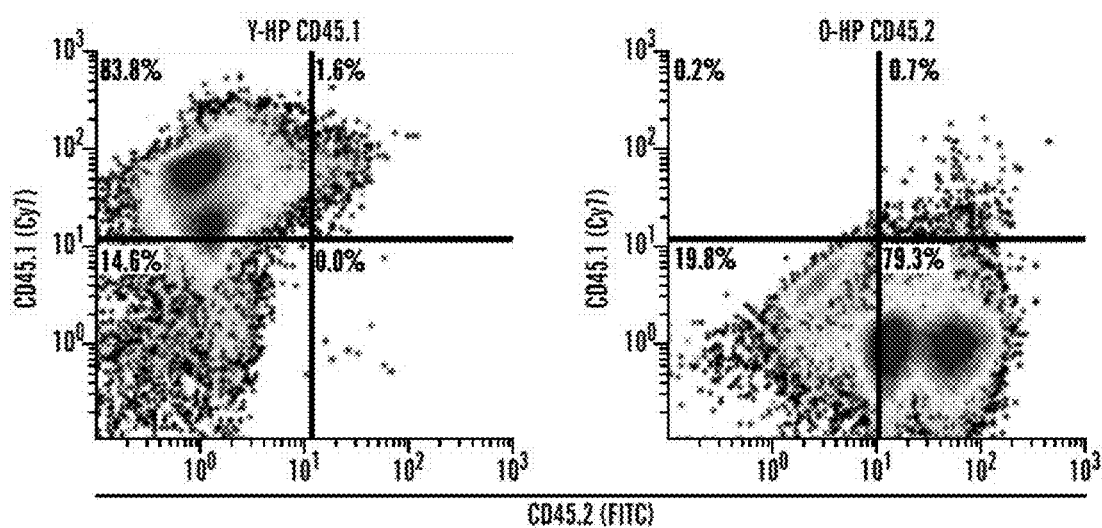
FIGS. 11A-11C demonstrate that heterochronic sham parabiosis does not reverse cardiac hypertrophy in aged mice.
Figure 11B:
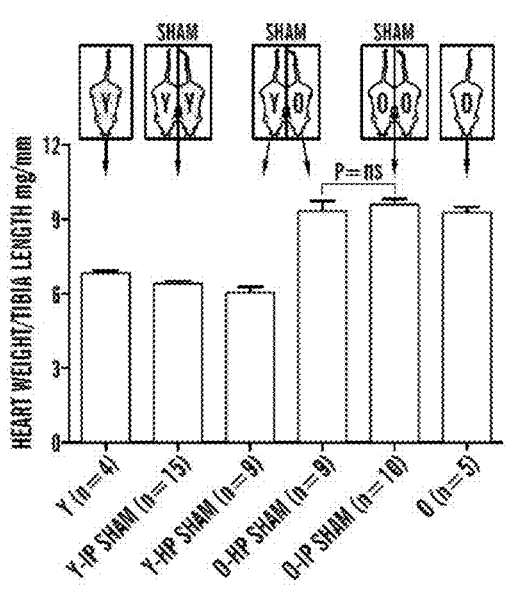
Figure 11C:
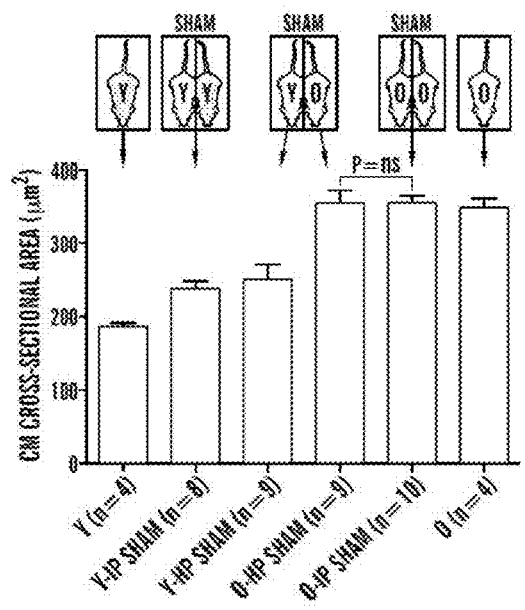

Although the parabiosis model has been used for physiological studies for over a century (Finerty, 1952), the possibility that the physical constraints of parabiotic pairing introduced behavioral changes that contributed to the observed reversal of cardiac hypertrophy was considered. Thus, a surgical technique described herein as "sham parabiosis" was developed, whereby mice are surgically joined while leaving the skin intact, such that they do not develop a shared circulation (FIG. 11A). Sham heterochronic parabiotic pairs, in which young female mice (2 months) were joined to aged partners (23 months) were generated and compared to sham isochronic parabiotic pairs (young-young or old-old) and to age-matched heterochronic and isochronic parabiotic pairs (FIG. 11A-11C). The hearts of sham pairs were analyzed after 4 wks, as in prior experiments. In contrast to conventional parabiotic joining, in which effective cross-circulation was established, no significant difference in heart weight to tibia length ratio was found in aged mice involved in sham heterochronic parabiosis, as compared to aged isochronic shams (9.38+/−0.39 vs. 9.63+/−0.22 mm/mg, P=ns) (FIG. 11B). These data indicate that cross-circulation and exchange of blood-borne factors is required for reversal of age-related cardiac hypertrophy. This finding was also confirmed at the cellular level, since cardiomyocyte size in aged heterochronic shams did not differ from myocyte size in aged isochronic shams (352.9±18.9 vs. 355.0±9.5 µm², P=ns) (FIG. 11C) Finally, ANP, BNP and SERCA-2 transcript levels were evaluated in sham operated pairs. Levels of these molecular markers of hypertrophy were either significantly increased (ANP) or unaltered (BNP and SERCA-2) in old heterochronic shams when compared to old isochronic shams (data not shown), indicating that the molecular remodeling associated with reduced cardiac hypertrophy does not occur in the absence of a shared circulation.

Growth Differentiation Factor 11 is Reduced in the Circulation of Aged Mice and "Youthful" Levels are Restored by Heterochronic Parabiosis.

The studies described above strongly suggest that differences in blood-borne factors in young versus old mice underlie the induced cardiac remodeling observed in old mice after heterochronic parabiosis. To identify candidates that might account for the regression of cardiac hypertrophy in old mice exposed to a youthful circulation, a series of screens on serum and plasma collected from young or old mice involved in isochronic or heterochronic parabiosis (4 weeks duration) were performed. With plasma from old parabionts exposed to a young circulation or from isochronic controls, we performed metabolomic profiling of 69 amino acids and amines; and lipidomics analysis, assessing 142 lipids from 9 lipid classes: lyso-phosphatidylcholines, lyso-phosphatidylethanolamines, sphingomyelins, phosphatidylcholines, diacylglycerols, cholesterol esters, phosphatidylethanolamines, phosphatidyl-inositols and triacylglycerols. However, no significant differences between heterochronic and isochronic parabiotic mice in either the metabolomic or the lipidomic screen were detected (data not shown). A broad scale proteomics analysis (SomaLogic, Inc. Boulder, Colo.) was next performed, using aptamer-based technology to quantitatively evaluate plasma samples from 10 young (2 month) and 10 old (23 month) mice. This approach revealed 13 analytes that reliably distinguished young mice from old mice (Table 1). Of these candidates, one (Growth differentiation factor 11, GDF11, a member of the activin/TGFβ superfamily of growth and differentiation factors) was confirmed in analyses of isochronic and heterochronic parabiotic mice to show differential abundance in the blood plasma of isochronic-old vs. isochronic-young pairs and a more "youthful" expression profile in old-heterochronic animals (FIG. 12A).

Figure 13A:
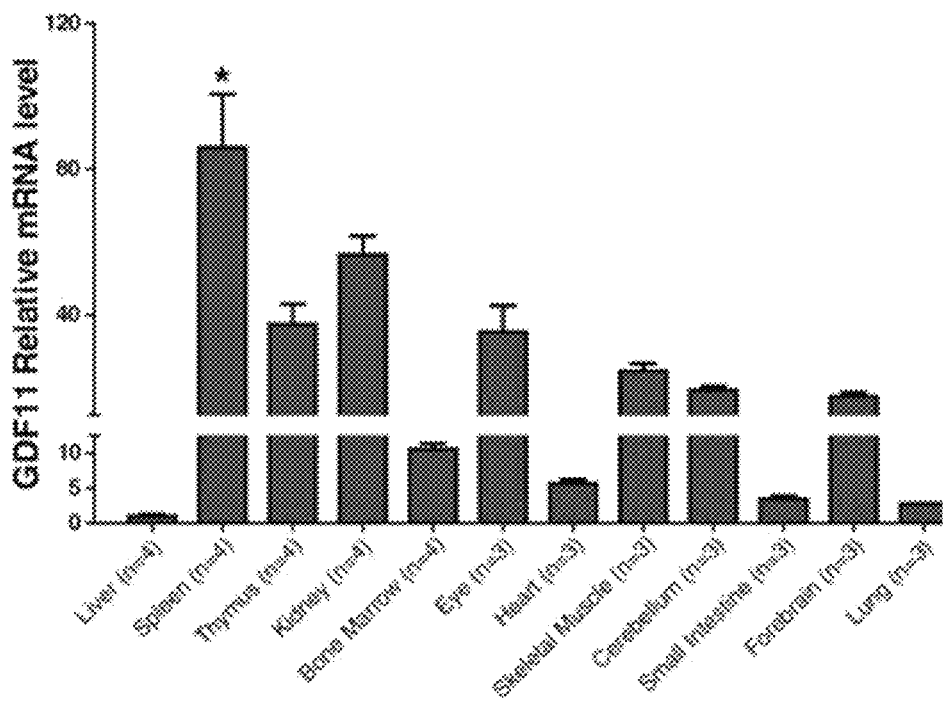
FIGS. 13A-13C demonstrate that spleen has a significantly higher level of GDF11 expression among the analyzed tissues and shows a significant age dependent reduction in GDF11 expression and protein synthesis.
Figure 13B:
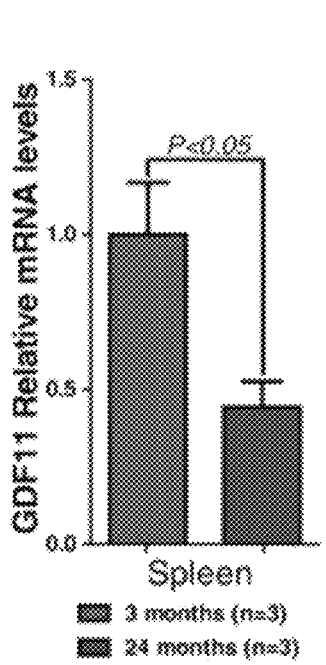
Figure 13C:
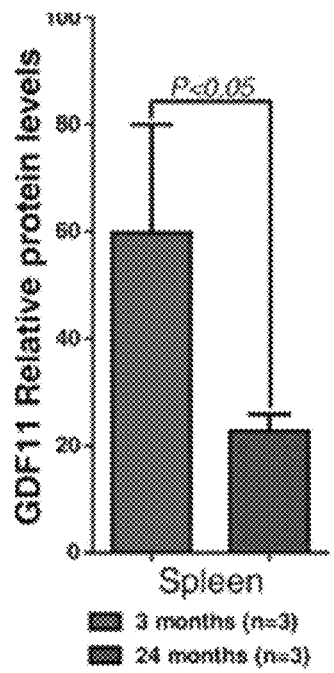
Figure 16:
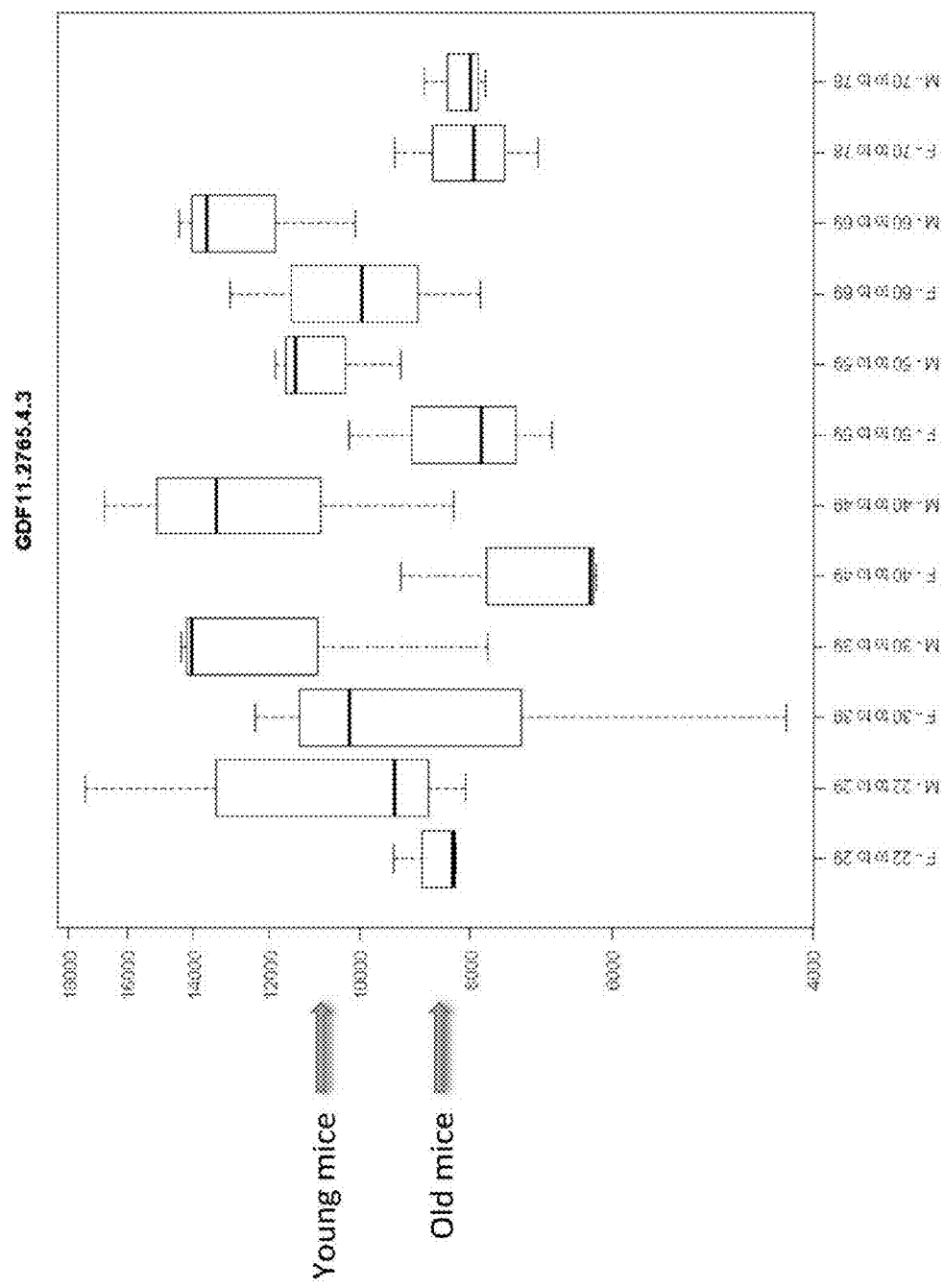
FIG. 16 depicts a graph of serum measurements of GDF11 protein in normal humans, n=3 per group, by age and gender. The approximate levels of young and old mice are shown to the left of the graph in arbitrary units.

To elucidate possible mechanisms for age dependent reduction in circulating GDF11, its expression was analyzed in a range of tissues and cell populations. The data suggest wide-spread expression, as previously reported (McPherson, 2010), with the spleen showing the highest levels of GDF11 mRNA (FIG. 13A). GDF11 expression was next examined as a function of age, comparing the tissues of old (24 months) and young (3 months) C57Bl/6 mice (FIGS. 13B-13C). A significant decline in both GDF11 gene expression and GDF11 protein levels was detected in the spleens of old mice. These data suggest that a reduction in splenic GDF11 could contribute to the decline of circulating GDF11 in aging mice, although as GDF11 is produced in many organs (McPherron, 2010), changes in expression in other tissues and organs may also contribute.

GDF11 Prevents Cardiac Hypertrophy In Vitro and Suppresses Forkhead Transcription Factor Phosphorylation.

It was next tested whether GDF11 displayed anti-hypertrophic properties in cultured neonatal cardiomyocytes using a leucine incorporation assay. After serum starvation, neonatal rat cardiomyocytes were treated for 24 h with recombinant GDF11 (rGDF11) or the closely related TGFβ superfamily protein myostatin at three different concentrations, followed by 24 h exposure to $^3$H-leucine and phenylephrine (50 μM). A significant and reproducible inhibition of phenylephrine-induced $^3$H-leucine incorporation was observed in myocytes treated with 50 nM rGDF11, an effect that was not observed after treatment with myostatin at the same concentration (FIG. 12B). The ability of rGDF11 or myostatin to activate TGFβ pathways was also tested in human induced pluripotent stem cell-derived cardiomyocytes, as previously shown in non-cardiac tissues (Tsuchida et al., 2008). Cells were stimulated for 15 min with serum free media (Control) or with the same media containing rGDF11 (50 nM) or Myostatin (50 nM). Cells stimulated with rGDF11 or with myostatin exhibited a significant increase in pSMAD2 and pSMAD3, consistent with activation of TGFβ pathway, and suppression of Forkhead transcription factor phosphorylation (FIG. 12C). Taken together, these data suggest that GDF11 has a direct anti-hypertrophic effect at the level of the cardiac myocyte.

GDF11 Reverses Age Related Cardiac Hypertrophy In Vivo.

Immunohistochemical staining of mouse cardiac sections with antibodies specific for GDF11 demonstrated evidence for GDF11 at the plasma membranes of cardiomyocytes, and specifically at the intercalated discs, supporting the concept that GDF11 has specific effects at the level of the cardiomyocyte (data not shown). Together with in vitro evidence (FIG. 12B-12C) supporting GDF11-mediated signaling in cardiomyocytes, these data provided the rationale to test whether restoring "youthful" levels of circulating GDF11 in aged mice might reverse age-related cardiac hypertrophy. To determine the optimal dosage, route and interval of administration of rGDF11, a dose-response study was performed, administering the protein to mice by bolus intraperitoneal (i.p.) injection at doses ranging from 0.005 to 0.1 mg/kg (data not shown). Only at the highest dose (0.1 mg/kg) was a reproducible increase in the plasma level of GDF11 1 h after injection observed (FIG. 14). Furthermore, analysis of plasma samples collected serially over 48 h after a single i.p. administration of 0.1 mg/kg rGDF11, indicated that GDF11 levels were persistently elevated for approximately 24 h after this single injection (FIG. 14).

Figure 12D:
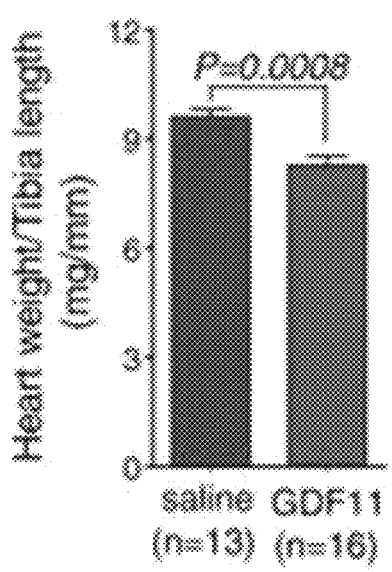
Figure 12E:
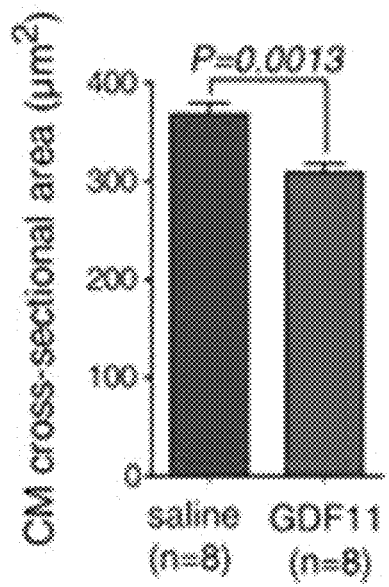

Based on these results, a randomized, blinded, vehicle-controlled study to test the effects of rGDF11 on gross and histologic parameters of cardiac hypertrophy was designed. Old (23 month-old) female mice (C57Bl/6) received a daily intraperitoneal injection of rGDF11 (0.1 mg/kg) or saline for 30 days (n=16 per group). The heart weight to tibia length ratio was significantly lower in old mice injected with rGDF11 compared to the saline injected control group (FIG. 12D). Morphometric analysis further demonstrated that rGDF11 treatment resulted in significantly smaller cardiomyocytes compared to saline-injected controls (FIG. 12E).

Figure 12F:
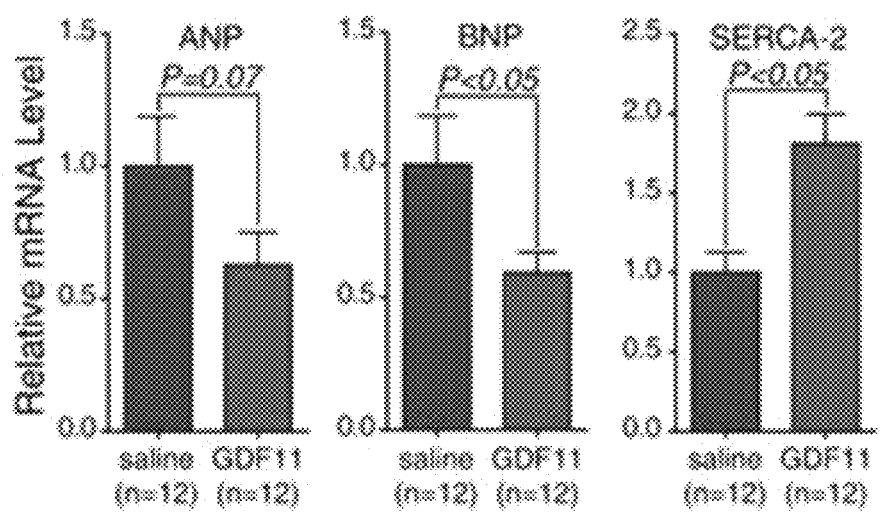

Also investigated were the molecular changes in the hearts of rGDF11-treated aged mice. A significant reduction in BNP and a similar trend in ANP, both molecular markers associated with cardiac hypertrophy was detected (FIG. 12F). Conversely, SERCA-2 transcript levels, which correlate with diastolic function (Dai et al., 2009), were increased in rGDF11 treated hearts relative to saline-treated age-matched controls. This pattern of rGDF11-induced decrease in molecular markers of hypertrophy and increase in SERCA-2 expression resembles the pattern observed in old mice exposed to a young circulation by parabiosis. Echocardiographic evaluation of 24 month old male C56Bl/6 mice that were randomized to receive a daily intraperitoneal injection of rGDF11 (0.1 mg/Kg) or vehicle for 30 days was performed. None of the functional parameters we evaluated was significantly different between the two groups (Table 2).

GDF11 does not Prevent Cardiac Hypertrophy after Pressure Overload In Vivo.

To determine if the effect of GDF11 on cardiomyocytes is specific for age-related cardiac hypertrophy, 2 month old female C56Bl/6 mice were subjected to transverse aortic constriction and then randomized to receive a daily IP injection of rGDF11 (0.1 mg/Kg) or vehicle for 30 days. An echocardiographic evaluation was performed at 15 days and then prior to sacrifice (FIG. 15C). After 30 days, mice were euthanized and hearts were collected for histological and molecular evaluation. Cardiac morphometry was evaluated by measuring the heart weight/tibia length ratio: there was no significant reduction in hypertrophy in mice subjected to aortic banding and treated for 30 days with rGDF11 (n=10) as compared with hearts of mice that received only vehicle (n=9) (P=0.4, FIG. 15A). Furthermore, cardiomyocyte cross sectional area was not significantly different (FIG. 15B).

Development of cardiac fibrosis was evaluated and did not detect any difference between the two groups (data not shown). These data suggest that GDF11 does not prevent all forms of cardiac hypertrophy.

Discussion

Left ventricular hypertrophy is an important feature of cardiac aging, contributing to diastolic dysfunction and heart failure with preserved systolic function (Lakatta and Levy, 2003). An autopsy study of elderly subjects without hypertension or clinically evident cardiovascular disease performed by Anversa and colleagues describes cardiomyocyte enlargement and decreased cardiomyocyte number, without a change in total myocardial mass, a pattern that was more pronounced in males (Olivetti et al., 1995). A cross-sectional study of a similar patient population, however, suggests an increase in left ventricular wall thickness in both sexes (Lakatta and Levy, 2003). Patients with diastolic dysfunction tend to be older and are more likely to be obese, diabetic, hypertensive and female, compared to patients with systolic dysfunction (Owan and Redfield, 2005), suggesting distinct underlying pathological mechanisms.

The central hypothesis of this study is that the aging cardiac phenotype is reversible upon exposure to factors in a young circulation. This hypothesis was tested using surgically anastomosed parabiotic mice. C56Bl/6 mice were used for these experiments because they develop an age-related cardiac phenotype that resembles humans. In addition, because gender can play a role in physiologic cardiac hypertrophy (Foryst-Ludwig et al., 2011), experiments were performed in both males and females. Exposure of old mice to a young circulation via parabiosis reproducibly led to a reversal of cardiac myocyte hypertrophy in a gender-independent fashion, and this reduced cardiomyocyte size translated into a reduction in global cardiac mass. This structural transformation was accompanied by a reduction in myocardial gene expression of natriuretic peptides known to promote maladaptive cardiac remodeling and an increase in Ca2+ ATPase (SERCA-2), the expression of which is integral to myocardial relaxation and hence normal diastolic function. Together, these data are consistent with the concept that factors present in a young circulation can reverse critical structural and molecular aspects of cardiac aging.

With circulatory transfer of a soluble substance emerging as a likely mechanism of cardiac hypertrophy regression in old parabiotic mice, a systematic search was performed to identify candidate factors present at higher levels in the blood of young mice that might underlie the anti-hypertrophic effect. The proteomic analysis identified several factors with levels that change with age, and it cannot be excluded that other factors also participate in the effect observed in heterochronic parabiosis; however, GDF11 emerged as a strong candidate from a series of screening analyses comparing the lipid profiles, metabolites, and signaling proteins present in young versus old plasma. While GDF11 expression is detectable in a range of tissues, the spleen shows the highest concentration, and exhibits an age dependent decline in GDF11 levels. Thus, the spleen may contribute to circulating GDF11 and an age-related production or secretory defect in the spleen could participate in the reduction in circulating GDF11 in old mice.

A recent study shows that the treatment of cachexic mice with soluble ActRIIB protein (sActRIIB), which antagonizes signaling by GDF11 (as well as myostatin, activin, and other TGFβ family members, given the promiscuity of the receptors (Tsuchida et al., 2008)) reverses cardiac atrophy in tumor-bearing animals (Zhou et al., 2010). Together with the proteomic data, this study further supported the notion that GDF11 acts as a mediator of the systemic anti-hypertrophic activity found in young mice. Moreover, the histological data (data not shown) suggested binding of GDF11 to cardiomyocytes in vivo. A randomized, vehicle-controlled study was therefore performed, administering rGDF11 to old mice for 30 d. This rGDF11 therapy led to a significant regression of cardiac hypertrophy in old mice, as indicated by both heart weight measurements and morphometric analyses.

Moreover, the demonstration that rGDF11, but not myostatin, induced a dose-dependent inhibition of phenylephrine-mediated hypertrophy in neonatal cardiac myocytes, in vitro, suggests that GDF11 has specific and direct effects at the level of the cardiac myocyte. Without wishing to be bound by theory, however, both rGDF11 and myostatin stimulated TGFβ signaling pathways in cardiomyocytes, suggesting that the activation of anti-hypertrophic FoxOfactors may promote proteasome-mediated protein degradation (Sandri et al., 2004)

The observation that myostatin negatively regulates skeletal muscle mass led to the development of therapeutic strategies for age- and cancer-related muscle atrophy by blocking myostatin signaling. Interestingly, although myostatin null mice have not consistently demonstrated important changes in cardiac mass during aging (Cohn et al., 2007; Jackson et al., 2012), treatment with a soluble ActRIIB antagonist leads to increased skeletal and cardiac muscle mass, suggesting that the cardiac effects of this antagonist may arise from inhibition of a ligand other than myostatin. Indeed, despite signaling through similar activin receptor combinations, GDF11 and myostatin exhibit many non-overlapping functions. Myostatin null mice demonstrate substantially increased skeletal muscle mass, whereas GDF11 null mice exhibit skeletal and renal abnormalities and die within 24 h of birth (McPherron et al., 1999). Thus, it is contemplated therein that the reported ActRIIB antagonist effects on myocardium (Zhou et al., 2010) may be due to inhibition of GDF11 signaling and independent of effects on myostatin.

GDF11 was ineffective in preventing cardiac hypertrophy in the context of pressure overload. Interestingly, our preliminary studies suggest that GDF11 treatment may influence aging phenotypes in other tissues, such as skeletal muscle.

In summary, the analysis of reverse remodeling in the hearts of heterochronic parabiotic mice led to the identification of GDF11 as an age-regulated circulating factor with potent anti-hypertrophic properties. These studies implicate GDF11 in age-related cardiac hypertrophy (Table 1). Further, GDF11 does stimulate phosphorylation of target protein (SMAD2/3) in human pluripotent cell-derived cardiomyocytes (FIG. 12C). The results described herein provide therapeutic possibilities for targeting cardiac hypertrophy of aging by restoring youthful levels of circulating GDF11.

Experimental Procedures:

Animals.

Aged (21-23 months) C57Bl/6 mice were obtained from the National Institute on Aging (NIA); young (2 months) C57Bl/6 (CD45.1$^-$CD45.2$^+$) or young B6.SJL (CD45.1$^+$ CD45.2$^-$) mice were obtained from JAX.

Parabiosis.

Parabiosis was performed as described previously (Bunster and Meyer, 1933; Ruckh et al., 2012). Blood chimerism was confirmed in a subset of parabiotic pairs by flow cytometry measuring the frequency of donor-derived blood cells from one partner (CD45.1$^+$) in the spleen of the other partner (CD45.2$^+$). Partner-derived cells typically represented 40-50% of splenocytes, consistent with establishment of parabiotic cross-circulation. Because old CD45.1+ mice are not commercially available we could not use this method to verify the establishment of chimerism in isochronic-old parabiotic pairs.

Sham Parabiosis.

Sham parabiosis was performed as a modification of the parabiosis procedure (Bunster and Meyer, 1933; Ruckh et al., 2012) to achieve surgical joining without development of a shared circulation. Mice were anesthetized to full muscle relaxation and joined by a modification of the technique of Bunster and Meyer. After shaving the corresponding lateral aspects of each mouse, matching skin incisions were made from the olecranon to the knee joint of each mouse, and the subcutaneous fascia was bluntly dissected to create about ½ cm of free skin. The olecranon and knee joints were attached with a single 2-0 prolene suture. The suture was sequentially passed through the skin and joint of the first mouse, through a silicon disk to separate the skin of the two mice, and then through the skin and joint of the second mouse. The suture was tied, such that the silicon disk separated the skin of each mouse at the joint and without any contact between the cutaneous flaps of each mouse. The skin incisions were closed with staples. The prolene sutures connecting the mice were reinforced with meshed staples.

Morphometric Assessment of Cardiomyocyte Size.

Mouse hearts were fixed with 4% paraformaldehyde, paraffin-embedded, sectioned, and stained with periodic acid Schiff (PAS) Staining, scanning, and quantification were carried out in a blinded manner using 5 randomly selected sections from the heart.

Noninvasive Blood Pressure.

A computerized tail-cuff system (BP-2000, Visitech Systems, Apex, N.C.) was modified to allow simultaneous blood pressure measurement of both members of the parabiotic pair. Unoperated mice or pairs of mice were trained for 5 consecutive days in the pre-warmed tail-cuff device to accustom them to the procedure, followed by measurements of heart rate and systolic blood pressure.

Neurohormonal Measurements.

Circulating levels of angiotensin II and aldosterone in serum samples were measured by ELISA (Enzo Life Sciences International, INC., USA)

Proteomic Analysis.

EDTA plasma samples (20 µl) from 20 mice were analyzed on the SomaLogic™ proteomics discovery platform (SOMAscan), which uses SOMAmers™ to measure 1001 proteins simultaneously. SOMAmers™ (Slow Off-rate Modified Aptamers) are nucleic acid-based protein binding reagents evolved through SELEX™ (Tuerk and Gold, 1990) to bind protein targets. SOMAscan™ transforms the concentration of proteins in the matrix into a relative quantity of SOMAmers™, through equilibration binding and removal of unbound SOMAmers™ and proteins. The SOMAmer™ quantity is measured by hybridization to microarrays (for a full description, see (Gold et al., 2010))

In Vitro Cardiac Myocyte Hypertrophy Assay.

Neonatal cardiac myocytes were isolated from post-natal day 1 CD1 rats (Charles River) (Seki et al., 2009). Approximately 36 h after plating, cardiac myocytes were serum starved for 24 h in low-glucose DMEM supplemented with ITS (PAA Laboratories). Cardiac myocytes were pretreated with myostatin (R&D Systems) or rGDF11 (Peprotech) for 24 h, prior to treating with phenylephrine (50 µM, Sigma) and assaying protein synthesis/hypertrophy with $^3$H-leucine (1 µCi/ml, Moravek). rGDF11 and myostatin treatments were continued during the period of exposure to phenylephrine and $^3$H-leucine. 24 h after labeling with $^3$H-leucine, cells were washed with ice-cold PBS and fixed with ice-cold 10% trichloroacetic acid for 45 min at 4 C. Cells were lysed with 0.05M NaOH and analyzed by liquid scintillation.

Statistical Analyses.

Data comparison subjected to one-way ANOVA and post-hoc Bonferonni correction or Student's t-test assuming two-tailed distribution and unequal variances. Statistical significance was assigned for $p<0.05$; results are shown as standard error of the mean.

Flow Cytometry.

All flow cytometry was performed on freshly isolated, unfixed splenocytes kept one ice during all incubation steps. Cells were blocked with HBSS/2% FBS for 10 min prior to resuspension at a concentration of $1\times10^6$ cells per 250 uL. Cells were incubated for 30 min in directly conjugated primary antibodies specific for CD45.1 (eBioscience) and CD45.2 (eBioscience) and washed twice in HBSS, prior to flow analysis. Conjugated isotype control antibodies were used in all experiments.

Gene Expression Analysis.

To quantify expression genes commonly induced by hypertrophic stimuli, hearts from different experimental groups were excised and snap frozen in liquid nitrogen 4 weeks after surgery. RNA was extracted with Trizol reagent (Sigma), transcribed into cDNA with the High Capacity cDNA Reverse Transcription kit (Applied Biosystems) using random primers, and subsequently analyzed by real-time PCR on an Applied Biosystems 7300 Real Time PCR System using SYBR Green™ (Applied Biosystems) or TaqMan™ (Applied Biosystems) and primers for ANP (left: 5'-TCGTCTTGGCCTTTTGGCT-3' (SEQ ID NO: 10); right: 5'-TCCAGGTGGTCTAGCAGGTTCT-3' (SEQ ID NO: 11)), BNP (left: 5'-AGGGAGAACACGGCATCATT-3' (SEQ ID NO: 12); right: 5'-GACAGCACCTTCAGGAGAT-3' (SEQ ID NO: 13)), SERCA-2 (left: 5'-TGGAACAACCCGGTAAAGAGT-3' (SEQ ID NO: 16); right: 5'-CACCAGGGGCATAATGAGCAG-3'(SEQ ID NO: 17)), GDF11 (Mm01159973 m1 TaqMan Gene Expression Assays, Life technologies). Results were normalized to expression of TATA binding protein and presented as fold increase relative to young isochronic animals based on the ∆∆Ct method.

Metabolomic and Lipidomic Profiling Analysis. LC-MS/MS Analysis.

Plasma metabolomic profiling was performed on a 4000 QTRAP triple quadrupole mass spectrometer (Applied Biosystems/Sciex, Foster City, Calif.) with a Turbo V electrospray source coupled to an HPLC system including an HTS PAL autosampler (Leap Technologies, Carrboro, N.C.) and a 1200 series binary pump (Agilent Technologies, Santa Clara, Calif.). This LC-MS/MS system was used for polar metabolites analysis employing hydrophilic-interaction liquid chromatography (HILIC) and also for lipid analysis, each requiring distinct methods of plasma extraction, LS/MS acquisition methods and instrument configurations. The MultiQuant software v. 2.0.2 (AB SCIEX, Foster City, Calif.) was used for automated peak integration and metabolite peaks also were manually reviewed for quality of integration (Roberts et al., 2012). HILIC: Hydrophilic-interaction liquid chromatography is suitable for analyzing hydrophilic metabolites; including amino acids, nucleotides and neurotransmitters. Ten microliters of plasma were extracted with 90 µL of 74.9:24.9:0.2 vol/vol/vol acetonitrile/methanol/formic acid containing 0.2 µg/mL (final concentration) of isotopically labeled valine-d8 and phenylalanine-d8 (Sigma-Aldrich; St Louis, Mo.). The samples were vortexed for 30 seconds, centrifuged (10 minutes, 10,000 rpm, 4° C.) and the supernatants were injected directly into the LC/MS system. Samples underwent hydrophilic interaction chromatography using a 150×2.1 mm Atlantis HILIC™ Silica column (Waters, Milford, Mass.): mobile-phase A, 10 mM ammonium formate and 0.1% formic acid; and mobile-phase B, acetonitrile with 0.1% formic acid. The column was eluted isocratically with 5% mobile-phase A for 0.5 minutes followed by a linear gradient to 60% mobile-phase over 10 minutes and then back to 5% mobile-phase A for 17 minutes. Electrospray ionization (ESI) was used in positive multiple reaction monitoring (MRM) ion mode. Declustering potentials and collision energies were optimized for each metabolite by infusion of reference standards before sample analyses. The ion spray voltage was 5 kV, the source temperature was 425° C. and the MRM window was set to 70 msec. Formic acid, ammonium acetate, LC/MS grade solvents, and valine-d8 were obtained from Sigma-Aldrich (St. Louis, Mo.), with the remainder of isotopically-labeled analytical standards obtained from Cambridge Isotope Laboratories, Inc. (Andover, Mass.). The samples were run in a randomized order to minimize internal variation and were interspaced by mouse pooled plasma samples to account for temporal drift across all analyzed metabolites. The internal standard peak areas were monitored for quality control and individual samples with peak areas differing from the group mean by more than 2 standard deviations were reanalyzed. Metabolites analyzed were selected based on the following criteria: 1) known structural identity; 2) distribution across multiple biochemical pathways; 3) reliable measurement using LC/MS in a high throughput fashion; and, 4) low rate of missingness on our platform (<1%).

Lipid Analysis:

Ten microliters of plasma were extracted with 190 μl of isopropanol containing 0.25 μg/ml (final concentration) 1-dodecanoyl-2-tridecanoyl-sn-glycero-3-phosphocholine (Avanti Polar Lipids, Alabaster, Ala.). After centrifugation, supernatants were injected directly, followed by reverse-phase chromatography using a 150×3.0 mm Prosphere HP C4 column (Grace, Columbia, Md.): mobile-phase A, 95:5: 0.1 vol/vol/vol 10 mM ammonium acetate/methanol/acetic acid; and mobile-phase B, 99.9:0.1 vol/vol methanol/acetic acid. The column was eluted isocratically with 80% mobile-phase A for 2 minutes followed by a linear gradient to 20% mobile-phase A over 1 minute, a linear gradient to 0% mobile phase A over 12 minutes, then 10 minutes at 0% mobile-phase A and a linear gradient to 80% mobile phase A over 9 minutes. MS analyses were carried out using electrospray ionization and Q1 scans in the positive ion mode. Ion spray voltage was 5.0 kV, the source temperature was 400° C. and the declustering potential was 70 V. For each lipid analyte, the first number denotes the total number of carbons in the lipid acyl chain(s) and the second number (after the colon) denotes the total number of double bonds in the lipid acyl chain(s).

Immunohistochemistry.

Mouse hearts were fixed with 4% paraformaldehyde, paraffin embedded, sectioned, and stained with standard immunohistochemistry microscopy methods as previously described. An antigen retrieval step was used in all experiments, by heating samples in a citrate-based buffer (Dako) to 95° C. for 20 min. Primary antibodies were used as follows: rabbit GDF11 antibody 1:500 (Abcam) A biotinylated anti-rabbit secondary followed by ABC reagent and DAB (Vector Laboratories) were used for immunohistochemistry.

Induced Pluripotent Stem Cell-Derived Human Cardiomyocytes.

Induced pluripotent stem cell-derived human cardiomyocytes (iPSC-CM) were obtained from Cellular Dynamics International (CDI) and cultured according to the manufacturer's instructions. Briefly, cells were plated at ~580,000 viable cells per well in 5 ug/ml fibronectin-coated 6 well plates in CDI Plating Medium. Medium was changed after 2 days to CDI Maintenance Medium, and 2 additional changes with this medium were performed at days 4 and 6 post-plating. At the latter point, cells were observed to be beating homogenously. At 7 days post-plating, medium was changed to serum-free DMEM (low glucose) and cells were incubated for an additional 24 h. At this time, cells were exposed to either control serum free media, or the same media with 50 nM myostatin (Peprotech) or 50 nM rGDF11 (Peprotech) for 15 mins. Lysates were collected and western analyses were performed using standard methods. Antibodies used were from Cell Signaling Technology: phospho-Fox01/Fox03a (9464), phospho-SMAD2 (3108), phospho-SMAD3 (9520), GAPDH (2118).

Western Blot Analysis.

Western blot analyses were performed as described previously (Seki et al., 2009). Membranes (polyvinylidene fluoride, PerkinElmer Life Sciences) were incubated with primary antibodies (anti-GDF11 diluted 1:1000, from Abcam) and detected with horseradish peroxidase-conjugated antibodies (1:2000, from Bio-Rad) and enhanced chemiluminescence (PerkinElmer Life Sciences). Spleen western blot analyses were performed with membranes (immune-Blot PVDF membrane, Bio-Rad) incubated with primary antibodies (anti-GDF11, Abcam, 1:500 dilution and alpha-tubuline, Sigma, 1:1000 dilution) and detected with IRDye conjugated antibodies (1:10000 dilution, Li-Cor). Membranes were scanned with Odyssey CLx Infrared Imaging System (Li-Cor) and quantified by densitometry with the Image Studio Software (Li-Cor).

Transverse Aortic Constriction and Echocardiography.

Transverse aortic constriction (TAC) surgery and Echocardiography were performed in in vivo studies using blinded protocols.

REFERENCES

Aurigemma, G. P. (2006). Diastolic heart failure—a common and lethal condition by any name. N Engl J Med 355, 308-310.

Balsam, L. B., Wagers, A. J., Christensen, J. L., Kofidis, T., Weissman, I. L., and Robbins, R. C. (2004). Haematopoietic stem cells adopt mature haematopoietic fates in ischaemic myocardium. Nature 428, 668-673.

Brack, A. S., Conboy, M. J., Roy, S., Lee, M., Kuo, C. J., Keller, C., and Rando, T. A. (2007). Increased Wnt signaling during aging alters muscle stem cell fate and increases fibrosis. Science 317, 807-810.

Bunster, E., and Meyer, R. K. (1933). An improved method of parabiosis. The Anatomical Record 57, 339-343.

Cohn, R. D., Liang, H. Y., Shetty, R., Abraham, T., and Wagner, K. R. (2007). Myostatin does not regulate cardiac hypertrophy or fibrosis. Neuromuscul Disord 17, 290-296.

Conboy, I. M., Conboy, M. J., Wagers, A. J., Girma, E. R., Weissman, I. L., and Rando, T. A. (2005). Rejuvenation of aged progenitor cells by exposure to a young systemic environment. Nature 433, 760-764.

Dai, D. F., Santana, L. F., Vermulst, M., Tomazela, D. M., Emond, M. J., MacCoss, M. J., Gollahon, K., Martin, G.

M., Loeb, L. A., Ladiges, W. C., et al. (2009). Overexpression of catalase targeted to mitochondria attenuates murine cardiac aging. Circulation 119, 2789-2797.

Eggan, K., Jurga, S., Gosden, R., Min, I. M., and Wagers, A. J. (2006). Ovulated oocytes in adult mice derive from non-circulating germ cells. Nature 441, 1109-1114.

Finerty, J. C. (1952). Parabiosis in physiological studies. Physiol Rev 32, 277-302.

Foryst-Ludwig, A., Kreissl, M. C., Sprang, C., Thalke, B., Bohm, C., Benz, V., Gurgen, D., Dragun, D., Schubert, C., Mai, K., et al. (2011). Sex differences in physiological cardiac hypertrophy are associated with exercise-mediated changes in energy substrate availability. Am J Physiol Heart Circ Physiol 301, H115-122.

Gold, L., Ayers, D., Bertino, J., Bock, C., Bock, A., Brody, E. N., Carter, J., Dalby, A. B., Eaton, B. E., Fitzwater, T., et al. (2010). Aptamer-based multiplexed proteomic technology for biomarker discovery. PLoS One 5, e15004.

Hunt, S. A., Abraham, W. T., Chin, M. H., Feldman, A. M., Francis, G. S., Ganiats, T. G., Jessup, M., Konstam, M. A., Mancini, D. M., Michl, K., et al. (2009). 2009 focused update incorporated into the ACC/AHA 2005 Guidelines for the Diagnosis and Management of Heart Failure in Adults: a report of the American College of Cardiology Foundation/American Heart Association Task Force on Practice Guidelines: developed in collaboration with the International Society for Heart and Lung Transplantation. Circulation 119, e391-479.

Jackson, M. F., Luong, D., Vang, D. D., Garikipati, D. K., Stanton, J. B., Nelson, O. L., and Rodgers, B. D. (2012). The aging myostatin null phenotype: reduced adiposity, cardiac hypertrophy, enhanced cardiac stress response, and sexual dimorphism. J Endocrinol 213, 263-275.

Kitzman, D. W., and Daniel, K. R. (2007). Diastolic heart failure in the elderly. Clin Geriatr Med 23, 83-106.

Krege, J. H., Hodgin, J. B., Hagaman, J. R., and Smithies, O. (1995). A noninvasive computerized tail-cuff system for measuring blood pressure in mice. Hypertension 25, 1111-1115.

Lakatta, E. G., and Levy, D. (2003). Arterial and cardiac aging: major shareholders in cardiovascular disease enterprises: Part II: the aging heart in health: links to heart disease. Circulation 107, 346-354.

McPherson, A. C. (2010). Metabolic Functions of Myostatin and Gdf11. Immunol Endocr Metab Agents Med Chem 10, 217-231.

McPherson, A. C., Lawler, A. M., and Lee, S. J. (1999). Regulation of anterior/posterior patterning of the axial skeleton by growth/differentiation factor 11. Nat Genet. 22, 260-264.

Olivetti, G., Giordano, G., Corradi, D., Melissari, M., Lagrasta, C., Gambert, S. R., and Anversa, P. (1995). Gender differences and aging: effects on the human heart. J Am Coll Cardiol 26, 1068-1079.

Owan, T. E., and Redfield, M. M. (2005). Epidemiology of diastolic heart failure. Prog Cardiovasc Dis 47, 320-332.

Pietramaggiori, G., Scherer, S. S., Alperovich, M., Chen, B., Orgill, D. P., and Wagers, A. J. (2009). Improved cutaneous healing in diabetic mice exposed to healthy peripheral circulation. J Invest Dermatol 129, 2265-2274.

Ruckh, J. M., Zhao, J. W., Shadrach, J. L., van Wijngaarden, P., Rao, T. N., Wagers, A. J., and Franklin, R. J. (2012). Rejuvenation of regeneration in the aging central nervous system. Cell Stem Cell 10, 96-103.

Sandri, M., Sandri, C., Gilbert, A., Skurk, C., Calabria, E., Picard, A., Walsh, K., Schiaffino, S., Lecker, S. H., and Goldberg, A. L. (2004). Foxo transcription factors induce the atrophy-related ubiquitin ligase atrogin-1 and cause skeletal muscle atrophy. Cell 117, 399-412.

Schocken, D. D., Benjamin, E. J., Fonarow, G. C., Krumholz, H. M., Levy, D., Mensah, G. A., Narula, J., Shor, E. S., Young, J. B., and Hong, Y. (2008). Prevention of heart failure: a scientific statement from the American Heart Association Councils on Epidemiology and Prevention, Clinical Cardiology, Cardiovascular Nursing, and High Blood Pressure Research; Quality of Care and Outcomes Research Interdisciplinary Working Group; and Functional Genomics and Translational Biology Interdisciplinary Working Group. Circulation 117, 2544-2565.

Seki, K., Sanada, S., Kudinova, A. Y., Steinhauser, M. L., Handa, V., Gannon, J., and Lee, R. T. (2009). Interleukin-33 prevents apoptosis and improves survival after experimental myocardial infarction through ST2 signaling. Circ Heart Fail 2, 684-691.

Sherwood, R. I., Christensen, J. L., Conboy, I. M., Conboy, M. J., Rando, T. A., Weissman, I. L., and Wagers, A. J. (2004). Isolation of Adult Mouse Myogenic Progenitors; Functional Heterogeneity of Cells within and Engrafting Skeletal Muscle. Cell 119, 543-554.

Souza, T. A., Chen, X., Guo, Y., Sava, P., Zhang, J., Hill, J. J., Yaworsky, P. J., and Qiu, Y. (2008). Proteomic identification and functional validation of activins and bone morphogenetic protein 11 as candidate novel muscle mass regulators. Mol Endocrinol 22, 2689-2702.

Tsuchida, K., Nakatani, M., Uezumi, A., Murakami, T., and Cui, X. (2008). Signal transduction pathway through activin receptors as a therapeutic target of musculoskeletal diseases and cancer. Endocr J 55, 11-21.

Tuerk, C., and Gold, L. (1990). Systematic evolution of ligands by exponential enrichment: RNA ligands to bacteriophage T4 DNA polymerase. Science 249, 505-510.

Villeda, S. A., Luo, J., Mosher, K. I., Zou, B., Britschgi, M., Bieri, G., Stan, T. M., Fainberg, N., Ding, Z., Eggel, A., et al. (2011). The ageing systemic milieu negatively regulates neurogenesis and cognitive function. Nature 477, 90-94.

Wagers, A. J., Sherwood, R. I., Christensen, J. L., and Weissman, I. L. (2002). Little evidence for developmental plasticity of adult hematopoietic stem cells. Science 297, 2256-2259.

Wright, D. E., Wagers, A. J., Gulati, A. P., Johnson, F. L., and Weissman, I. L. (2001). Physiological migration of hematopoietic stem and progenitor cells. Science 294, 1933-1936.

Yin, F. C., Spurgeon, H. A., Rakusan, K., Weisfeldt, M. L., and Lakatta, E. G. (1982). Use of tibial length to quantify cardiac hypertrophy: application in the aging rat. Am J Physiol 243, H941-947.

Yoshioka, J., Imahashi, K., Gabel, S. A., Chutkow, W. A., Burds, A. A., Gannon, J., Schulze, P. C., MacGillivray, C., London, R. E., Murphy, E., et al. (2007). Targeted deletion of thioredoxin-interacting protein regulates cardiac dysfunction in response to pressure overload. Circ Res 101, 1328-1338.

Zhou, X., Wang, J. L., Lu, J., Song, Y., Kwak, K. S., Jiao, Q., Rosenfeld, R., Chen, Q., Boone, T., Simonet, W. S., et al. (2010). Reversal of cancer cachexia and muscle wasting by ActRIIB antagonism leads to prolonged survival. Cell 142, 531-543.

Roberts, L. D., Souza, A. L., Gerszten, R. E., and Clish, C. B. (2012). Targeted metabolomics. Curr Protoc Mol Biol Chapter 30, Unit 30 32 31-24.

Seki, K., Sanada, S., Kudinova, A. Y., Steinhauser, M. L., Handa, V., Gannon, J., and Lee, R. T. (2009). Interleukin- 33 prevents apoptosis and improves survival after experimental myocardial infarction through ST2 signaling. Circ Heart Fail 2, 684-691.

TABLE 1

List of serum analytes identified by proteomic analysis.
The table summarizes the 13 analytes
that readily distinguish young mice from old mice.
Serum analytes
(SOMAscan)

Collectin kidney 1
Cathepsin D
Dickkopf-related protein 4
Erythrocyte membrane protein 4.1|Protein 4.1R
Esterase D
Growth-differentiation factor 11|BMP-11
Hemoglobin
Interleukin-1 receptor accessory protein|IL-1 RAcP|IL1 R3
Natural killer group 2 member D|NKG2D
Ras-related C3 botulinum toxin substrate 1
GTP-binding nuclear protein Ran|ARA24
TIMP3|Tissue inhibitor of metalloproteinases 3
Thymidylate synthase

TABLE 2

Echocardiographic data after 30 days of treatment with rGDF11 or vehicle in 23 months old C57Bl/6 male mice.
No significant differences were noted in echocardiographic parameters.

|  | Vehicle (n = 7) | GDF11 (n = 6) |
|---|---|---|
| AWT (mm) | 1.39 ± 0.02 | 1.39 ± 0.01 |
| PWT (mm) | 1.10 ± 0.02 | 1.09 ± 0.04 |
| ESD (mm) | 1.25 ± 0.04 | 1.25 ± 0.03 |
| EDD (mm) | 2.99 ± 0.09 | 3.20 ± 0.05 |
| FS (%) | 57.9 ± 1.6 | 60.9 ± 1.1 |

AWT = anterior wall thickness;
PWT = posterior wall thickness;
EDD = end disastolic dimension;
ESD = end systolic dimension;
FS = fractional shortening.
Data shown as mean ± S.E.M.

Example 2

GDF11

As described herein, cardiac hypertrophy of aging can be rapidly reversed in a matter of weeks by exposure to a young blood circulation. The data presented above herein suggest that there is a circulating factor that is transferred from the young mouse to the old mouse via the shared circulation that is responsible for the rapid regression of cardiac hypertrophy.

Figure 7A:
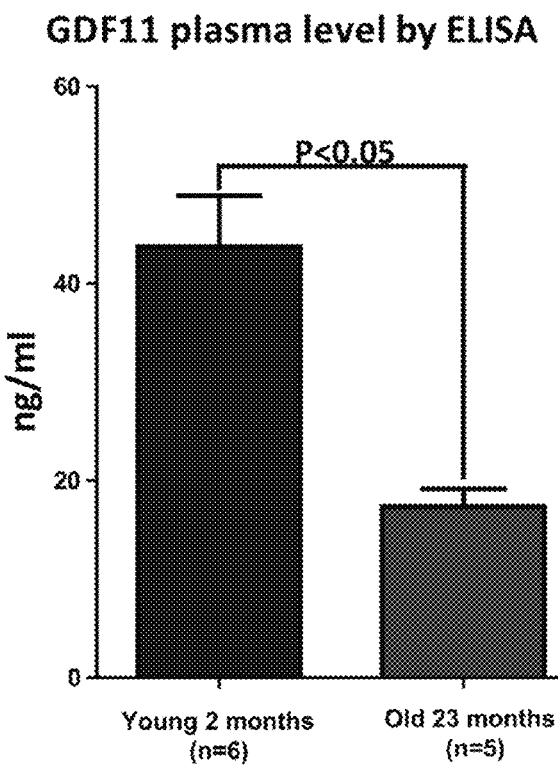
Figure 7B:
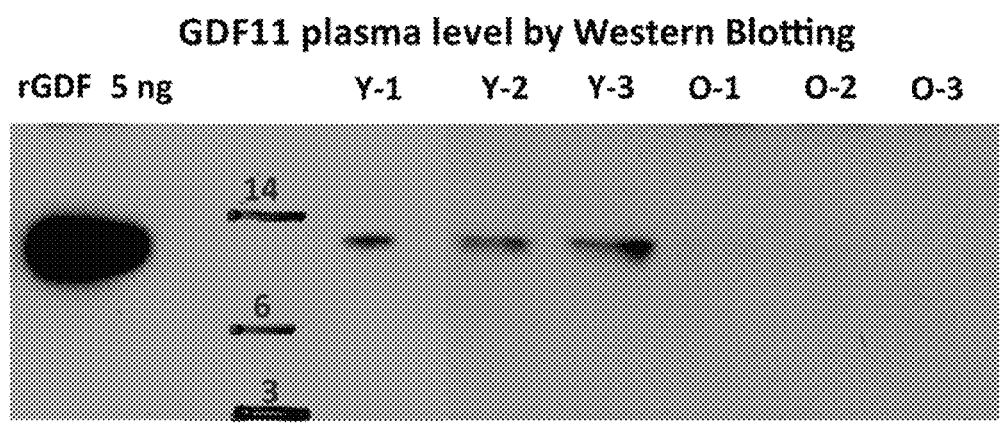
FIG. 7B depicts the results of a Western blot.

An unbiased search for circulating factors present in young mice that could account for the regression of cardiac hypertrophy observed in parabiotic mice was performed. Serum was collected from genetically identical mice from the two age-groups used in the parabiosis experiments, young adults and elderly mice. Using an aptamer-based proteomics platform (Somalogic), a factor called Growth differentiation factor (GDF) 11 was identified that was significantly reduced in old mice, compared to young mice. GDF11 plasma levels were measured by ELISA in Young (2 months) and Old mice (23 months). Circulating levels of GDF11 were significantly higher in young mice (43.7±12.7 ng/ml) when compared to old mice (17.4±3.9 ng/ml) (FIG. 7A). These results were confirmed by Western analysis on plasma from young (n=3) and old (n=3) mice. A 12.5 kDa band corresponding to the mature form of GDF11 is clearly visible in young mice and less intense in old mice (5 µl of plasma loaded in each lane) (FIG. 7B). Further, it was demonstrated that exposure of an old mouse to a young circulation resulted in the restoration of circulating GDF11 to levels similar to young mice (data not shown). From these data, a clear-cut inverse association emerges between circulating GDF11 and cardiac hypertrophy. Moreover, restoration of circulating GDF11 by parabiosis is associated with a regression in cardiac hypertrophy. These data indicate that a reduction in GDF11 with aging can play a role in age-related cardiac hypertrophy, and that an increase in GDF11 can prevent and/or reverse this hypertrophy.

The administration of active GDF11 can induce regression of cardiac hypertrophy and improve diastolic function and clinical heart failure. GDF11—with or without amino acid or other modifications aimed at reducing proteolytic degradation and prolonging half-life—can be used to treat cardiac hypertrophy and diastolic heart failure, including that associated with hypertension, aging, genetic hypertrophic cardiomyopathy, and valvular disease. A therapeutic strategy to restore youthful levels of GDF11 in patients with diastolic heart failure of any etiology is described herein.

REFERENCES

1. D. Lloyd-Jones et al., Circulation 121, e46 (Feb. 23, 2010).
2. F. Bursi et al., JAMA 296, 2209 (Nov. 8, 2006).
3. J. S. Gottdiener et al., Ann Intern Med 137, 631 (Oct. 15, 2002).
4. M. M. Redfield et al., JAMA 289, 194 (Jan. 8, 2003).
5. T. E. Owan et al., N Engl J Med 355, 251 (Jul. 20, 2006).
6. S. Stewart, K. MacIntyre, D. J. Hole, S. Capewell, J. J. McMurray, Eur J Heart Fail 3, 315 (June, 2001).
7. S. A. Hunt et al., Circulation 119, e391 (Apr. 14, 2009).
8. M. Ouzounian, D. S. Lee, P. P. Liu, Nat Clin Pract Cardiovasc Med 5, 375 (July, 2008).
9. J. C. Finerty, Physiol Rev 32, 277 (July, 1952).

Example 3

GDF11 can influence aging phenotypes in other tissues as well. These effects have been explored in several different tissues including skin, skeletal muscle, and brain.

In skeletal muscle GDF11 can reverse the age-related impairment of muscle stem cell genomic integrity, myogenic function and regenerative capacity.

Example 4

Serum levels of GDF11 protein in normal humans was determined using the apatmer technology described in Example 1. The levels in humans depend on gender but fall above the age of 70 in both men and women.

What is claimed herein:

1. A method of treating an age-related cardiac hypertrophy, the method comprising administering to a mammalian subject a composition comprising a mammalian GDF11 polypeptide, whereby the composition increases the level of Growth Differentiation Factor 11 (GDF11) polypeptide in the subject; and wherein the composition is administered intraperitoneally; intravenously; subcutaneously: intra-arterially; or intra-coronary arterially.

2. The method of claim 1, wherein the subject has or has been diagnosed with a condition selected from the group consisting of:
   diastolic heart failure; cardiac hypertrophy; age-related cardiac hypertrophy; hypertension; valvular disease; aortic stenosis; genetic hypertrophic cardiomyopathy; or stiffness of the heart due to aging.

3. The method of claim 1, wherein the level of GDF11 polypeptide is the level of GDF11 in the circulation of the subject or the level of GDF11 in the cardiac tissue of the subject.

4. The method of claim 1, wherein the GDF11 polypeptide comprises an amino acid sequence selected from the group consisting of:
   SEQ ID NO: 14; SEQ ID NO: 2; and SEQ ID NO: 1.

5. The method of claim 1, wherein the composition comprises homodimers of GDF11 polypeptides comprising the amino acid sequence of any of SEQ ID NOs: 1, 2, or 14.

6. The method of claim 1, wherein the composition comprises complexes of GDF11 polypeptides comprising the amino acid sequence of SEQ ID NO 1, 2, 14.

7. The method of claim 1, wherein the level of GDF11 is increased by at least 100%.

8. The method of claim 1, wherein the level of GDF11 is increased to at least 75% of a healthy reference level.

9. A pharmaceutical composition comprising an isolated GDF11 polypeptide and a pharmaceutically acceptable carrier.

* * * * *

UNITED STATES PATENT AND TRADEMARK OFFICE
CERTIFICATE OF CORRECTION

PATENT NO. : 9,434,779 B2
APPLICATION NO. : 14/385578
DATED : September 6, 2016
INVENTOR(S) : Lee et al.

Page 1 of 1

It is certified that error appears in the above-identified patent and that said Letters Patent is hereby corrected as shown below:

In the Specification

At Column 1, Line 15 insert:
--GOVERNMENT SUPPORT
This invention was made with government support under AG032977, AG040019, and AG031679 awarded by the National Institutes of Health. The government has certain rights in this invention.--

Signed and Sealed this
Nineteenth Day of May, 2020

Andrei Iancu
*Director of the United States Patent and Trademark Office*

SEQUENCE LISTING

```
<160> NUMBER OF SEQ ID NOS: 26

<210> SEQ ID NO 1
<211> LENGTH: 407
<212> TYPE: PRT
<213> ORGANISM: Homo sapiens

<400> SEQUENCE: 1

Met Val Leu Ala Ala Pro Leu Leu Gly Phe Leu Leu Leu Ala Leu
1               5                   10                  15

Glu Leu Arg Pro Arg Gly Glu Ala Glu Gly Pro Ala Ala Ala
                20                  25                  30

Ala Ala Ala Ala Ala Ala Ala Gly Val Gly Gly Glu Arg Ser
        35                  40                  45

Ser Arg Pro Ala Pro Ser Val Ala Pro Glu Pro Asp Gly Cys Pro Val
50                  55                  60

Cys Val Trp Arg Gln His Ser Arg Glu Leu Arg Leu Glu Ser Ile Lys
65                  70                  75                  80

Ser Gln Ile Leu Ser Lys Leu Arg Leu Lys Glu Ala Pro Asn Ile Ser
                85                  90                  95

Arg Glu Val Val Lys Gln Leu Leu Pro Lys Ala Pro Pro Leu Gln Gln
                100                 105                 110

Ile Leu Asp Leu His Asp Phe Gln Gly Asp Ala Leu Gln Pro Glu Asp
            115                 120                 125

Phe Leu Glu Glu Asp Glu Tyr His Ala Thr Thr Glu Thr Val Ile Ser
        130                 135                 140

Met Ala Gln Glu Thr Asp Pro Ala Val Gln Thr Asp Gly Ser Pro Leu
145                 150                 155                 160

Cys Cys His Phe His Phe Ser Pro Lys Val Met Phe Thr Lys Val Leu
                165                 170                 175

Lys Ala Gln Leu Trp Val Tyr Leu Arg Pro Val Pro Arg Pro Ala Thr
                180                 185                 190

Val Tyr Leu Gln Ile Leu Arg Leu Lys Pro Leu Thr Gly Glu Gly Thr
            195                 200                 205

Ala Gly Gly Gly Gly Gly Arg Arg His Ile Arg Ile Arg Ser Leu
        210                 215                 220

Lys Ile Glu Leu His Ser Arg Ser Gly His Trp Gln Ser Ile Asp Phe
225                 230                 235                 240

Lys Gln Val Leu His Ser Trp Phe Arg Gln Pro Gln Ser Asn Trp Gly
                245                 250                 255

Ile Glu Ile Asn Ala Phe Asp Pro Ser Gly Thr Asp Leu Ala Val Thr
            260                 265                 270

Ser Leu Gly Pro Gly Ala Glu Gly Leu His Pro Phe Met Glu Leu Arg
        275                 280                 285

Val Leu Glu Asn Thr Lys Arg Ser Arg Arg Asn Leu Gly Leu Asp Cys
290                 295                 300

Asp Glu His Ser Ser Glu Ser Arg Cys Cys Arg Tyr Pro Leu Thr Val
305                 310                 315                 320

Asp Phe Glu Ala Phe Gly Trp Asp Trp Ile Ile Ala Pro Lys Arg Tyr
                325                 330                 335

Lys Ala Asn Tyr Cys Ser Gly Gln Cys Glu Tyr Met Phe Met Gln Lys
                340                 345                 350

Tyr Pro His Thr His Leu Val Gln Gln Ala Asn Pro Arg Gly Ser Ala
            355                 360                 365

Gly Pro Cys Cys Thr Pro Thr Lys Met Ser Pro Ile Asn Met Leu Tyr
```

```
                370                 375                 380
Phe Asn Asp Lys Gln Gln Ile Ile Tyr Gly Lys Ile Pro Gly Met Val
385                 390                 395                 400

Val Asp Arg Cys Gly Cys Ser
                405

<210> SEQ ID NO 2
<211> LENGTH: 383
<212> TYPE: PRT
<213> ORGANISM: Homo sapiens

<400> SEQUENCE: 2

Ala Glu Gly Pro Ala Ala Ala Ala Ala Ala Ala Ala Ala Ala Ala Ala
1               5                   10                  15

Ala Gly Val Gly Gly Glu Arg Ser Ser Arg Pro Ala Pro Ser Val Ala
                20                  25                  30

Pro Glu Pro Asp Gly Cys Pro Val Cys Val Trp Arg Gln His Ser Arg
            35                  40                  45

Glu Leu Arg Leu Glu Ser Ile Lys Ser Gln Ile Leu Ser Lys Leu Arg
    50                  55                  60

Leu Lys Glu Ala Pro Asn Ile Ser Arg Glu Val Val Lys Gln Leu Leu
65                  70                  75                  80

Pro Lys Ala Pro Pro Leu Gln Gln Ile Leu Asp Leu His Asp Phe Gln
                85                  90                  95

Gly Asp Ala Leu Gln Pro Glu Asp Phe Leu Glu Glu Asp Glu Tyr His
            100                 105                 110

Ala Thr Thr Glu Thr Val Ile Ser Met Ala Gln Glu Thr Asp Pro Ala
    115                 120                 125

Val Gln Thr Asp Gly Ser Pro Leu Cys Cys His Phe His Phe Ser Pro
130                 135                 140

Lys Val Met Phe Thr Lys Val Leu Lys Ala Gln Leu Trp Val Tyr Leu
145                 150                 155                 160

Arg Pro Val Pro Arg Pro Ala Thr Val Tyr Leu Gln Ile Leu Arg Leu
                165                 170                 175

Lys Pro Leu Thr Gly Glu Gly Thr Ala Gly Gly Gly Gly Gly Gly Arg
            180                 185                 190

Arg His Ile Arg Ile Arg Ser Leu Lys Ile Glu Leu His Ser Arg Ser
    195                 200                 205

Gly His Trp Gln Ser Ile Asp Phe Lys Gln Val Leu His Ser Trp Phe
210                 215                 220

Arg Gln Pro Gln Ser Asn Trp Gly Ile Glu Ile Asn Ala Phe Asp Pro
225                 230                 235                 240

Ser Gly Thr Asp Leu Ala Val Thr Ser Leu Gly Pro Gly Ala Glu Gly
                245                 250                 255

Leu His Pro Phe Met Glu Leu Arg Val Leu Glu Asn Thr Lys Arg Ser
            260                 265                 270

Arg Arg Asn Leu Gly Leu Asp Cys Asp Glu His Ser Ser Glu Ser Arg
    275                 280                 285

Cys Cys Arg Tyr Pro Leu Thr Val Asp Phe Glu Ala Phe Gly Trp Asp
290                 295                 300

Trp Ile Ile Ala Pro Lys Arg Tyr Lys Ala Asn Tyr Cys Ser Gly Gln
305                 310                 315                 320

Cys Glu Tyr Met Phe Met Gln Lys Tyr Pro His Thr His Leu Val Gln
                325                 330                 335
```

```
Gln Ala Asn Pro Arg Gly Ser Ala Gly Pro Cys Cys Thr Pro Thr Lys
            340                 345                 350

Met Ser Pro Ile Asn Met Leu Tyr Phe Asn Asp Lys Gln Gln Ile Ile
        355                 360                 365

Tyr Gly Lys Ile Pro Gly Met Val Val Asp Arg Cys Gly Cys Ser
    370                 375                 380

<210> SEQ ID NO 3
<211> LENGTH: 4260
<212> TYPE: DNA
<213> ORGANISM: Homo sapiens

<400> SEQUENCE: 3
tccccgcccc ccagtcctcc ctcccctccc ctccagcatg gtgctcgcgg cccgctgct       60 gctgggcttc ctgctcctcg ccctggagct gcggccccgg ggggaggcgg ccgagggccc     120
cgcggcggcg gcggcggcgg cggcggcggc ggcagcggcg ggggtcgggg gggagcgctc     180
cagccggcca gccccgtccg tggcgcccga gccggacggc tgccccgtgt gcgtttggcg     240
gcagcacagc cgcgagctgc gcctagagag catcaagtcg cagatcttga gcaaactgcg     300
gctcaaggag gcgcccaaca tcagccgcga ggtggtgaag cagctgctgc caaggcgcc      360 gccgctgcag cagatcctgg acctacacga cttccagggc gacgcgctgc agcccgagga     420
cttcctggag gaggacgagt accacgccac caccgagacc gtcattagca tggcccagga     480
gacggaccca gcagtacaga cagatggcag ccctctctgc tgccattttc acttcagccc     540
caaggtgatg ttcacaaagg tactgaaggc ccagctgtgg gtgtacctac ggcctgtacc     600
ccgcccagcc acagtctacc tgcagatctt gcgactaaaa cccctaactg gggaagggac     660
cgcaggggga gggggcggag gccggcgtca catccgtatc cgctcactga agattgagct     720
gcactcacgc tcaggccatt ggcagagcat cgacttcaag caagtgctac acagctggtt     780
ccgccagcca cagagcaact ggggcatcga gatcaacgcc tttgatccca gtggcacaga     840
cctggctgtc acctccctgg gccgggagc cgaggggctg catccattca tggagcttcg      900
agtcctagag aacacaaaac gttcccggcg gaacctgggt ctggactgcg acgagcactc     960
aagcgagtcc cgctgctgcc gatatcccct cacagtggac tttgaggctt cggctggga    1020 ctggatcatc gcacctaagc gctacaaggc caactactgc tccggccagt gcgagtacat    1080
gttcatgcaa aaatatccgc atacccattt ggtgcagcag gccaatccaa gaggctctgc    1140
tgggccctgt tgtacccccc ccaagatgtc cccaatcaac atgctctact tcaatgacaa    1200
gcagcagatt atctacggca agatccctgg catggtggtg gatcgctgtg gctgctctta    1260
aggtggggga tagaggatgc ctcccccaca gacccaccc caagacccct agccctgccc     1320 ccatccccc aagccctaga gctccctcca ctcttcccgc gaacatcaca ccgttccccg     1380
accaagccgt gtgcaataca acagagggag gcaggtggga attgagggtg agggttttgg    1440
gggaaagggg aagcagggc atagtcaggg tggggagtgt ttgaagtttg cagatgagaa     1500
ggtttgacaa aaagacagag agatgtagag acagtgatag acagagga acaaaaagag      1560 cagcagtgag aaggcaaaga gagaggcaga agagacagac gaggcagaga caaaacactg    1620
agaaagagac tgaaatggag taataaatga aagccccaca ccaagcctcc tttcttccac    1680 tgcaaggtg aggggcttgg tatagtttgg ggagatcccc tgactattca gtaggagaag     1740
aaatcaaaaa tccattcttt tctccttctc tccctccaac agtggccagg ggaagggaa     1800 gtgagggcag gggcaaaaag atttgggaat ttttattat ttatttattg tgacttttca    1860
```

```
tttttttggt atttggctttt actggaatag agggccccct gcccactgtg cccgtttat    1920 cccttattcc ccaaaccctg ctctccccaa cacctactca cttaagcact tgtataaagc    1980
ctccagggtt gggaatggga gtaaagggca agagggcgga cacatgaagt ttagtttcta    2040
acccatcatc accctaactc aaccttttct gagccaaatg gcttgaattg aagccagttg    2100
tcatggaaat agtaagaggt tagggtttaa gagctgggga tgcgggggtg ggagagagaa    2160
ccctcaacat ccaggatcta taatgaga gctactttaa accctcaggt ccaccctcat     2220
gatgctgagt tatttagcca gagggtgcag cctgcttatg cccaaattcc ctcagccaag    2280
agagagacca aagagcctct ggaatggccc tgctcccagc ctctatcttc aggtcaatta    2340
gagagagtat agagaccca gagtcccctg ggtctggaaa gcgttaggag aggtcaagaa    2400
aggagcagta aggaggctga aggttacagg gcatttgaat ccaaatcact gctctgggct    2460
agggaataga gccagcagac caaggtggga aggattctgg aaggggggaca ttttagtctc    2520 ctaaccccaa agctcaggggt ggaagagggg agaacaagga agcagagtgt ataattattt    2580 tttccttta tttttggaat ctaacagtac ctggcagcag ggaggggaaa gtacagtggg    2640
gaaaagcatc tgacaaggcc agttagaaca gaggatggga aggatggaga ctcccgggct    2700
tggaaggcta ggaagcaggc agagactggt tgccatttca agtcactagc taggcccatt    2760
cattcctccc acaaccctga cccattctcc tctggactca ctgtgcctca gtttcttccc    2820
ctcaatggaa tgaaaatga cagcacccgc cacagccaag agatgaattc tgagcactta    2880
ccacgggcac tttatggaca taaaatacct ctcgctgtgg gacagataac cagggcacca    2940
gagtagtggt gaaagagatgt gaggcttaag aggagtcaca ggcttcagag tacaagttcc    3000
cctctgcctc ccagctggac agtgcctaga agccaaggag ttgagaatct cctgatccac    3060
accctatcct tacttcacca ccaggcctct tggctccagg caagagctta gaggatgtca    3120
ggagaggtgg gggtaagaat cttcagcaaa actgtcactc taagtagagc cagcagttac    3180
gggtctgata aaacagtac tgaactaaag taaagcccaa gctggtgagc aaaactggat    3240
ggctcattct tcccaagagc atgactctcc cccttggcca gttggtggaa ggggcaaagg    3300
tatgtgacca cccttgagaa ggtgatgttg gtgagcttta acatcttatt cctattctta    3360
tagtgagaaa gtgaaacaag atctttcagt agaggaatgg gcagggctgt taggctcttc    3420
agcttgcctt cacccatata gcagctatgc taacccaag cctctctggc cctgttcttc     3480
atccttcctt ctgccccaat cctgaaggac aagacacacc cggccatcaa caccactcac    3540
atttccttgg tggaaggaaa ggaacagaga agtgaagaac agataccctcc ctccaaggtc    3600 aaatgcctcg tgatcttggc agagtaggga ttgggcaata agcatcaggt atcttccctc    3660
tacagattct agagagctgg ggcattaaat atggggaca cttagaatac agctccttaa     3720
ataccaccaa ataaagacct tgtgtgtgt gtggtgggtg ggggggggc agggggtcttt     3780 ctcttatgaa cataaatctg tgagctgaag tctcattccc ctgttcctcc ctaccccccaa   3840 agaggcacag agtgaaggga cttgggggc acagctcagc aacccagtgg gagttagcac     3900
cccctcccac cttatgatgt gtgtggacct ggccagtgcc cctctgaaca tatcattatt    3960
agtgtaatta tcatttattt tgtgtatttg tcacattgtg tgcatgacag cctttgttaa    4020
gggtgtctga ggagtatgga gctgacaggg gcattggaat gccaggaaag aacttcttca    4080
actgagatca aggcttcctg gagggaacca ctgcaaaaag gccatcaggc agttttcaag    4140
ttatgtgaca gagggcaaag acggccatag ggtgctctga gttttgggat ggtcacatga    4200
cacaatccag cacttgaacc tgaaaaaaaa aataaaagcg gtcaaagagt ttagaattca    4260
```

<210> SEQ ID NO 4
<211> LENGTH: 247
<212> TYPE: PRT
<213> ORGANISM: Homo sapiens

<400> SEQUENCE: 4

```
Met Arg Gly Asn Leu Ala Leu Val Gly Val Leu Ile Ser Leu Ala Phe
1               5                   10                  15

Leu Ser Leu Leu Pro Ser Gly His Pro Gln Pro Ala Gly Asp Asp Ala
            20                  25                  30

Cys Ser Val Gln Ile Leu Val Pro Gly Leu Lys Gly Asp Met Gly Asp
        35                  40                  45

Lys Gly Gln Lys Gly Ser Val Gly Arg His Gly Lys Ile Gly Pro Ile
    50                  55                  60

Gly Ser Lys Gly Glu Lys Gly Asp Ser Gly Asp Ile Gly Pro Pro Gly
65                  70                  75                  80

Pro Asn Gly Glu Pro Gly Leu Pro Cys Glu Cys Ser Gln Leu Arg Lys
                85                  90                  95

Ala Ile Gly Glu Met Asp Asn Gln Val Ser Gln Leu Thr Ser Glu Leu
            100                 105                 110

Lys Phe Ile Lys Asn Ala Val Ala Gly Val Arg Glu Thr Glu Ser Lys
        115                 120                 125

Ile Tyr Leu Leu Val Lys Glu Glu Lys Arg Tyr Ala Asp Ala Gln Leu
    130                 135                 140

Ser Cys Gln Gly Arg Gly Gly Thr Leu Ser Met Pro Lys Asp Glu Ala
145                 150                 155                 160

Ala Asn Gly Leu Met Ala Ala Tyr Leu Ala Gln Ala Gly Leu Ala Arg
                165                 170                 175

Val Phe Ile Gly Ile Asn Asp Leu Glu Lys Glu Gly Ala Phe Val Tyr
            180                 185                 190

Ser Asp His Ser Pro Met Arg Thr Phe Asn Lys Trp Arg Ser Gly Glu
        195                 200                 205

Pro Asn Asn Ala Tyr Asp Glu Glu Asp Cys Val Glu Met Val Ala Ser
    210                 215                 220

Gly Gly Trp Asn Asp Val Ala Cys His Thr Thr Met Tyr Phe Met Cys
225                 230                 235                 240

Glu Phe Asp Lys Glu Asn Met
                245
```

<210> SEQ ID NO 5
<211> LENGTH: 412
<212> TYPE: PRT
<213> ORGANISM: Homo sapiens

<400> SEQUENCE: 5

```
Met Gln Pro Ser Ser Leu Leu Pro Leu Ala Leu Cys Leu Leu Ala Ala
1               5                   10                  15

Pro Ala Ser Ala Leu Val Arg Ile Pro Leu His Lys Phe Thr Ser Ile
            20                  25                  30

Arg Arg Thr Met Ser Glu Val Gly Gly Ser Val Glu Asp Leu Ile Ala
        35                  40                  45

Lys Gly Pro Val Ser Lys Tyr Ser Gln Ala Val Pro Ala Val Thr Glu
    50                  55                  60

Gly Pro Ile Pro Glu Val Leu Lys Asn Tyr Met Asp Ala Gln Tyr Tyr
65                  70                  75                  80
```

```
Gly Glu Ile Gly Ile Gly Thr Pro Pro Gln Cys Phe Thr Val Val Phe
                85                  90                  95

Asp Thr Gly Ser Ser Asn Leu Trp Val Pro Ser Ile His Cys Lys Leu
            100                 105                 110

Leu Asp Ile Ala Cys Trp Ile His His Lys Tyr Asn Ser Asp Lys Ser
        115                 120                 125

Ser Thr Tyr Val Lys Asn Gly Thr Ser Phe Asp Ile His Tyr Gly Ser
    130                 135                 140

Gly Ser Leu Ser Gly Tyr Leu Ser Gln Asp Thr Val Ser Val Pro Cys
145                 150                 155                 160

Gln Ser Ala Ser Ala Ser Ala Leu Gly Gly Val Lys Val Glu Arg
                165                 170                 175

Gln Val Phe Gly Glu Ala Thr Lys Gln Pro Gly Ile Thr Phe Ile Ala
                180                 185                 190

Ala Lys Phe Asp Gly Ile Leu Gly Met Ala Tyr Pro Arg Ile Ser Val
        195                 200                 205

Asn Asn Val Leu Pro Val Phe Asp Asn Leu Met Gln Gln Lys Leu Val
    210                 215                 220

Asp Gln Asn Ile Phe Ser Phe Tyr Leu Ser Arg Asp Pro Asp Ala Gln
225                 230                 235                 240

Pro Gly Gly Glu Leu Met Leu Gly Gly Thr Asp Ser Lys Tyr Tyr Lys
                245                 250                 255

Gly Ser Leu Ser Tyr Leu Asn Val Thr Arg Lys Ala Tyr Trp Gln Val
            260                 265                 270

His Leu Asp Gln Val Glu Val Ala Ser Gly Leu Thr Leu Cys Lys Glu
        275                 280                 285

Gly Cys Glu Ala Ile Val Asp Thr Gly Thr Ser Leu Met Val Gly Pro
    290                 295                 300

Val Asp Glu Val Arg Glu Leu Gln Lys Ala Ile Gly Ala Val Pro Leu
305                 310                 315                 320

Ile Gln Gly Glu Tyr Met Ile Pro Cys Glu Lys Val Ser Thr Leu Pro
                325                 330                 335

Ala Ile Thr Leu Lys Leu Gly Gly Lys Gly Tyr Lys Leu Ser Pro Glu
            340                 345                 350

Asp Tyr Thr Leu Lys Val Ser Gln Ala Gly Lys Thr Leu Cys Leu Ser
        355                 360                 365

Gly Phe Met Gly Met Asp Ile Pro Pro Pro Ser Gly Pro Leu Trp Ile
    370                 375                 380

Leu Gly Asp Val Phe Ile Gly Arg Tyr Tyr Thr Val Phe Asp Arg Asp
385                 390                 395                 400

Asn Asn Arg Val Gly Phe Ala Glu Ala Ala Arg Leu
                405                 410

<210> SEQ ID NO 6
<211> LENGTH: 224
<212> TYPE: PRT
<213> ORGANISM: Homo sapiens

<400> SEQUENCE: 6

Met Val Ala Ala Val Leu Leu Gly Leu Ser Trp Leu Cys Ser Pro Leu
1               5                   10                  15

Gly Ala Leu Val Leu Asp Phe Asn Asn Ile Arg Ser Ser Ala Asp Leu
            20                  25                  30

His Gly Ala Arg Lys Gly Ser Gln Cys Leu Ser Asp Thr Asp Cys Asn
```

```
                35                  40                  45
Thr Arg Lys Phe Cys Leu Gln Pro Arg Asp Glu Lys Pro Phe Cys Ala
 50                  55                  60

Thr Cys Arg Gly Leu Arg Arg Cys Gln Arg Asp Ala Met Cys Cys
 65                  70                  75                  80

Pro Gly Thr Leu Cys Val Asn Asp Val Cys Thr Thr Met Glu Asp Ala
                 85                  90                  95

Thr Pro Ile Leu Glu Arg Gln Leu Asp Glu Gln Asp Gly Thr His Ala
            100                 105                 110

Glu Gly Thr Thr Gly His Pro Val Gln Glu Asn Gln Pro Lys Arg Lys
        115                 120                 125

Pro Ser Ile Lys Lys Ser Gln Gly Arg Lys Gly Gln Glu Gly Glu Ser
130                 135                 140

Cys Leu Arg Thr Phe Asp Cys Gly Pro Gly Leu Cys Cys Ala Arg His
145                 150                 155                 160

Phe Trp Thr Lys Ile Cys Lys Pro Val Leu Leu Glu Gly Gln Val Cys
                165                 170                 175

Ser Arg Arg Gly His Lys Asp Thr Ala Gln Ala Pro Glu Ile Phe Gln
            180                 185                 190

Arg Cys Asp Cys Gly Pro Gly Leu Leu Cys Arg Ser Gln Leu Thr Ser
        195                 200                 205

Asn Arg Gln His Ala Arg Leu Arg Val Cys Gln Lys Ile Glu Lys Leu
210                 215                 220

<210> SEQ ID NO 7
<211> LENGTH: 864
<212> TYPE: PRT
<213> ORGANISM: Homo sapiens

<400> SEQUENCE: 7

Met Thr Thr Glu Lys Ser Leu Val Thr Glu Ala Glu Asn Ser Gln His
  1               5                  10                  15

Gln Gln Lys Glu Glu Gly Glu Ala Ile Asn Ser Gly Gln Gln Glu
             20                  25                  30

Pro Gln Gln Glu Glu Ser Cys Gln Thr Ala Ala Glu Gly Asp Asn Trp
         35                  40                  45

Cys Glu Gln Lys Leu Lys Ala Ser Asn Gly Asp Thr Pro Thr His Glu
 50                  55                  60

Asp Leu Thr Lys Asn Lys Glu Arg Thr Ser Glu Ser Arg Gly Leu Ser
 65                  70                  75                  80

Arg Leu Phe Ser Ser Phe Leu Lys Arg Pro Lys Ser Gln Val Ser Glu
                 85                  90                  95

Glu Glu Gly Lys Glu Val Glu Ser Asp Lys Glu Lys Gly Glu Gly Gly
            100                 105                 110

Gln Lys Glu Ile Glu Phe Gly Thr Ser Leu Asp Glu Ile Ile Leu
        115                 120                 125

Lys Ala Pro Ile Ala Ala Pro Glu Pro Glu Leu Lys Thr Asp Pro Ser
130                 135                 140

Leu Asp Leu His Ser Leu Ser Ser Ala Glu Thr Gln Pro Ala Gln Glu
145                 150                 155                 160

Glu Leu Arg Glu Asp Pro Asp Phe Glu Ile Lys Glu Gly Glu Gly Leu
                165                 170                 175

Glu Glu Cys Ser Lys Ile Glu Val Lys Glu Glu Ser Pro Gln Ser Lys
            180                 185                 190
```

```
Ala Glu Thr Glu Leu Lys Ala Ser Gln Lys Pro Ile Arg Lys His Arg
        195                 200                 205
Asn Met His Cys Lys Val Ser Leu Leu Asp Asp Thr Val Tyr Glu Cys
        210                 215                 220
Val Val Glu Lys His Ala Lys Gly Gln Asp Leu Leu Lys Arg Val Cys
225                 230                 235                 240
Glu His Leu Asn Leu Leu Glu Asp Tyr Phe Gly Leu Ala Ile Trp
                245                 250                 255
Asp Asn Ala Thr Ser Lys Thr Trp Leu Asp Ser Ala Lys Glu Ile Lys
                260                 265                 270
Lys Gln Val Arg Gly Val Pro Trp Asn Phe Thr Phe Asn Val Lys Phe
        275                 280                 285
Tyr Pro Pro Asp Pro Ala Gln Leu Thr Glu Asp Ile Thr Arg Tyr Tyr
        290                 295                 300
Leu Cys Leu Gln Leu Arg Gln Asp Ile Val Ala Gly Arg Leu Pro Cys
305                 310                 315                 320
Ser Phe Ala Thr Leu Ala Leu Leu Gly Ser Tyr Thr Ile Gln Ser Glu
                325                 330                 335
Leu Gly Asp Tyr Asp Pro Glu Leu His Gly Val Asp Tyr Val Ser Asp
                340                 345                 350
Phe Lys Leu Ala Pro Asn Gln Thr Lys Glu Leu Glu Glu Lys Val Met
        355                 360                 365
Glu Leu His Lys Ser Tyr Arg Ser Met Thr Pro Ala Gln Ala Asp Leu
        370                 375                 380
Glu Phe Leu Glu Asn Ala Lys Lys Leu Ser Met Tyr Gly Val Asp Leu
385                 390                 395                 400
His Lys Ala Lys Asp Leu Glu Gly Val Asp Ile Ile Leu Gly Val Cys
                405                 410                 415
Ser Ser Gly Leu Leu Val Tyr Lys Asp Lys Leu Arg Ile Asn Arg Phe
                420                 425                 430
Pro Trp Pro Lys Val Leu Lys Ile Ser Tyr Lys Arg Ser Ser Phe Phe
        435                 440                 445
Ile Lys Ile Arg Pro Gly Glu Gln Glu Gln Tyr Glu Ser Thr Ile Gly
        450                 455                 460
Phe Lys Leu Pro Ser Tyr Arg Ala Ala Lys Lys Leu Trp Lys Val Cys
465                 470                 475                 480
Val Glu His His Thr Phe Phe Arg Leu Thr Ser Asp Thr Ile Pro
                485                 490                 495
Lys Ser Lys Phe Leu Ala Leu Gly Ser Lys Phe Arg Tyr Ser Gly Arg
        500                 505                 510
Thr Gln Ala Gln Thr Arg Gln Ala Ser Ala Leu Ile Asp Arg Pro Ala
        515                 520                 525
Pro His Phe Glu Arg Thr Ala Ser Lys Arg Ala Ser Arg Ser Leu Asp
        530                 535                 540
Gly Ala Ala Ala Val Asp Ser Asp Arg Ser Pro Arg Pro Thr Ser
545                 550                 555                 560
Ala Pro Ala Ile Thr Gln Gly Gln Val Ala Glu Gly Gly Val Leu Asp
                565                 570                 575
Ala Ser Ala Lys Lys Thr Val Val Pro Lys Ala Gln Lys Glu Thr Val
                580                 585                 590
Lys Ala Glu Val Lys Lys Glu Asp Glu Pro Pro Glu Gln Ala Glu Pro
        595                 600                 605
Glu Pro Thr Glu Ala Trp Lys Val Glu Lys Thr His Ile Glu Val Thr
```

```
            610                 615                 620
Val Pro Thr Ser Asn Gly Asp Gln Thr Gln Lys Leu Ala Glu Lys Thr
625                 630                 635                 640

Glu Asp Leu Ile Arg Met Arg Lys Lys Arg Glu Arg Leu Asp Gly
                645                 650                 655

Glu Asn Ile Tyr Ile Arg His Ser Asn Leu Met Leu Glu Asp Leu Asp
                660                 665                 670

Lys Ser Gln Glu Glu Ile Lys Lys His His Ala Ser Ile Ser Glu Leu
                675                 680                 685

Lys Lys Asn Phe Met Glu Ser Val Pro Glu Pro Arg Pro Ser Glu Trp
            690                 695                 700

Asp Lys Arg Leu Ser Thr His Ser Pro Phe Arg Thr Leu Asn Ile Asn
705                 710                 715                 720

Gly Gln Ile Pro Thr Gly Glu Gly Pro Pro Leu Val Lys Thr Gln Thr
                725                 730                 735

Val Thr Ile Ser Asp Asn Ala Asn Ala Val Lys Ser Glu Ile Pro Thr
                740                 745                 750

Lys Asp Val Pro Ile Val His Thr Glu Thr Lys Thr Ile Thr Tyr Glu
            755                 760                 765

Ala Ala Gln Thr Asp Asp Asn Ser Gly Asp Leu Asp Pro Gly Val Leu
770                 775                 780

Leu Thr Ala Gln Thr Ile Thr Ser Glu Thr Pro Ser Ser Thr Thr Thr
785                 790                 795                 800

Thr Gln Ile Thr Lys Thr Val Lys Gly Gly Ile Ser Glu Thr Arg Ile
                805                 810                 815

Glu Lys Arg Ile Val Ile Thr Gly Asp Ala Asp Ile Asp His Asp Gln
                820                 825                 830

Val Leu Val Gln Ala Ile Lys Glu Ala Lys Gln His Pro Asp Met
            835                 840                 845

Ser Val Thr Lys Val Val Val His Gln Glu Thr Glu Ile Ala Asp Glu
850                 855                 860

<210> SEQ ID NO 8
<211> LENGTH: 282
<212> TYPE: PRT
<213> ORGANISM: Homo sapiens

<400> SEQUENCE: 8

Met Ala Leu Lys Gln Ile Ser Ser Asn Lys Cys Phe Gly Gly Leu Gln
1               5                   10                  15

Lys Val Phe Glu His Asp Ser Val Glu Leu Asn Cys Lys Met Lys Phe
                20                  25                  30

Ala Val Tyr Leu Pro Pro Lys Ala Glu Thr Gly Lys Cys Pro Ala Leu
                35                  40                  45

Tyr Trp Leu Ser Gly Leu Thr Cys Thr Glu Gln Asn Phe Ile Ser Lys
            50                  55                  60

Ser Gly Tyr His Gln Ser Ala Ser Glu His Gly Leu Val Val Ile Ala
65                  70                  75                  80

Pro Asp Thr Ser Pro Arg Gly Cys Asn Ile Lys Gly Glu Asp Glu Ser
                85                  90                  95

Trp Asp Phe Gly Thr Gly Ala Gly Phe Tyr Val Asp Ala Thr Glu Asp
                100                 105                 110

Pro Trp Lys Thr Asn Tyr Arg Met Tyr Ser Tyr Val Thr Glu Glu Leu
            115                 120                 125
```

```
Pro Gln Leu Ile Asn Ala Asn Phe Pro Val Asp Pro Gln Arg Met Ser
130                 135                 140

Ile Phe Gly His Ser Met Gly Gly His Gly Ala Leu Ile Cys Ala Leu
145                 150                 155                 160

Lys Asn Pro Gly Lys Tyr Lys Ser Val Ser Ala Phe Ala Pro Ile Cys
                165                 170                 175

Asn Pro Val Leu Cys Pro Trp Gly Lys Lys Ala Phe Ser Gly Tyr Leu
            180                 185                 190

Gly Thr Asp Gln Ser Lys Trp Lys Ala Tyr Asp Ala Thr His Leu Val
        195                 200                 205

Lys Ser Tyr Pro Gly Ser Gln Leu Asp Ile Leu Ile Asp Gln Gly Lys
210                 215                 220

Asp Asp Gln Phe Leu Leu Asp Gly Gln Leu Leu Pro Asp Asn Phe Ile
225                 230                 235                 240

Ala Ala Cys Thr Glu Lys Lys Ile Pro Val Val Phe Arg Leu Gln Glu
                245                 250                 255

Gly Tyr Asp His Ser Tyr Tyr Phe Ile Ala Thr Phe Ile Thr Asp His
            260                 265                 270

Ile Arg His His Ala Lys Tyr Leu Asn Ala
        275                 280

<210> SEQ ID NO 9
<211> LENGTH: 147
<212> TYPE: PRT
<213> ORGANISM: Homo sapiens

<400> SEQUENCE: 9

Met Val His Leu Thr Pro Glu Glu Lys Ser Ala Val Thr Ala Leu Trp
1               5                   10                  15

Gly Lys Val Asn Val Asp Glu Val Gly Gly Glu Ala Leu Gly Arg Leu
                20                  25                  30

Leu Val Val Tyr Pro Trp Thr Gln Arg Phe Phe Glu Ser Phe Gly Asp
            35                  40                  45

Leu Ser Thr Pro Asp Ala Val Met Gly Asn Pro Lys Val Lys Ala His
        50                  55                  60

Gly Lys Lys Val Leu Gly Ala Phe Ser Asp Gly Leu Ala His Leu Asp
65                  70                  75                  80

Asn Leu Lys Gly Thr Phe Ala Thr Leu Ser Glu Leu His Cys Asp Lys
                85                  90                  95

Leu His Val Asp Pro Glu Asn Phe Arg Leu Leu Gly Asn Val Leu Val
            100                 105                 110

Cys Val Leu Ala His His Phe Gly Lys Glu Phe Thr Pro Pro Val Gln
        115                 120                 125

Ala Ala Tyr Gln Lys Val Val Ala Gly Val Ala Asn Ala Leu Ala His
    130                 135                 140

Lys Tyr His
145

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
```
tcgtcttggc cttttggct                                              19

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tccaggtggt ctagcaggtt ct                                          22

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
agggagaaca cggcatcatt                                             20

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gacagcacct tcaggagat                                              19

<210> SEQ ID NO 14
<211> LENGTH: 109
<212> TYPE: PRT
<213> ORGANISM: Homo sapiens

<400> SEQUENCE: 14

Asn Leu Gly Leu Asp Cys Asp Glu His Ser Ser Glu Ser Arg Cys Cys
1               5                   10                  15

Arg Tyr Pro Leu Thr Val Asp Phe Glu Ala Phe Gly Trp Asp Trp Ile
            20                  25                  30

Ile Ala Pro Lys Arg Tyr Lys Ala Asn Tyr Cys Ser Gly Gln Cys Glu
        35                  40                  45

Tyr Met Phe Met Gln Lys Tyr Pro His Thr His Leu Val Gln Gln Ala
    50                  55                  60

Asn Pro Arg Gly Ser Ala Gly Pro Cys Cys Thr Pro Thr Lys Met Ser
65                  70                  75                  80

Pro Ile Asn Met Leu Tyr Phe Asn Asp Lys Gln Gln Ile Ile Tyr Gly
                85                  90                  95

Lys Ile Pro Gly Met Val Val Asp Arg Cys Gly Cys Ser
            100                 105

<210> SEQ ID NO 15
<211> LENGTH: 274
<212> TYPE: PRT
<213> ORGANISM: Homo sapiens

<400> SEQUENCE: 15

Ala Glu Gly Pro Ala Ala Ala Ala Ala Ala Ala Ala Ala Ala Ala

```
  1               5                  10                  15
Ala Gly Val Gly Gly Glu Arg Ser Ser Arg Pro Ala Pro Ser Val Ala
             20                  25                  30
Pro Glu Pro Asp Gly Cys Pro Val Cys Val Trp Arg Gln His Ser Arg
             35                  40                  45
Glu Leu Arg Leu Glu Ser Ile Lys Ser Gln Ile Leu Ser Lys Leu Arg
 50                  55                  60
Leu Lys Glu Ala Pro Asn Ile Ser Arg Glu Val Val Lys Gln Leu Leu
 65                  70                  75                  80
Pro Lys Ala Pro Pro Leu Gln Gln Ile Leu Asp Leu His Asp Phe Gln
             85                  90                  95
Gly Asp Ala Leu Gln Pro Glu Asp Phe Leu Glu Glu Asp Glu Tyr His
             100                 105                 110
Ala Thr Thr Glu Thr Val Ile Ser Met Ala Gln Glu Thr Asp Pro Ala
             115                 120                 125
Val Gln Thr Asp Gly Ser Pro Leu Cys Cys His Phe His Phe Ser Pro
 130                 135                 140
Lys Val Met Phe Thr Lys Val Leu Lys Ala Gln Leu Trp Val Tyr Leu
 145                 150                 155                 160
Arg Pro Val Pro Arg Pro Ala Thr Val Tyr Leu Gln Ile Leu Arg Leu
             165                 170                 175
Lys Pro Leu Thr Gly Glu Gly Thr Ala Gly Gly Gly Gly Gly Gly Arg
             180                 185                 190
Arg His Ile Arg Ile Arg Ser Leu Lys Ile Glu Leu His Ser Arg Ser
             195                 200                 205
Gly His Trp Gln Ser Ile Asp Phe Lys Gln Val Leu His Ser Trp Phe
             210                 215                 220
Arg Gln Pro Gln Ser Asn Trp Gly Ile Glu Ile Asn Ala Phe Asp Pro
 225                 230                 235                 240
Ser Gly Thr Asp Leu Ala Val Thr Ser Leu Gly Pro Gly Ala Glu Gly
             245                 250                 255
Leu His Pro Phe Met Glu Leu Arg Val Leu Glu Asn Thr Lys Arg Ser
             260                 265                 270
Arg Arg

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tggaacaacc cggtaaagag t                                           21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
caccaggggc ataatgagca g                                           21
```

```
<210> SEQ ID NO 18
<211> LENGTH: 337
<212> TYPE: PRT
<213> ORGANISM: Homo sapiens

<400> SEQUENCE: 18

Cys Asn Ala Cys Thr Trp Arg Gln Asn Thr Lys Ser Ser Arg Ile Glu
1               5                   10                  15

Ala Ile Lys Ile Gln Ile Leu Ser Lys Leu Arg Leu Glu Thr Ala Pro
                20                  25                  30

Asn Ile Ser Lys Asp Val Ile Arg Gln Leu Leu Pro Lys Ala Pro Pro
            35                  40                  45

Leu Arg Glu Leu Ile Asp Gln Tyr Asp Val Gln Arg Asp Asp Ser Ser
    50                  55                  60

Asp Gly Ser Leu Glu Asp Asp Tyr His Ala Thr Thr Glu Thr Ile
65                  70                  75                  80

Ile Thr Met Pro Thr Glu Ser Asp Phe Leu Met Gln Val Asp Gly Lys
                85                  90                  95

Pro Lys Cys Cys Phe Phe Lys Phe Ser Ser Lys Ile Gln Tyr Asn Lys
            100                 105                 110

Val Val Lys Ala Gln Leu Trp Ile Tyr Leu Arg Pro Val Glu Thr Pro
        115                 120                 125

Thr Thr Val Phe Val Gln Ile Leu Arg Leu Ile Lys Pro Met Lys Asp
130                 135                 140

Gly Thr Arg Tyr Thr Gly Ile Arg Ser Leu Lys Leu Asp Met Asn Pro
145                 150                 155                 160

Gly Thr Gly Ile Trp Gln Ser Ile Asp Val Lys Thr Val Leu Gln Asn
                165                 170                 175

Trp Leu Lys Gln Pro Glu Ser Asn Leu Gly Ile Glu Ile Lys Ala Leu
            180                 185                 190

Asp Glu Asn Gly His Asp Leu Ala Val Thr Phe Pro Gly Pro Gly Glu
        195                 200                 205

Asp Gly Leu Asn Pro Phe Leu Glu Val Lys Val Thr Asp Thr Pro Lys
210                 215                 220

Arg Ser Arg Arg Asp Phe Gly Leu Asp Cys Asp Glu His Ser Thr Glu
225                 230                 235                 240

Ser Arg Cys Cys Arg Tyr Pro Leu Thr Val Asp Phe Glu Ala Phe Gly
                245                 250                 255

Trp Asp Trp Ile Ile Ala Pro Lys Arg Tyr Lys Ala Asn Tyr Cys Ser
            260                 265                 270

Gly Glu Cys Glu Phe Val Phe Leu Gln Lys Tyr Pro His Thr His Leu
        275                 280                 285

Val His Gln Ala Asn Pro Arg Gly Ser Ala Gly Pro Cys Cys Thr Pro
290                 295                 300

Thr Lys Met Ser Pro Ile Asn Met Leu Tyr Phe Asn Gly Lys Glu Gln
305                 310                 315                 320

Ile Ile Tyr Gly Lys Ile Pro Ala Met Val Val Asp Arg Cys Gly Cys
                325                 330                 335

Ser

<210> SEQ ID NO 19
<211> LENGTH: 361
<212> TYPE: PRT
<213> ORGANISM: Mus sp.

<400> SEQUENCE: 19
```

```
Arg Ser Ser Arg Pro Ala Pro Ser Ala Pro Pro Glu Pro Asp Gly Cys
  1               5                  10                  15

Pro Val Cys Val Trp Arg Gln His Ser Arg Glu Leu Arg Leu Glu Ser
             20                  25                  30

Ile Lys Ser Gln Ile Leu Ser Lys Leu Arg Leu Lys Glu Ala Pro Asn
         35                  40                  45

Ile Ser Arg Glu Val Val Lys Gln Leu Leu Pro Lys Ala Pro Pro Leu
     50                  55                  60

Gln Gln Ile Leu Asp Leu His Asp Phe Gln Gly Asp Ala Leu Gln Pro
 65                  70                  75                  80

Glu Asp Phe Leu Glu Glu Asp Glu Tyr His Ala Thr Thr Glu Thr Val
                 85                  90                  95

Ile Ser Met Ala Gln Glu Thr Asp Pro Ala Val Gln Thr Asp Gly Ser
            100                 105                 110

Pro Leu Cys Cys His Phe His Phe Ser Pro Lys Val Met Phe Thr Lys
        115                 120                 125

Val Leu Lys Ala Gln Leu Trp Val Tyr Leu Arg Pro Val Pro Arg Pro
    130                 135                 140

Ala Thr Val Tyr Leu Gln Ile Leu Arg Leu Lys Pro Leu Thr Gly Glu
145                 150                 155                 160

Gly Thr Ala Gly Gly Gly Gly Gly Arg Arg His Ile Arg Ile Arg
                165                 170                 175

Ser Leu Lys Ile Glu Leu His Ser Arg Ser Gly His Trp Gln Ser Ile
                180                 185                 190

Asp Phe Lys Gln Val Leu His Ser Trp Phe Arg Gln Pro Gln Ser Asn
                195                 200                 205

Trp Gly Ile Glu Ile Asn Ala Phe Asp Pro Ser Gly Thr Asp Leu Ala
210                 215                 220

Val Thr Ser Leu Gly Pro Gly Ala Glu Gly Leu His Pro Phe Met Glu
225                 230                 235                 240

Leu Arg Val Leu Glu Asn Thr Lys Arg Ser Arg Arg Asn Leu Gly Leu
                245                 250                 255

Asp Cys Asp Glu His Ser Ser Glu Ser Arg Cys Cys Arg Tyr Pro Leu
                260                 265                 270

Thr Val Asp Phe Glu Ala Phe Gly Trp Asp Trp Ile Ile Ala Pro Lys
                275                 280                 285

Arg Tyr Lys Ala Asn Tyr Cys Ser Gly Gln Cys Glu Tyr Met Phe Met
    290                 295                 300

Gln Lys Tyr Pro His Thr His Leu Val Gln Gln Ala Asn Pro Arg Gly
305                 310                 315                 320

Ser Ala Gly Pro Cys Cys Thr Pro Thr Lys Met Ser Pro Ile Asn Met
                325                 330                 335

Leu Tyr Phe Asn Asp Lys Gln Gln Ile Ile Tyr Gly Lys Ile Pro Gly
                340                 345                 350

Met Val Val Asp Arg Cys Gly Cys Ser
                355                 360

<210> SEQ ID NO 20
<211> LENGTH: 147
<212> TYPE: PRT
<213> ORGANISM: Homo sapiens

<400> SEQUENCE: 20

Met Gly His Phe Thr Glu Glu Asp Lys Ala Thr Ile Thr Ser Leu Trp
```

```
              1               5                  10                 15
Gly Lys Val Asn Val Glu Asp Ala Gly Gly Glu Thr Leu Gly Arg Leu
                     20                 25                 30

Leu Val Val Tyr Pro Trp Thr Gln Arg Phe Phe Asp Ser Phe Gly Asn
                     35                 40                 45

Leu Ser Ser Ala Ser Ala Ile Met Gly Asn Pro Lys Val Lys Ala His
                     50                 55                 60

Gly Lys Lys Val Leu Thr Ser Leu Gly Asp Ala Thr Lys His Leu Asp
 65                  70                 75                      80

Asp Leu Lys Gly Thr Phe Ala Gln Leu Ser Glu Leu His Cys Asp Lys
                     85                 90                 95

Leu His Val Asp Pro Glu Asn Phe Lys Leu Leu Gly Asn Val Leu Val
                     100                105                110

Thr Val Leu Ala Ile His Phe Gly Lys Glu Phe Thr Pro Glu Val Gln
                     115                120                125

Ala Ser Trp Gln Lys Met Val Thr Ala Val Ala Ser Ala Leu Ser Ser
                     130                135                140

Arg Tyr His
145

<210> SEQ ID NO 21
<211> LENGTH: 570
<212> TYPE: PRT
<213> ORGANISM: Homo sapiens

<400> SEQUENCE: 21

Met Thr Leu Leu Trp Cys Val Val Ser Leu Tyr Phe Tyr Gly Ile Leu
 1               5                  10                 15

Gln Ser Asp Ala Ser Glu Arg Cys Asp Asp Trp Gly Leu Asp Thr Met
                     20                 25                 30

Arg Gln Ile Gln Val Phe Glu Asp Glu Pro Ala Arg Ile Lys Cys Pro
                     35                 40                 45

Leu Phe Glu His Phe Leu Lys Phe Asn Tyr Ser Thr Ala His Ser Ala
                     50                 55                 60

Gly Leu Thr Leu Ile Trp Tyr Trp Thr Arg Gln Asp Arg Asp Leu Glu
 65                  70                 75                      80

Glu Pro Ile Asn Phe Arg Leu Pro Glu Asn Arg Ile Ser Lys Glu Lys
                     85                 90                 95

Asp Val Leu Trp Phe Arg Pro Thr Leu Leu Asn Asp Thr Gly Asn Tyr
                     100                105                110

Thr Cys Met Leu Arg Asn Thr Thr Tyr Cys Ser Lys Val Ala Phe Pro
                     115                120                125

Leu Glu Val Val Gln Lys Asp Ser Cys Phe Asn Ser Pro Met Lys Leu
                     130                135                140

Pro Val His Lys Leu Tyr Ile Glu Tyr Gly Ile Gln Arg Ile Thr Cys
145                  150                155                160

Pro Asn Val Asp Gly Tyr Phe Pro Ser Ser Val Lys Pro Thr Ile Thr
                     165                170                175

Trp Tyr Met Gly Cys Tyr Lys Ile Gln Asn Phe Asn Asn Val Ile Pro
                     180                185                190

Glu Gly Met Asn Leu Ser Phe Leu Ile Ala Leu Ile Ser Asn Asn Gly
                     195                200                205

Asn Tyr Thr Cys Val Val Thr Tyr Pro Glu Asn Gly Arg Thr Phe His
                     210                215                220
```

```
Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Thr Val Thr Ile Asn Glu Ser Ile Ser His
    290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
            340                 345                 350

Ala Pro Arg Tyr Thr Val Glu Leu Ala Cys Gly Phe Gly Ala Thr Val
        355                 360                 365

Leu Leu Val Val Ile Leu Ile Val Val Tyr His Val Tyr Trp Leu Glu
    370                 375                 380

Met Val Leu Phe Tyr Arg Ala His Phe Gly Thr Asp Glu Thr Ile Leu
385                 390                 395                 400

Asp Gly Lys Glu Tyr Asp Ile Tyr Val Ser Tyr Ala Arg Asn Ala Glu
                405                 410                 415

Glu Glu Glu Phe Val Leu Leu Thr Leu Arg Gly Val Leu Glu Asn Glu
            420                 425                 430

Phe Gly Tyr Lys Leu Cys Ile Phe Asp Arg Asp Ser Leu Pro Gly Gly
        435                 440                 445

Ile Val Thr Asp Glu Thr Leu Ser Phe Ile Gln Lys Ser Arg Arg Leu
    450                 455                 460

Leu Val Val Leu Ser Pro Asn Tyr Val Leu Gln Gly Thr Gln Ala Leu
465                 470                 475                 480

Leu Glu Leu Lys Ala Gly Leu Glu Asn Met Ala Ser Arg Gly Asn Ile
                485                 490                 495

Asn Val Ile Leu Val Gln Tyr Lys Ala Val Lys Glu Thr Lys Val Lys
            500                 505                 510

Glu Leu Lys Arg Ala Lys Thr Val Leu Thr Val Ile Lys Trp Lys Gly
        515                 520                 525

Glu Lys Ser Lys Tyr Pro Gln Gly Arg Phe Trp Lys Gln Leu Gln Val
    530                 535                 540

Ala Met Pro Val Lys Lys Ser Pro Arg Arg Ser Ser Ser Asp Glu Gln
545                 550                 555                 560

Gly Leu Ser Tyr Ser Ser Leu Lys Asn Val
                565                 570

<210> SEQ ID NO 22
<211> LENGTH: 216
<212> TYPE: PRT
<213> ORGANISM: Homo sapiens

<400> SEQUENCE: 22

Met Gly Trp Ile Arg Gly Arg Arg Ser Arg His Ser Trp Glu Met Ser
1               5                   10                  15

Glu Phe His Asn Tyr Asn Leu Asp Leu Lys Lys Ser Asp Phe Ser Thr
            20                  25                  30
```

Arg Trp Gln Lys Gln Arg Cys Pro Val Val Lys Ser Lys Cys Arg Glu
                35                  40                  45

Asn Ala Ser Pro Phe Phe Cys Cys Phe Ile Ala Val Ala Met Gly
 50                  55                  60

Ile Arg Phe Ile Ile Met Val Thr Ile Trp Ser Ala Val Phe Leu Asn
 65                  70                  75                  80

Ser Leu Phe Asn Gln Glu Val Gln Ile Pro Leu Thr Glu Ser Tyr Cys
                    85                  90                  95

Gly Pro Cys Pro Lys Asn Trp Ile Cys Tyr Lys Asn Asn Cys Tyr Gln
                100                 105                 110

Phe Phe Asp Glu Ser Lys Asn Trp Tyr Glu Ser Gln Ala Ser Cys Met
                115                 120                 125

Ser Gln Asn Ala Ser Leu Leu Lys Val Tyr Ser Lys Glu Asp Gln Asp
130                 135                 140

Leu Leu Lys Leu Val Lys Ser Tyr His Trp Met Gly Leu Val His Ile
145                 150                 155                 160

Pro Thr Asn Gly Ser Trp Gln Trp Glu Asp Gly Ser Ile Leu Ser Pro
                165                 170                 175

Asn Leu Leu Thr Ile Ile Glu Met Gln Lys Gly Asp Cys Ala Leu Tyr
                180                 185                 190

Ala Ser Ser Phe Lys Gly Tyr Ile Glu Asn Cys Ser Thr Pro Asn Thr
                195                 200                 205

Tyr Ile Cys Met Gln Arg Thr Val
210                 215

<210> SEQ ID NO 23
<211> LENGTH: 192
<212> TYPE: PRT
<213> ORGANISM: Homo sapiens

<400> SEQUENCE: 23

Met Gln Ala Ile Lys Cys Val Val Val Gly Asp Gly Ala Val Gly Lys
 1                   5                  10                  15

Thr Cys Leu Leu Ile Ser Tyr Thr Thr Asn Ala Phe Pro Gly Glu Tyr
                20                  25                  30

Ile Pro Thr Val Phe Asp Asn Tyr Ser Ala Asn Val Met Val Asp Gly
                35                  40                  45

Lys Pro Val Asn Leu Gly Leu Trp Asp Thr Ala Gly Gln Glu Asp Tyr
 50                  55                  60

Asp Arg Leu Arg Pro Leu Ser Tyr Pro Gln Thr Asp Val Phe Leu Ile
 65                  70                  75                  80

Cys Phe Ser Leu Val Ser Pro Ala Ser Phe Glu Asn Val Arg Ala Lys
                    85                  90                  95

Trp Tyr Pro Glu Val Arg His His Cys Pro Asn Thr Pro Ile Ile Leu
                100                 105                 110

Val Gly Thr Lys Leu Asp Leu Arg Asp Asp Lys Asp Thr Ile Glu Lys
                115                 120                 125

Leu Lys Glu Lys Lys Leu Thr Pro Ile Thr Tyr Pro Gln Gly Leu Ala
130                 135                 140

Met Ala Lys Glu Ile Gly Ala Val Lys Tyr Leu Glu Cys Ser Ala Leu
145                 150                 155                 160

Thr Gln Arg Gly Leu Lys Thr Val Phe Asp Glu Ala Ile Arg Ala Val
                165                 170                 175

Leu Cys Pro Pro Pro Val Lys Lys Arg Lys Arg Lys Cys Leu Leu Leu

<210> SEQ ID NO 24
<211> LENGTH: 216
<212> TYPE: PRT
<213> ORGANISM: Homo sapiens

<400> SEQUENCE: 24

Met Ala Ala Gln Gly Glu Pro Gln Val Gln Phe Lys Leu Val Leu Val
1               5                   10                  15
Gly Asp Gly Gly Thr Gly Lys Thr Thr Phe Val Lys Arg His Leu Thr
            20                  25                  30
Gly Glu Phe Glu Lys Lys Tyr Val Ala Thr Leu Gly Val Glu Val His
        35                  40                  45
Pro Leu Val Phe His Thr Asn Arg Gly Pro Ile Lys Phe Asn Val Trp
    50                  55                  60
Asp Thr Ala Gly Gln Glu Lys Phe Gly Gly Leu Arg Asp Gly Tyr Tyr
65                  70                  75                  80
Ile Gln Ala Gln Cys Ala Ile Ile Met Phe Asp Val Thr Ser Arg Val
                85                  90                  95
Thr Tyr Lys Asn Val Pro Asn Trp His Arg Asp Leu Val Arg Val Cys
            100                 105                 110
Glu Asn Ile Pro Ile Val Leu Cys Gly Asn Lys Val Asp Ile Lys Asp
        115                 120                 125
Arg Lys Val Lys Ala Lys Ser Ile Val Phe His Arg Lys Lys Asn Leu
    130                 135                 140
Gln Tyr Tyr Asp Ile Ser Ala Lys Ser Asn Tyr Asn Phe Glu Lys Pro
145                 150                 155                 160
Phe Leu Trp Leu Ala Arg Lys Leu Ile Gly Asp Pro Asn Leu Glu Phe
                165                 170                 175
Val Ala Met Pro Ala Leu Ala Pro Pro Glu Val Val Met Asp Pro Ala
            180                 185                 190
Leu Ala Ala Gln Tyr Glu His Asp Leu Glu Val Ala Gln Thr Thr Ala
        195                 200                 205
Leu Pro Asp Glu Asp Asp Leu
    210                 215

<210> SEQ ID NO 25
<211> LENGTH: 211
<212> TYPE: PRT
<213> ORGANISM: Homo sapiens

<400> SEQUENCE: 25

Met Thr Pro Trp Leu Gly Leu Ile Val Leu Leu Gly Ser Trp Ser Leu
1               5                   10                  15
Gly Asp Trp Gly Ala Glu Ala Cys Thr Cys Ser Pro Ser His Pro Gln
            20                  25                  30
Asp Ala Phe Cys Asn Ser Asp Ile Val Ile Arg Ala Lys Val Val Gly
        35                  40                  45
Lys Lys Leu Val Lys Glu Gly Pro Phe Gly Thr Leu Val Tyr Thr Ile
    50                  55                  60
Lys Gln Met Lys Met Tyr Arg Gly Phe Thr Lys Met Pro His Val Gln
65                  70                  75                  80
Tyr Ile His Thr Glu Ala Ser Glu Ser Leu Cys Gly Leu Lys Leu Glu
                85                  90                  95
Val Asn Lys Tyr Gln Tyr Leu Leu Thr Gly Arg Val Tyr Asp Gly Lys

```
            100                 105                 110
Met Tyr Thr Gly Leu Cys Asn Phe Val Glu Arg Trp Asp Gln Leu Thr
                115                 120                 125

Leu Ser Gln Arg Lys Gly Leu Asn Tyr Arg Tyr His Leu Gly Cys Asn
            130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
                195                 200                 205

Thr Asp Pro
    210

<210> SEQ ID NO 26
<211> LENGTH: 313
<212> TYPE: PRT
<213> ORGANISM: Homo sapiens

<400> SEQUENCE: 26

Met Pro Val Ala Gly Ser Glu Leu Pro Arg Arg Pro Leu Pro Pro Ala
1               5                   10                  15

Ala Gln Glu Arg Asp Ala Glu Pro Arg Pro His Gly Glu Leu Gln
            20                  25                  30

Tyr Leu Gly Gln Ile Gln His Ile Leu Arg Cys Gly Val Arg Lys Asp
        35                  40                  45

Asp Arg Thr Gly Thr Gly Thr Leu Ser Val Phe Gly Met Gln Ala Arg
    50                  55                  60

Tyr Ser Leu Arg Asp Glu Phe Pro Leu Leu Thr Thr Lys Arg Val Phe
65                  70                  75                  80

Trp Lys Gly Val Leu Glu Glu Leu Leu Trp Phe Ile Lys Gly Ser Thr
                85                  90                  95

Asn Ala Lys Glu Leu Ser Ser Lys Gly Val Lys Ile Trp Asp Ala Asn
            100                 105                 110

Gly Ser Arg Asp Phe Leu Asp Ser Leu Gly Phe Ser Thr Arg Glu Glu
        115                 120                 125

Gly Asp Leu Gly Pro Val Tyr Gly Phe Gln Trp Arg His Phe Gly Ala
    130                 135                 140

Glu Tyr Arg Asp Met Glu Ser Asp Tyr Ser Gly Gln Gly Val Asp Gln
145                 150                 155                 160

Leu Gln Arg Val Ile Asp Thr Ile Lys Thr Asn Pro Asp Asp Arg Arg
                165                 170                 175

Ile Ile Met Cys Ala Trp Asn Pro Arg Asp Leu Pro Leu Met Ala Leu
            180                 185                 190

Pro Pro Cys His Ala Leu Cys Gln Phe Tyr Val Val Asn Ser Glu Leu
        195                 200                 205

Ser Cys Gln Leu Tyr Gln Arg Ser Gly Asp Met Gly Leu Gly Val Pro
    210                 215                 220

Phe Asn Ile Ala Ser Tyr Ala Leu Leu Thr Tyr Met Ile Ala His Ile
225                 230                 235                 240

Thr Gly Leu Lys Pro Gly Asp Phe Ile His Thr Leu Gly Asp Ala His
                245                 250                 255
```

-continued

```
Ile Tyr Leu Asn His Ile Glu Pro Leu Lys Ile Gln Leu Gln Arg Glu
            260                 265                 270

Pro Arg Pro Phe Pro Lys Leu Arg Ile Leu Arg Lys Val Glu Lys Ile
        275                 280                 285

Asp Asp Phe Lys Ala Glu Asp Phe Gln Ile Glu Gly Tyr Asn Pro His
    290                 295                 300

Pro Thr Ile Lys Met Glu Met Ala Val
305                 310
```